(12) United States Patent
Campbell et al.

(10) Patent No.: US 7,902,200 B2
(45) Date of Patent: Mar. 8, 2011

(54) CHEMICAL COMPOUNDS

(75) Inventors: Leonie Campbell, Macclesfield (GB);
Kurt Gordon Pike, Macclesfield (GB);
Abid Suleman, Macclesfield (GB);
Michael James Waring, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 489 days.

(21) Appl. No.: 11/876,370

(22) Filed: Oct. 22, 2007

(65) Prior Publication Data

US 2008/0171734 A1    Jul. 17, 2008

Related U.S. Application Data

(60) Provisional application No. 60/862,493, filed on Oct. 23, 2006, provisional application No. 60/891,993, filed on Feb. 28, 2007.

(51) Int. Cl.
*C07D 401/00* (2006.01)
*A61K 31/4965* (2006.01)

(52) U.S. Cl. .................... 514/255.05; 544/238

(58) Field of Classification Search .................. None
See application file for complete search history.

(56) References Cited

U.S. PATENT DOCUMENTS

| | | | |
|---|---|---|---|
| 2,750,393 A | 6/1956 | Elpern | |
| 2,967,194 A | 1/1961 | Hauptschein | |
| 3,917,625 A | 11/1975 | Lee et al. | |
| 3,950,351 A | 4/1976 | Rossignol et al. | |
| 4,009,174 A | 2/1977 | Cluzan et al. | |
| 4,105,785 A | 8/1978 | Mauvernay et al. | |
| 4,146,631 A | 3/1979 | Ford et al. | |
| 4,434,170 A | 2/1984 | Dostert et al. | |
| 4,474,792 A | 10/1984 | Erickson | |
| 4,634,783 A | 1/1987 | Fujii et al. | |
| 4,966,891 A | 10/1990 | Fujiu et al. | |
| 5,258,407 A | 11/1993 | Washburn et al. | |
| 5,273,986 A | 12/1993 | Holland et al. | |
| 5,399,702 A | 3/1995 | Holland et al. | |
| 5,466,715 A | 11/1995 | Washburn et al. | |
| 5,510,478 A | 4/1996 | Sabb | |
| 5,661,153 A | 8/1997 | Isobe et al. | |
| 5,672,750 A | 9/1997 | Perry | |
| 5,712,270 A | 1/1998 | Sabb | |
| 5,849,735 A | 12/1998 | Albright et al. | |
| 6,110,945 A | 8/2000 | Head et al. | |
| 6,197,798 B1 | 3/2001 | Fink et al. | |
| 6,200,995 B1 | 3/2001 | De la Brouse-Elwood et al. | |
| 6,207,693 B1 | 3/2001 | Setoi et al. | |
| 6,214,878 B1 | 4/2001 | Bernardon et al. | |
| 6,242,474 B1 | 6/2001 | Yamasaki et al. | |
| 6,255,335 B1 | 7/2001 | Himmler et al. | |
| 6,316,482 B1 | 11/2001 | Setoi et al. | |
| 6,320,050 B1 | 11/2001 | Bizzarro et al. | |
| 6,348,474 B1 | 2/2002 | Kayakiri et al. | |
| 6,369,229 B1 | 4/2002 | Head et al. | |
| 6,376,515 B2 | 4/2002 | Zhu et al. | |
| 6,388,071 B2 | 5/2002 | Mahaney | |
| 6,448,399 B1 | 9/2002 | Corbett et al. | |
| 6,486,349 B1 | 11/2002 | Flitter et al. | |
| 6,528,543 B1 | 3/2003 | Bizarro et al. | |
| 6,545,155 B2 | 4/2003 | Corbett et al. | |
| 6,610,846 B1 | 8/2003 | Bizzarro et al. | |
| 6,613,942 B1 | 9/2003 | Ling et al. | |
| 7,132,546 B2 | 11/2006 | Kato et al. | |
| 7,199,140 B2 | 4/2007 | Hayter et al. | |
| 7,230,108 B2 | 6/2007 | Hargreaves et al. | |
| 2001/0027200 A1 | 10/2001 | De la Brouse-Elwood et al. | |
| 2002/0002183 A1 | 1/2002 | Zhu et al. | |
| 2002/0095044 A1 | 7/2002 | Jagtap et al. | |
| 2003/0162690 A1 | 8/2003 | Zhu et al. | |
| 2004/0014968 A1 | 1/2004 | Bizzarro et al. | |
| 2004/0077555 A1 | 4/2004 | Ishihara et al. | |

(Continued)

FOREIGN PATENT DOCUMENTS

CA    2605738    11/2006

(Continued)

OTHER PUBLICATIONS

Diabetes2, http://clinicaltrials.gov/ct2/show/NCT01029795 (2010).*
Diabetes2, http://kidshealth.org/parent/medical/endocrine/prevention.html, 2010.*
Coghlan et al., Expert Opinion Investigational Drugs (2008), 17(2), 145-167.*
Boucherle et al. "Recherches dans la serie des cetones polyphenoliques IV. Thiazoles" Chimica. Therapeutica 3(5):360-363 (1968) (Translation enclosed).
Bowden et al. "Structure-activity relations. Part 10. Metal-ion-complexation studies of a series of substituted benzamidotetrazoles" J. Chem. Research (Synopses) 11:304 (1991).

(Continued)

*Primary Examiner* — Sun Jae Y. Loewe
(74) *Attorney, Agent, or Firm* — Morgan Lewis & Bockius LLP

(57) ABSTRACT

The invention relates to a novel group of compounds of Formula (I) or a salt thereof:

(I)

wherein $R^1$, A and HET-1 are as described in the specification, which may be useful in the treatment or prevention of a disease or medical condition mediated through glucokinase (GLK) such as type 2 diabetes. The invention also relates to pharmaceutical compositions comprising said compounds, methods of treatment of diseases mediated by GLK using said compounds and methods for preparing compounds of Formula (I).

9 Claims, No Drawings

U.S. PATENT DOCUMENTS

| | | |
|---|---|---|
| 2005/0080106 A1 | 4/2005 | Boyd et al. |
| 2005/0148605 A1 | 7/2005 | Grotzfeld et al. |
| 2005/0165074 A1 | 7/2005 | Grotzfeld et al. |
| 2005/0171171 A1 | 8/2005 | Mehta et al. |
| 2005/0171172 A1 | 8/2005 | Lai et al. |
| 2005/0261315 A1 | 11/2005 | Mehta et al. |
| 2006/0004010 A1 | 1/2006 | Habashita et al. |
| 2006/0167053 A1 | 7/2006 | Iino et al. |
| 2006/0258728 A1 | 11/2006 | Tani et al. |
| 2007/0078168 A1 | 4/2007 | Caulkett |

FOREIGN PATENT DOCUMENTS

| | | |
|---|---|---|
| CS | 173097 | 6/1978 |
| EP | 0316704 | 5/1989 |
| EP | 0353452 | 2/1990 |
| EP | 0219436 | 12/1993 |
| EP | 0619116 | 10/1994 |
| EP | 1048659 | 11/2000 |
| EP | 1132381 | 9/2001 |
| EP | 0620216 | 1/2003 |
| EP | 1336607 | 8/2003 |
| EP | 1357116 | 10/2003 |
| EP | 1400540 | 3/2004 |
| EP | 1496052 | 1/2005 |
| EP | 1600442 | 11/2005 |
| EP | 1702919 | 9/2006 |
| FR | 1526074 | 5/1968 |
| FR | 2088019 | 1/1972 |
| GB | 1352415 | 5/1974 |
| GB | 1561350 | 2/1980 |
| GB | 1588242 | 4/1981 |
| GB | 2216517 | 10/1989 |
| GB | 2331748 | 6/1999 |
| GB | 2385328 | 8/2003 |
| JP | 50105559 | 8/1975 |
| JP | 57021320 | 2/1982 |
| JP | 57075962 | 5/1982 |
| JP | 58069812 | 4/1983 |
| JP | 61205937 | 9/1986 |
| JP | 62158252 | 7/1987 |
| JP | 04300832 | 10/1992 |
| JP | 04300874 | 10/1992 |
| JP | 06027025 | 2/1994 |
| JP | 08143565 | 6/1996 |
| JP | 08173525 | 7/1996 |
| JP | 08301760 | 11/1996 |
| JP | 09040557 | 2/1997 |
| JP | 09202786 | 8/1997 |
| JP | 10101671 | 4/1998 |
| JP | 10101672 | 4/1998 |
| JP | 10212271 | 8/1998 |
| JP | 11029480 | 2/1999 |
| JP | 11171848 | 6/1999 |
| JP | 11222435 | 8/1999 |
| JP | 11292879 | 10/1999 |
| JP | 2000086657 | 3/2000 |
| WO | WO 91/09017 | 6/1991 |
| WO | WO 94/04525 | 3/1994 |
| WO | WO 94/12461 | 6/1994 |
| WO | WO 95/20578 | 8/1995 |
| WO | WO 95/35298 | 12/1995 |
| WO | WO 96/11902 | 4/1996 |
| WO | WO 96/19455 | 6/1996 |
| WO | WO 96/22282 | 7/1996 |
| WO | WO 96/22293 | 7/1996 |
| WO | WO 96/22294 | 7/1996 |
| WO | WO 96/22295 | 7/1996 |
| WO | WO 96/36619 | 11/1996 |
| WO | WO 96/41795 | 12/1996 |
| WO | WO 97/24355 | 7/1997 |
| WO | WO 97/36480 | 10/1997 |
| WO | WO 97/46560 | 12/1997 |
| WO | WO 97/49707 | 12/1997 |
| WO | WO 97/49708 | 12/1997 |
| WO | WO 98/24771 | 6/1998 |
| WO | WO 98/34632 | 8/1998 |
| WO | WO 98/45242 | 10/1998 |
| WO | WO 99/00359 | 1/1999 |
| WO | WO 99/00372 | 1/1999 |
| WO | WO 99/17777 | 4/1999 |
| WO | WO 99/20611 | 4/1999 |
| WO | WO 99/24415 | 5/1999 |
| WO | WO 99/26944 | 6/1999 |
| WO | WO 99/32477 | 7/1999 |
| WO | WO 99/38845 | 8/1999 |
| WO | WO 99/54301 | 10/1999 |
| WO | WO 99/62901 | 12/1999 |
| WO | WO 00/02850 | 1/2000 |
| WO | WO 00/26202 | 5/2000 |
| WO | WO 00/39118 | 7/2000 |
| WO | WO 00/46203 | 8/2000 |
| WO | WO 00/58293 | 10/2000 |
| WO | WO 01/00579 | 1/2001 |
| WO | WO 01/12621 | 2/2001 |
| WO | WO 01/16097 | 3/2001 |
| WO | WO 01/19788 | 3/2001 |
| WO | WO 01/20327 | 3/2001 |
| WO | WO 01/26652 | 4/2001 |
| WO | WO 01/32639 | 5/2001 |
| WO | WO 01/44216 | 6/2001 |
| WO | WO 01/64642 | 9/2001 |
| WO | WO 01/64643 | 9/2001 |
| WO | WO 01/74791 | 10/2001 |
| WO | WO 01/83465 | 11/2001 |
| WO | WO 01/83478 | 11/2001 |
| WO | WO 01/85706 | 11/2001 |
| WO | WO 01/85707 | 11/2001 |
| WO | WO 02/00633 | 1/2002 |
| WO | WO 02/08209 | 1/2002 |
| WO | WO 02/14312 | 2/2002 |
| WO | WO 02/24682 | 3/2002 |
| WO | WO 02/26718 | 4/2002 |
| WO | WO 02/26731 | 4/2002 |
| WO | WO 02/28835 | 4/2002 |
| WO | WO 02/42270 | 5/2002 |
| WO | WO 02/46173 | 6/2002 |
| WO | WO 02/48106 | 6/2002 |
| WO | WO 02/051831 | 7/2002 |
| WO | WO 02/064545 | 8/2002 |
| WO | WO 02/079145 | 8/2002 |
| WO | WO 03/000262 | 1/2003 |
| WO | WO 03/000267 | 1/2003 |
| WO | WO 03/015518 | 2/2003 |
| WO | WO 03/015774 | 2/2003 |
| WO | WO 03/022856 | 3/2003 |
| WO | WO 03/024222 | 3/2003 |
| WO | WO 03/026652 | 4/2003 |
| WO | WO 03/028641 | 4/2003 |
| WO | WO 03/047626 | 6/2003 |
| WO | WO 03/048152 | 6/2003 |
| WO | WO 03/051366 | 6/2003 |
| WO | WO 03/055482 | 7/2003 |
| WO | WO 03/066613 | 8/2003 |
| WO | WO 03/080585 | 10/2003 |
| WO | WO 03/082838 | 10/2003 |
| WO | WO 03/095438 | 11/2003 |
| WO | WO 03/097824 | 11/2003 |
| WO | WO 2004/002481 | 1/2004 |
| WO | WO 2004/022536 | 3/2004 |
| WO | WO 2004/031179 | 4/2004 |
| WO | WO 2004/045614 | 6/2004 |
| WO | WO 2004/046139 | 6/2004 |
| WO | WO 2004/050645 | 6/2004 |
| WO | WO 2004/052869 | 6/2004 |
| WO | WO 2004/063179 | 7/2004 |
| WO | WO 2004/063194 | 7/2004 |
| WO | WO 2004/072031 | 8/2004 |
| WO | WO 2004/072066 | 8/2004 |
| WO | WO 2004/076420 | 9/2004 |
| WO | WO 2004/081001 | 9/2004 |
| WO | WO 2004/085385 | 10/2004 |
| WO | WO 2004/085406 | 10/2004 |
| WO | WO 2004/110350 | 12/2004 |
| WO | WO 2004/110375 | 12/2004 |
| WO | WO 2005/044801 | 5/2005 |
| WO | WO 2005/048953 | 6/2005 |

| WO | WO 2005/049019 | 6/2005 |
| WO | WO 2005/054200 | 6/2005 |
| WO | WO 2005/054233 | 6/2005 |
| WO | WO 2005/056530 | 6/2005 |
| WO | WO 2005/063738 | 7/2005 |
| WO | WO 2005/066145 | 7/2005 |
| WO | WO 2005/080359 | 9/2005 |
| WO | WO 2005/080360 | 9/2005 |
| WO | WO 2005/090332 | 9/2005 |
| WO | WO 2005/095417 | 10/2005 |
| WO | WO 2005/095418 | 10/2005 |
| WO | WO 2005/103021 | 11/2005 |
| WO | WO 2005/012132 | 12/2005 |
| WO | WO 2005/121110 | 12/2005 |
| WO | WO 2006/016174 | 2/2006 |
| WO | WO 2006/016178 | 2/2006 |
| WO | WO 2006/016194 | 2/2006 |
| WO | WO 2006/040527 | 4/2006 |
| WO | WO 2006/040528 | 4/2006 |
| WO | WO 2006/040529 | 4/2006 |
| WO | WO 2006/066613 | 6/2006 |
| WO | WO 2006/114180 | 11/2006 |
| WO | WO 2006/125958 | 11/2006 |
| WO | WO 2006/125972 | 11/2006 |
| WO | WO 2007/007040 | 1/2007 |
| WO | WO 2007/007041 | 1/2007 |
| WO | WO 2007/007042 | 1/2007 |
| WO | WO 2007/017649 | 2/2007 |
| WO | WO 2007/028135 | 3/2007 |
| WO | WO 2007/031739 | 3/2007 |
| WO | WO 2007/053657 | 5/2007 |
| WO | WO 2007/060448 | 5/2007 |
| WO | WO 2008/050101 | 5/2008 |
| WO | WO 2008/050117 | 5/2008 |
| WO | WO 2008/075073 | 6/2008 |

OTHER PUBLICATIONS

Bowden et al. "Structure-activity relations. Part 13. Inhibitors of cyclic nucleotide phosphodiesterase and anaphylaxis. Inhibition by a series of substituted benzamidotetrazoles" J. Chem. Research (Synopses) 6:206 (1992).

Brenner et al. "Imino-bridged heterocycles. VII. (1) N-aminobenzocycloheptapyridinimines" J. Heterocyclic Chem. 23:1331-1332 (1986).

Brocklehurst et al. "Stimulation of hepatocyte glucose metabolism by novel small molecule glucokinase activators" Diabetes 53:535-541 (2004).

Caro et al. "Liver glucokinase: Decreased activity in patients with type II diabetes" Horm. Metab. Res. 27(1):19-22 (1995).

Carroll et al. "The in vitro characterisation of a novel Glucokinase activator" Stress, Signalling and Control, Biochemical Society Meeting 679, University of Essex, UK (Jul. 2-4, 2003).

Caulfield et al. "The first potent and selective inhibitors of the glycine transporter type 2" J. Med. Chem. 44(17):2679-2682 (2001).

Cavier et al. "Recherches sur les derives nitres d'interet biologique. XVI. Relations entre structures et activites protozoocides, anthelminthiques et molluscicides dans la serie du benzamido-2 nitro-5 thiazole" European Journal of Medicinal Chemistry, Chimica Therapeutica 13(6): 539-543 (1978) (Translation enclosed).

Chemical Abstracts Service, Columbus, Ohio, US: CAS Registry No. 438028-05-8 (Nov. 15, 2001); CAS Registry No. 438024-90-9, [XP002272448].

Chemical Abstracts Service, Columbus, Ohio, US: CAS Registry No. 445284-93-5 (Jul. 9, 2002); CAS Registry No. 445250-52-2 (Jul. 9, 2002); CAS Registry No. 445030-98-8 (Jul. 9, 2002); CAS Registry No. 445017-74-3 (Jul. 9, 2002); CAS Registry No. 444935-78-8 (Jul. 9, 2002); CAS Registry No. 444923-81-3 (Jul. 9, 2002); CAS Registry No. 438222-80-1 (Jul. 9, 2002); CAS Registry No. 438221-01-3 (Jul. 9, 2002);CAS Registry No. 354550-59-7 (Jul. 9, 2002); CAS Registry No. 438537-80-5 (Jul. 9, 2002); CAS Registry No. 353770-14-6 (Jul. 9, 2002); CAS Registry No. 352690-95-0 (Jul. 9, 2002); CAS Registry No. 353478-21-4 (Jul. 9, 2002); CAS Registry No. 353477-20-0 (Jul. 9, 2002); CAS Registry No. 353474-36-9 (Jul. 9, 2002); CAS Registry No. 362473-72-1 (Jul. 9, 2002); CAS Registry No. 303140-37-6 (Jul. 9, 2002); [XP002272449].

Chemical Abstracts Service, Columbus, Ohio, US: CAS Registry No. 354767-51-4 (Sep. 5, 2001).

Chemical Abstracts Service, Columbus, Ohio, US: CAS Registry No. 354767-66-1 (Sep. 5, 2001).

Christesen et al. "The second activating glucokinase mutation (A456V): Implications for glucose homeostasis and diabetes therapy" Diabetes 51(4):1240-1246 (2002).

Ciaceri et al. "Analgesic, antipyretic and anti-inflammatory action of some new acids of the phenylethylenethiazole series" Minerva Medica 63(42):2409-2413 (1972).

Coburn et al. "Mesoionic purinone analogs IV: Synthesis and in vitro antibacterial properties of mesoionic thiazolo(3,2-α)pyrimidin-5,7-diones and mesoionic 1,3,4-thiadizolo(3,2-α)pyrimidin-5,7-diones" J. Pharm. Sciences. 62(11):1785-1789 (1973).

Coghlan "Small molecule Glucokinase Activators (GKAs) as novel anti-diabetic agents" CIDEM seminar (May 2005).

Coghlan "Small molecule Glucokinase Activators (GKAs) as novel anti-diabetic agents" Society for Medicines Research Seminar (Jun. 2004).

Coope et al. "Predictive blood glucose lowering efficacy by Glucokinase activators in high fat fed female Zucker rats" British Journal of Pharmacology 149(3):328-335 (2006).

Corbett "Glucokinase activators: Discovery of novel, orally active glucose lowering agents" Abstract, Cambridge Healthtech Institute's Eleventh Annual Molecular Medicine Tri-Conference, Moscone West Convention Center, San Francisco, CA (Mar. 24-26, 2004).

Corbett "Glucokinase activators: Discovery of novel, orally active glucose lowering agents" Presentation Slides, Cambridge Healthtech Institute's Eleventh Annual Molecular Medicine Tri-Conference, Moscone West Convention Center, San Francisco, CA (Mar. 24-26, 2004).

Cushman et al. "Synthesis and evaluation of new protein-tyrosine kinase inhibitors. Part 1. Pyridine-containing stilbenes and amides" Bioorganic & Medicinal Chemistry Letters 1(4):211-214 (1991).

De Paulis et al. "Potential antipsychotic agents. 6. Synthesis and antidopaminergic properties of substituted N-(1-benzyl-4-piperidinyl)salicylamides and related compounds. QSAR based design of more active members" Eur. J. Med. Chem. 25:507-517 (1990).

DeFronzo et al. "The triumvirate: β-cell, muscle, liver. A collusion responsible for NIDDM" Diabetes 37:667-687 (1988).

DeJohn et al. "Functionalization of Substituted 2(1H)- and 4(1H)-Pyridones. III. The preparation of substituted 6-vinyl-1,2-dihydro-2-oxo- and 1,4-dihydro-4-oxo-3-pyridinecarboxylic acids through the chemistry of pyridone dianions" J. Heterocyclic Chem. 20(5):1295-1302 (1983).

Desai et al. "Phenotypic correction of diabetic mice by adenovirus-mediated glucokinase expression" Diabetes 50:2287-2295 (2001).

Edmont et al. "Synthesis and evaluation of quinoline carboxyguanidines as antidiabetic agents" Bioorg. Med. Chem. Lett. 10(16):1831-1834 (2000).

Elpern et al. "Iodinated Benzamidotetrazoles" J. Org. Chem. 22: 1686 (1957).

Ferre et al. "Correction of diabetic alterations by glucokinase" PNAS USA 93(14):7225-7230 (1996).

Ford et al. "Synthesis and quantitative structure-activity relationships of antiallergic 2-hydroxy-N-1H-tetrazol-5-ylbenzamides and N-(2-hydropheny)-1H-tetrazole-5-carboxamides" J. Med. Chem. 29(4):538-549 (1986).

Froguel et al. "Familial hyperglycemia due to mutations in glucokinase—Definition of a subtype of diabetes mellitus" New Engl. J. Med. 328:697-702 (1993).

Fujimoto et al. "Administration of D-glucosamine into the third cerebroventricle induced feeding accompanied by hyperglycemia in rats" Life Sciences 37(26):2475-2482 (1985).

Gill et al. "Stimulation of insulin release by a small molecule glucokinase activator" EASD Islet Study Group, Abstract (Nov. 2005).

Gill et al. "Stimulation of Insulin Release in MIN6 Cells and Isolated Rodent Islets by a Small Molecule Glucokinase Activator (GKA50)" Poster presented at 42nd EASD Meeting Copenhagen (2006) and Diabetologia vol. 49 (Supplement 1) 0501 (2006).

Gill et al. "Upregulation of key β-cell genes and improvement of function in rodent islets following chronic in vitro treatment with a glucokinase activator" Poster presented at 43rd EASD Meeting, Amsterdam (Sep. 17-21, 2007) and Diabetologia vol. 50 (Supplement 1) S218 (2007).

Glaser et al. "Familial hyperinsulinism caused by an activating glucokinase mutation" The New England Journal of Medicine 338(4):226-230 (1998).

Gorman et al. "Effect of high-fat diet on glucose homeostasis and gene expression in Glucokinase (GK) heterozygous knock-outs" Abstract Number: 0108-OR 67th Annual Scientific Sessions, American Diabetes Association, Chicago, IL, (Jun. 22-26, 2007).

Grimsby "Glucokinase activators: Potential treatment for type 2 diabetes" Roche, SMi Diabetes, London, UK (Oct. 28-29, 2002).

Grimsby et al. "Allosteric activators of glucokinase: Potential role in diabetes therapy" Science 301(5631):370-373 (2003).

Guertin et al. "Small molecule glucokinase activators as glucose lowering agents: A new paradigm for diabetes therapy" Current Medicinal Chemistry 13(15):1839-1843 (2006).

Hashimoto et al. "Evaluation of differentiation-inducing activity of retinoids on human leukemia cell lines HL-60 and NB4" Biol. Pharm. Bull. 19(10):1322-1328 (1996).

Hirst et al. "Molecular recognition of phosphate esters: A balance of hydrogen bonding and proton transfer interactions" Israel Journal of Chemistry 32:105-111 (1992).

Horsak et al. "Method of evaluation of the phase diagram of a system with formation of a compound" Chem. Zvesti. 36(3):311-320 (1982).

Isomura et al. "Z-type deposition of a polymerizable amphiphile to fabricate an immobilized LB film showing strong second harmonic generation" Thin Solid Films 244:939-942 (1994).

Johnson et al. "Glucose-dependent modulation of insulin secretion and intracellular calcium ions by GKA50—A glucokinase activator" Abstract Number: 0592-P, 67th Annual Scientific Sessions, American Diabetes Association, Chicago, IL (Jun. 22-26, 2007).

Julia et al. "Synthesis of a 2,3,4,4a,5,6-hexahydrobenzo[f]quinoline system by "aryne substitution"" Bull Chem Soc France 11:4463-4467 (1968) (Translation enclosed).

Kamata et al. "Pyroelectricity of noncentrosymmetric Langmuir-Blodgett films of phenylpyrazine derivatives" Japan J. Appl. Phys. 33(2):1074-1078 (1994).

Kar "Cinchophen analogues as potential CNS agents" J Pharm Sci. 72(9):1082-1084 (1983).

Knoppova et al. "Synthesis and properties of 5-styryl-2-furancarboxlic acids" Collection Czechoslovak Chem. Commun. 46:2716-2728 (1981).

Konig et al. "Binding of heptanedioic acid to a threefold pyridine arylamide receptor. Enhancement of the stability of supramolecular solution structures by multiple binding sites" J. Org. Chem. 60(13):4291-4293 (1995).

Kunishima et al. "4-(4,6-Dimethoxy-1,3,5-triazin-2-yl)-4-methylmorpholinium chloride: An efficient condensing agent leading to the formation of amides and esters" Tetrahedron 55:13159-13170 (1999).

Kurata et al. "D-Glucose suppression of eating after intra-third ventricle infusion in rat" Physiology & Behavior 37:615-620 (1986).

Kurata et al. "Structural evaluation of glucose analogues on feeding elicitation in rat" Metabolism 38(1):46-51 (1989).

Lai et al. "Formation of columnar arrangements in copper(ii) complexes of 2-phenylazomethinopyridine derivatives" J. Materials Chemistry 8(11):2379-2383 (1998).

Leighton et al. "Improved glycemic control after sub-acute administration of a Glucokinase activator to male zucker (fa/fa) rats" Abstract Number: 0377-OR, 67th Annual Scientific Sessions, American Diabetes Association, Chicago, IL (Jun. 22-26, 2007).

Leighton et al. "Small molecule glucokinase activators as novel antidiabetic agents" Biochemical Society Transactions 33(Part 2):371-374 (2005).

Levin "Glucosensing neurons do more than just sense glucose" International Journal of Obesity 25(Suppl 5): S68-S72 (2001).

Levin et al. "Brain glucose sensing and body energy homeostasis: role in obesity and diabetes" Am. J. Physiol. 276(5 Pt 2):R1223-R1231 (1999).

Levin et al. "Differential effects of diet and obesity on high and low affinity sulfonylurea binding sites in the rat brain" Brain Research 739(1-2):293-300 (1996).

Alvarez et al. "Evidence that glucokinase regulatory protein is expressed and interacts with glucokinase in rat brain" J. Neurochem. 80(1):45-53 (2002).

Alvarez et al. "Expression of the glucagon-like peptide-1 receptor gene in rat brain" J. Neurochem. 66(3):920-927 (1996).

Anderson et al "Pyridopyrimidines. 6. Nucleophilic substitutions in the pyrido[2,3-d]pyrimidine series" J. Org. Chem. 42(6):993-996 (1977).

Ando et al. "Fluoride salts on alumina as reagents for alkylation of phenols and alcohols" Bull. Chem. Soc. Jpn. 55(8):2504-2507 (1982).

Atwell et al. "Potential antitumor agents. VI. Bisquaternary salts" J. Med. Chem. 11(2):295-300 (1968).

Baker et al. "Structure and synthesis of Pallescansin E utilising a modified Wadsworth-Emmons reaction" J. Chem. Soc., Perkin Trans. 1, 12:3087-3091 (1981).

Baker et al. "Synthesis of Pallescensin-E: Use of crown ether in the Wadsworth procedure for olefin formation" Tetrahedron Letters 22:161-162 (1981).

Balant et al. "Metabolic considerations in prodrug desing" Chapter twenty-three, Burger's Medicinal Chemistry and Drug Discovery, 5th Edition, vol. 1, NY: John Wiley & Sons, Inc. 949-982 (1995).

Beilstein Registry No. 6511458 (Apr. 18, 1994) [XP002272206].

Bell et al. "Glucokinase mutations, insulin secretion, and diabetes mellitus" Annu. Rev. Physiol. 58:171-186 (1996).

Beller et al. "Photochemical synthesis of benzo[f]quinolines" J Org Chem. 42(22):3514-3518 (1977).

Berl et al. "Induced fit selection of a barbiturate receptor from a dynamic structural and conformational/ configurational library" European J. Org. Chem. (11):3089-3094 (1999).

Berl et al. "Template-induced and molecular recognition directed hierarchical generation of supramolecular assemblies from molecular strands" Chem. Eur. J. 6(11):1938-1946 (2000).

Bonina et al. "Synthesis and pharmacologic activity of 2-arylethenylthiazol-4-acetic and 4-carboxylic acids" II Farmaco 40(11):875-884 (1985).

Coghlan et al., "Glucokinase activators in diabetes management" Expert Opin. Investig. Drugs 17(2):145-167 (2008).

Leighton, "Pre-clinical disease models—challenges and success stories"44th Drug Information Association Annual Meeting, Boston, MA, US (2008).

Lith, "Evaluation of the effects on whole body glucose metabolism after single doses of X2000—A glucose lowering agent" Poster presentation, Master thesis in Pharmaceutical Bioscience, Goteborgs University (2008).

Ralph et al. "Glucose Modulation of Glucokinase Activation by Small Molecules" Biochemistry 47(17):5028-5036 (2008).

Sarabu et al., "Glucokinase activators as new type 2 diabetes therapeutic agents" Expert Opinion on Therapeutic Patents 18(7):759-768 (2008).

Shorvon, "Pyrrolidone derivatives" Lancet 358(9296):1885-1892 (2001).

Eycken et al., Synthesis of (E)-5-(2-arylvinyl)-2-(hetero)arylpyridines, (E)-2-(2-arylvinyl)-5-methoxycarbonylpyridines and (E,E)-2,5-bis(2-arylvinyl)pyridines as polarity and pH probes, 2002, J. Chem. Soc., Perkin. Trans. 2, p. 929.

Robertson et al. "Structure-activity relationships of arylimidazopyridine cardiotonics: discovery and inotropic activity of 2-[2-methoxy-4-(methylsulfinyl)phenyl]-1H-imidazo[4,5-c]pyridine" Journal of Medicinal Chemistry 28:717-727 (1985).

West, Anthony R., "Solid State Chemistry and its Applications" Wiley, New York, pp. 358 and 365 (1988).

Wolff, Manfred E. "Burger's Medicinal Chemistry", 5th Edition, Part I, John Wiley & Sons, pp. 975-977 (1995).

Levin et al. "In vivo and in vitro regulation of [3H]glyburide binding to brain sulfonylurea receptors in obesity-prone and resistant rats by glucose" Brain Research 776(1-2):146-153 (1997).

Levin et al. "Reduced glucose-induced neuronal activation in the hypothalamus of diet-induced obese rats" Brain Research 808(2):317-319 (1998).

Levkoev et al. "Research on cyanide dyes 11. 7,7'-Dimethylthiacarbocyanines" Zhurnal Obshchei Khimii 27:3097-3107 (1957) (Translation enclosed).

Lynch et al. "Localization of glucokinase gene expression in the rat brain" Diabetes 49(5):693-700 (2000).

Mastafanova et al. "Features of the catalytic reduction of 4-(3-oxoquinuclidyl-2-methylene)-6-methoxyquinoline and its ethyleneketal" Khimiya Geterotsilclicheslcikh Soedinenii (1):86-94 (1989) (Translation enclosed).

Mastafanova et al. "Synthesis and study of the antihypertensive activity of substituted N-acetylmercaptopropionyl-6-[2'-phenylethyl]pipecolinic acids" Khimiko Farmatsevticheskii Zhurnal 22(3):294-302 (1988).

Mastafanova et al. "Synthesis, Anti-Inflammatory and Analgesic Activity of 1,6-Disubstituted Pipecolic and 6-Substituted Picolinic Acids" Khimiko Farmatsevticheskii Zhurnal 22(4) 428-431 (1988).

Mazik et al. "Molecular recognition of carbohydrates by artificial receptors: systematic studies towards recognition motifs for carbohydrates" Chem. Eur. J. 7(3):664-670 (2001).

Mazik et al. "Molecular recognition of carbohydrates by artificial polypyridine and polypyrimidine receptors" Angewandte Chemie International Edition 39(3):551-554 (2000).

McKerrecher "Design and synthesis of novel glucokinase activators" 13th RSC-SCI Medicinal Chemistry Symposium, Churchill College, Cambridge (Sep. 4-7, 2005).

McKerrecher et al. "Design & synthesis of novel glucokinase activators as potential treatments for type 2 diabetes" 233rd ACS National Meeting, Chicago, IL (Mar. 25-29, 2007).

McKerrecher et al. "Design and synthesis of novel glucokinase activators as potential treatment for type 2 diabetes" Frontiers in Medicinal Chemistry, Frankfurt (Mar. 12-15, 2006).

McKerrecher et al. "Design of a potent, soluble glucokinase activator with excellent in vivo efficacy" Bioorg. Med. Chem. Lett. 16(10):2705-2709 (2006 May 15) Epub Feb. 28, 2006.

McKerrecher et al. "Discovery, synthesis and biological evaluation of novel glucokinase activators" Bioorg Med Chem Lett. 15(8):2103-2106 (2005).

McKerrecher et al. "Identification of orally bioavailable small molecule activators of glucokinase" Abstract, 12$^{th}$ SCI-RSC Medicinal Chemistry Symposium, Cambridge, UK, 7-10 Sep. 2003 (poster 21) and 227$^{th}$ American Chemical Society National Meeting and Exposition, San Francisco, California, Mar. 28-Apr. 1, 2004 (paper 341).

McKerrecher et al. "Identification of orally bioavailable small molecule activators of glucokinase" Abstract, Anglo-Swedish Medicinal Chemistry Meeting (Mar. 2005).

Meijer et al "Chiral amplification in supramolecular stacks" Polymer Preprints 41(1):902-903 (2000).

Mobbs et al. "Brain glucose-sensing mechanisms: ubiquitous silencing by aglycemia vs. hypothalamic neuroendocrine responses" Am. J. Physiol. Endocrinol. Metab. 281(4):E649-E654 (2001).

Moore et al. "Acute fructose administration improves oral glucose tolerance in adults with type 2 diabetes" Diabetes Care 24(11):1882-1887 (2001).

Motesharei et al. "Molecular recognition in membrane mimics: A fluorescence probe" J. Am. Chem. Soc. 116(16):7413-7414 (1994).

Motesharei et al. "Molecular recognition on functionalized self-assembled monolayers of alkanethiols on gold" J. Am. Chem. Soc. 120(29): 7328 -7336 (1998).

Palmans "Extended-core discotic liquid crystals based on the intramolecular H-bonding in N-acylated 2,2'-bipyridine-3,3'-diamine moieties" Chem. Eur. J. 3(2):300-307 (1997).

Plieninger et al. "Synthesis of 7,8-dihydro-5,6-benzoquinoline-(3)-carboxylic acid" Chemische Berichte 87:882-887 (1954) (Translation enclosed).

Printz et al. "Mammalian glucokinase" Annu. Rev. Nutr. 13:463-496 (1993).

Prousek et al. "Preparation and electron transfer-induced cis-trans isomerization reactions of 1-(5-nitro-2-furyl)-, 1-(5- nitro-2-thienyl)-, and 1-(4-nitrophenyl)-2-R ethylenes" Collect. Czech. Chem. Commun. 54:1675-1682 (1989).

Qian-Cutrone et al. "Glucolipsin A and B, two new glucokinase activators produced by Streptomyces purpurogenescleroticus and Nocardia vaccinii" Journal of Antibiotics (Tokyo), 52(3):245-255 (1999).

Rivalle et al. "2,3 Disubstituted furans and pyrroles - XVIII: Synthesis annd rearrangement of 4H-dihydro-9,10 benzo[4,5]cyclohepta[1,2-b]furannones-4" Tetrahedron 32(7):829-834 (1976).

Rogers et al. "Mesoionic purinone analogues as inhibitors of cyclic-AMP phosphodiesterase: a comparison of several ring systems" J. Med. Chem. 24(11):1284-1287 (1981).

Roncero et al. "Functional glucokinase isoforms are expressed in rat brain" J. Neurochem. 74(5):1848-1857 (2000).

Rowe et al. "Potassium channel dysfunction in hypothalamic glucose-receptive neurones of obese Zucker rats" Journal of Physiology 497.2:365-377 (1996).

Schuit et al. "Glucose sensing in pancreatic β-Cells. A model for the study of other glucose-regulated cells in gut, pancreas, and hypothalamus" Diabetes 50:1-11 (2001).

Sekera et al. "No. 69. —Recherches sur les anesthesiques locaux (XI memoire) Synthese de quelques nouveaux βalcoxyethoxycarbanilates et β-alcoxyethoxycinchonamides amines" Soc. Chim , 5th Series, Memoires 401-404 (1959) (Translation enclosed).

Seoane et al. "Glucokinase overexpression restores glucose utilization and storage in cultured hepatocytes from male Zucker diabetic fatty rats" J Biol Chem. 274(45):31833-31838 (1999).

Shiota et al. "Glucokinase gene locus transgenic mice are resistant to the development of obesity-induced type 2 diabetes" Diabetes 50(3):622-629 (2001).

Spanswick et al. "Insulin activates ATP-sensitive K+ channels in hypothalamic neurons of lean, but not obese rats" Nature Neuroscience 3(8):757-758 (2000).

Spanswick et al. "Leptin inhibits hypothalamic neurons by activation of ATP-sensitive potassium channels" Nature 390(6659):521-525 (1997).

Stout et al. "Synthesis and antiarrhythmic and parasympatholytic properties of substituted phenols. 3. Modifications to the linkage region (region 3)" J. Med. Chem. 28(3):295-298 (1985).

Suhua et al. "Synthesis and biological activity of tyrosine protein kinase inhibitors" Acta Pharmaceutica Sinica 32(7): 515-523 ()997).

Tecilla et al. "Hydrogen-bonding self-assembly of multichromophore structures" J. Am. Chem. Soc. 112:9408-9410 (1990).

Tecilla et al. "Synthetic hydrogen bonding receptors as models of transacylase enzymes" Tetrahedron 51(2):435-448 (1995).

Tecilla et al. "Transition-state stabilization and molecular recognition: acceleration of phosphoryl-transfer reactions by an artificial receptor" J. Am. Chem. Soc. 112:9586-9590 (1990).

Tornetta et al. "Arylvinylthiazole derivatives with anti-inflammatory, analgesic and anti-pyretic activity" Bollettino Delle Sedute Accad. Giovenia Sci. Nat. Catanica. Series 6, 11(9-10):89-95 (1973) (Translation enclosed).

Tucker et al. "Novel Inhibitors of prolyl 4-hydroxylase. 2. 5-amide substituted pyridine-2-carboxylic acids" J. Med. Chem. 3(5)5:804-807 (1992).

Van Gorp et al. "C3-symmetrical supramolecular architectures: fibers and organic gels from discotic trisamides and trisureas" .J Am. Chem. Soc. 124(49):14759-14769 (2002).

Vanderstelt et al. " Synthesis and pharmacological properties of some derivatives of 5H-benzo[4,5] cyclohepta[1,2-b] pyridine and of 11H-benzo[5,6] cyclohepta[1,2-c] pyridine III" Arzneim. Forsch. 22(1):133-137 (1972).

Velho et al. "Impaired hepatic glycogen synthesis in glucokinase-deficient (MODY-2) subjects" J. Clin. Invest. 98(8):1755-1761 (1996).

Vertigan et al. "Impact of cell glycogen content on modulation of hepatocyte glucose metabolism by pharmacological agents" Diabetologia, 47 Supp 1, A 214, 589 (2004).

Williams et al. "Meeting the needs of type 2 diabetes patients" Highlights from the society for medicines research symposium type II diabetes: Mechanisms and emerging therapeutic targets, held Jun. 17, 2004, in London, United Kingdom, Drug News and Perspectives, 17(8) 1-4 (Oct. 2004).

Winzell et al. "Glucokinase Activation Reduces Glycemia and Improves Glucose Tolerance in Mice with High-fat Diet-induced Insulin Resistance" Abstract No.: 1482-P, 67th Annual Scientific Sessions, American Diabetes Association, Chicago, IL (Jun. 22 - 26, 2007) and Diabetes vol. 56 (Supplement 1) 1482-P(2007).

Yakushijin et al. "Intramolecular ring formation of phenyl azide and furan" Heterocycles 12(8):1021-1026 (1979).

Yakushijin et al. "Intramolecular ring formation of phenyl azide and furan moieties" Chem. Pharm. Bull. 30(1):140-151 (1982).

Yang et al. "Hypothalamic glucose sensor: similarities to and differences from pancreatic beta-cell mechanisms" Diabetes 48(9):1763-1772 (1999).

Yoshina et al. "Studies of heterocyclic compounds. II. Synthesis of 2-furylvinyl-benzenes and studies of polarography" Yakugaku Zasshi 88(4):398-404 (1968).

Yoshina et al. "Studies of heterocyclic compounds. III. Synthesis of methyl 5-(2-phenylvinyl)2-furoate" Yakugaku Zasshi 88(4):405-409 (1968).

Yoshina et al. "Studies of heterocyclic compounds. IV. Ultraviolet spectra of 2-(2-furyl)vinylbenzenes and 2-(2- furyl)vinylfurans" Yakugaku Zasshi 88(4):410-416 (1968).

Yoshina et al. "Studies of heterocyclic compounds. VI. 2-(Carbomethoxy-2-furyl)vinyl benzenes and their ultraviolet spectra" Yakugaku Zasshi 88(4):977-983 (1968).

Youssefyeh et al. "Development of high-affinity 5-HT3 receptor antagonists. 1. Initial structure-activity relationship of novel benzamides" J. Med. Chem. 35(5): 895-903 (1992).

Zhang et al. "Synthesis based on affinity separation (SAS): separation of products having barbituric acid tag from untagged compounds by using hydrogen bond interaction" Synlett 5:590-596 (2001).

* cited by examiner

CHEMICAL COMPOUNDS

This application claims the benefit under 35 U.S.C §119(e) of Application No. 60/862,493 US-1 filed on 23 Oct. 2006 and 60/891,993 US-2 filed on 28 Feb. 2006.

The present invention relates to a group of benzoyl amino heterocyclyl compounds which may be useful in the treatment or prevention of a disease or medical condition mediated through glucokinase (GLK or GK), leading to a decreased glucose threshold for insulin secretion. In addition the compounds are predicted to lower blood glucose by increasing hepatic glucose uptake. Such compounds may have utility in the treatment of Type 2 diabetes and obesity. The invention also relates to pharmaceutical compositions comprising said compounds and to methods of treatment of diseases mediated by GLK using said compounds.

In the pancreatic β-cell and liver parenchymal cells the main plasma membrane glucose transporter is GLUT2. Under physiological glucose concentrations the rate at which GLUT2 transports glucose across the membrane is not rate limiting to the overall rate of glucose uptake in these cells. The rate of glucose uptake is limited by the rate of phosphorylation of glucose to glucose-6-phosphate (G-6-P) which is catalysed by glucokinase (GLK) [1]. GLK has a high (6-10 mM) Km for glucose and is not inhibited by physiological concentrations of G-6-P [1]. GLK expression is limited to a few tissues and cell types, most notably pancreatic β-cells and liver cells (hepatocytes) [1]. In these cells GLK activity is rate limiting for glucose utilisation and therefore regulates the extent of glucose induced insulin secretion and hepatic glycogen synthesis. These processes are critical in the maintenance of whole body glucose homeostasis and both are dysfunctional in diabetes [2].

In one sub-type of diabetes, Maturity-Onset Diabetes of the Young Type 2 (MODY-2), the diabetes is caused by GLK loss of function mutations [3,4]. Hyperglycaemia in MODY-2 patients results from defective glucose utilisation in both the pancreas and liver [5]. Defective glucose utilisation in the pancreas of MODY-2 patients results in a raised threshold for glucose stimulated insulin secretion. Conversely, rare activating mutations of GLK reduce this threshold resulting in familial hyperinsulinism [6, 6a, 7]. In addition to the reduced GLK activity observed in MODY-2 diabetics, hepatic glucokinase activity is also decreased in type 2 diabetics [8]. Importantly, global or liver selective overexpression of GLK prevents or reverses the development of the diabetic phenotype in both dietary and genetic models of the disease [9-12]. Moreover, acute treatment of type 2 diabetics with fructose improves glucose tolerance through stimulation of hepatic glucose utilisation [1,3]. This effect is believed to be mediated through a fructose induced increase in cytosolic GLK activity in the hepatocyte by the mechanism described below [13].

Hepatic GLK activity is inhibited through association with GLK regulatory protein (GLKRP). The GLK/GLKRP complex is stabilised by fructose-6-phosphate (F6P) binding to the GLKRP and destabilised by displacement of this sugar phosphate by fructose-1-phosphate (F1P). F1P is generated by fructokinase mediated phosphorylation of dietary fructose. Consequently, GLK/GLKRP complex integrity and hepatic GLK activity is regulated in a nutritionally dependent manner as F6P is dominant in the post-absorptive state whereas F1P predominates in the post-prandial state. In contrast to the hepatocyte, the pancreatic β-cell expresses GLK in the absence of GLKRP. Therefore, β-cell GLK activity is regulated extensively by the availability of its substrate, glucose. Small molecules may activate GLK either directly or through destabilising the GLK/GLKRP complex. The former class of compounds are predicted to stimulate glucose utilisation in both the liver and the pancreas whereas the latter are predicted to act selectively in the liver. However, compounds with either profile are predicted to be of therapeutic benefit in treating Type 2 diabetes as this disease is characterised by defective glucose utilisation in both tissues.

GLK, GLKRP and the $K_{ATP}$ channel are expressed in neurones of the hypothalamus, a region of the brain that is important in the regulation of energy balance and the control of food intake [14-18]. These neurones have been shown to express orectic and anorectic neuropeptides [15, 19, 20] and have been assumed to be the glucose-sensing neurones within the hypothalamus that are either inhibited or excited by changes in ambient glucose concentrations [17, 19, 21, 22]. The ability of these neurones to sense changes in glucose levels is defective in a variety of genetic and experimentally induced models of obesity [23-28]. Intracerebroventricular (icv) infusion of glucose analogues, that are competitive inhibitors of glucokinase, stimulate food intake in lean rats [29, 30]. In contrast, icv infusion of glucose suppresses feeding [31]. Thus, small molecule activators of GLK may decrease food intake and weight gain through central effects on GLK. Therefore, GLK activators may be of therapeutic use in treating eating disorders, including obesity, in addition to diabetes. The hypothalamic effects will be additive or synergistic to the effects of the same compounds acting in the liver and/or pancreas in normalising glucose homeostasis, for the treatment of Type 2 diabetes. Thus the GLK/GLKRP system can be described as a potential "Diabesity" target (of benefit in both Diabetes and Obesity).

GLK is also expressed in specific entero-endocrine cells where it is believed to control the glucose sensitive secretion of the incretin peptides GIP (glucose-dependent insulinotropic polypeptide) and GLP-1 (Glucagon-Like Peptide-1) from gut K-cells and L-cells respectively (32, 33, 34). Therefore, small molecule activators of GLK may have additional beneficial effects on insulin secretion, b-cell function and survival and body weight as a consequence of stimulating GIP and GLP-1 secretion from these entero-endocrine cells.

In WO00/58293 and WO01/44216 (Roche), a series of benzylcarbamoyl compounds are described as glucokinase activators. The mechanism by which such compounds activate GLK is assessed by measuring the direct effect of such compounds in an assay in which GLK activity is linked to NADH production, which in turn is measured optically—see details of the in vitro assay described hereinafter. Compounds of the present invention may activate GLK directly or may activate GLK by inhibiting the interaction of GLKRP with GLK.

Further GLK activators have been described in WO03/095438 (substituted phenylacetamides, Roche), WO03/055482 (carboxamide and sulphonamide derivatives, Novo Nordisk), WO2004/002481 (arylcarbonyl derivatives, Novo Nordisk), and in WO03/080585 (amino-substituted benzoylaminoheterocycles, Banyu).

Our International application Number: WO03/000267 describes a group of benzoyl amino pyridyl carboxylic acids which are activators of the enzyme glucokinase (GLK).

Our International application Number: WO03/015774 describes compounds of the Formula (A):

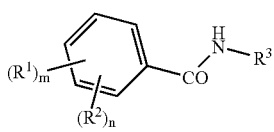

wherein R³ is a phenyl or a substituted heterocycle other than a carboxylic acid substituted pyridyl.

International application WO2004/076420 (Banyu) describes compounds which are generally a subset of those described in WO03/015774, wherein for example R¹ is an (substituted) alkyl ether and R² is (substituted) phenoxy.

We have surprisingly found a small group of compounds, generally a selected subgroup of those described in WO 03/015774, which have generally superior potency for the GLK enzyme, and more advantageous physical properties, including, for example, higher aqueous solubility, higher permeability, and/or lower plasma protein binding. Consequently, such compounds having a balance of these properties would be expected to display higher plasma free drug levels and superior in vivo efficacy after oral dosing as determined, for example, by activity in Oral Glucose Tolerance Tests (OGTTs) and/or glucose profile. Therefore this group of compounds would be expected to provide superior oral exposure at a lower dose and thereby be particularly suitable for use in the treatment or prevention of a disease or medical condition mediated through GLK. Furthermore, the compounds of the invention may have favourable metabolic profiles and/or toxicity profiles. The compounds of the invention may also have superior potency and/or advantageous physical properties (as described above) and/or favourable toxicity profiles and/or favourable metabolic profiles in comparison with other GLK activators known in the art, as well as those described in WO 03/015774.

Thus, according to the first aspect of the invention there is provided a compound of Formula (I):

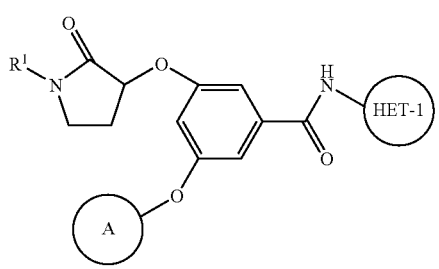

wherein:
$R^1$ is selected from (1-4C)alkyl and (3-6C)cycloalkyl;
HET-1 is a 5- or 6-membered, C-linked heteroaryl ring containing a nitrogen atom in the 2-position relative to the amide nitrogen to which the ring is attached and optionally 1 or 2 further ring heteroatoms independently selected from O, N and S; which ring is optionally substituted on any nitrogen atom (provided it is not thereby quaternised) by a substituent selected from $R^7$ and/or on 1 or 2 available carbon atoms by a substituent independently selected from $R^6$;
Ring A is selected from phenyl, HET-2 and HET-3; wherein when Ring A is phenyl it is substituted by $R^2$ and optionally further substituted by a group selected from $R^3$;

$R^2$ is selected from —C(O)NR⁴R⁵, SOpR⁴, and —SO₂NR⁴R⁵;
$R^3$ is selected from halo, methyl and trifluoromethyl;
$R^4$ is selected from hydrogen, (1-4C)alkyl [optionally substituted by 1 or 2 substituents independently selected from HET-5, —OR⁵, —SO₂R⁵, (3-6C)cycloalkyl (optionally substituted with 1 group selected from R¹⁵) and —C(O)NR⁵R⁵], (3-6C)cycloalkyl (optionally substituted with 1 group selected from R¹⁵) and HET-5;
HET-5 is a 4-, 5- or 6-membered, C- or N-linked heterocyclyl ring containing 1, 2, 3 or 4 heteroatoms independently selected from O, N and S, wherein a —CH₂— group can optionally be replaced by a —C(O)—, and wherein a sulphur atom in the heterocyclic ring may optionally be oxidised to a S(O) or S(O)₂ group; which ring is optionally substituted on an available carbon or nitrogen atom by 1 or 2 (1-4C)alkyl substituents;
$R^5$ is hydrogen or (1-4C)alkyl;
or
$R^4$ and $R^5$ together with the nitrogen atom to which they are attached form a 4 to 7 membered saturated or partially unsaturated heterocyclyl ring, optionally containing 1 or 2 further heteroatoms (in addition to the linking N atom) independently selected from O, N and S, wherein a —CH₂— group can optionally be replaced by a —C(O)— and wherein a sulphur atom in the ring may optionally be oxidised to a S(O) or S(O)₂ group; which ring is optionally substituted on an available carbon atom by 1 or 2 substituents independently selected from $R^8$ and/or on an available nitrogen atom by a substituent selected from $R^9$; or
$R^4$ and $R^5$ together with the nitrogen atom to which they are attached form a 6-10 membered bicyclic saturated or partially unsaturated heterocyclyl ring, optionally containing 1 further nitrogen atom (in addition to the linking N atom), wherein a —CH₂— group can optionally be replaced by a —C(O)—; which ring is optionally substituted on an available carbon by 1 substituent selected from hydroxy, methyl and halo, or on an available nitrogen atom by methyl;
$R^6$ is independently selected from (1-4C)alkyl, halo, hydroxy(1-4C)alkyl, (1-4C)alkoxy(1-4C)alkyl, (1-4C)alkylS(O)p(1-4C)alkyl, amino(1-4C)alkyl, (1-4C)alkylamino(1-4C)alkyl and di(1-4C)alkylamino(1-4C)alkyl;
$R^7$ is independently selected from (1-4C)alkyl, hydroxy(1-4C)alkyl, (1-4C)alkoxy(1-4C)alkyl, (1-4C)alkylS(O)p(1-4C)alkyl, amino(1-4C)alkyl, (1-4C)alkylamino(1-4C)alkyl and di(1-4C)alkylamino(1-4C)alkyl;
$R^8$ is selected from hydroxy, (1-4C)alkoxy, (1-4C)alkyl, aminocarbonyl, (1-4C)alkylaminocarbonyl, di(1-4C)alkylaminocarbonyl, (1-4C)alkylamino, di(1-4C)alkylamino, (1-4C)alkoxy(1-4C)alkyl, hydroxy(1-4C)alkyl and —S(O)p(1-4C)alkyl;
$R^9$ is selected from (1-4C)alkyl, —C(O)(1-4C)alkyl, aminocarbonyl, (1-4C)alkylaminocarbonyl, di(1-4C)alkylaminocarbonyl, (1-4C)alkoxy(1-4C)alkyl, hydroxy(1-4C)alkyl and —S(O)p(1-4C)alkyl;
HET-2 is a 5- or 6-membered heteroaryl ring, containing 1, 2 or 3 ring hetereoatoms independently selected from O, S and N; which ring is substituted on an available carbon atom by a substituent selected from $R^2$, and is optionally further substituted on 1 or 2 available carbon atoms by a substituent independently selected from $R^3$ and/or on an available nitrogen atom (provided it is not thereby quaternised) by a substituent selected from $R^{10}$;
$R^{10}$ is selected from (1-4C)alkyl, (3-6C)cycloalkyl, hydroxy(1-4C)alkyl, (1-4C)alkoxy(1-4C)alkyl, —C(O)(1-4C)alkyl, benzyl, and (1-4C)alkylsulfonyl;
HET-3 is a fused bicyclic ring system of formula —B—C;

wherein B is a Ring is directly attached to the linking oxygen atom and Ring B is phenyl or is a 5- or 6-membered heteroaryl ring containing 1, 2 or 3 heteroatoms independently selected from O, N and S (provided there are no O—O, S—S or O—S bonds in the ring);

wherein Ring B is optionally substituted on any nitrogen atom by a substituent selected from $R^{11}$ and/or on any available carbon atom by 1 or 2 substituents independently selected from $R^{12}$;

$R^{11}$ is independently selected from (1-4C)alkyl, hydroxy(1-4C)alkyl, (1-4C)alkoxy(1-4C)alkyl, (1-4C)alkylS(O)p(1-4C)alkyl, amino(1-4C)alkyl, (1-4C)alkylamino(1-4C)alkyl, di(1-4C)alkylamino(1-4C)alkyl and HET-4;

$R^{12}$ is independently selected from (1-4C)alkyl, halo, hydroxy(1-4C)alkyl, (1-4C)alkoxy(1-4C)alkyl, (1-4C)alkylS(O)p(1-4C)alkyl, amino(1-4C)alkyl, (1-4C)alkylamino(1-4C)alkyl, di(1-4C)alkylamino(1-4C)alkyl and HET-4;

HET-4 is a 5- or 6-membered, C- or N-linked unsubstituted heteroaryl ring containing 1, 2 or 3 ring heteroatoms independently selected from O, N and S;

Ring C is a 5-7 membered heterocyclic ring fused to Ring B, containing 1, 2 or 3 ring heteroatoms independently selected from O, S and N (provided that there are no O—O, S—O or S—S bonds within the ring), wherein any ring carbon or sulfur atom may optionally be oxidised and wherein Ring C is optionally substituted on any nitrogen atom by a substituent selected from $R^{13}$ and/or on any available carbon atom by 1 or 2 substituents independently selected from $R^{14}$;

$R^{13}$ is selected from (1-4C)alkyl, (3-6C)cycloalkyl, benzyl, (1-4C)alkylcarbonyl, (1-4C)alkylsulphonyl, hydroxy(1-4C)alkyl and (1-4C)alkoxy(1-4C)alkyl;

$R^{14}$ is selected from (1-4C)alkyl, (3-6C)cycloalkyl, (1-4C)alkoxy, hydroxy, fluoro and chloro;

$R^{15}$ is independently selected from (1-4C)alkyl, hydroxy(1-4C)alkyl and hydroxy;

n is 0 or 1;

p is (independently at each occurrence) 0, 1 or 2;

or a salt thereof.

In another aspect of the invention there is provided a compound of Formula (II):

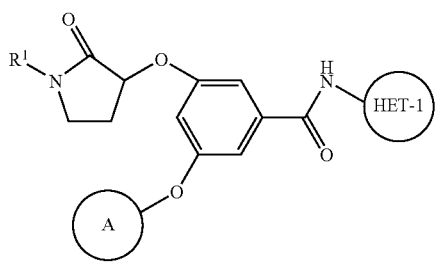

(II)

wherein:

$R^1$ is selected from (1-4C)alkyl and (3-6C)cycloalkyl;

HET-1 is a 5- or 6-membered, C-linked heteroaryl ring containing a nitrogen atom in the 2-position relative to the amide nitrogen to which the ring is attached and optionally 1 or 2 further ring heteroatoms independently selected from O, N and S; which ring is optionally substituted on any nitrogen atom (provided it is not thereby quaternised) by a substituent selected from $R^7$ and/or on 1 or 2 available carbon atoms by a substituent independently selected from $R^6$;

Ring A is phenyl, substituted by $R^2$ and optionally further substituted by a group selected from $R^3$;

$R^2$ is selected from —C(O)$NR^4R^5$, $SOpR^4$, and —$SO_2NR^4R^5$;

$R^3$ is selected from halo, methyl and trifluoromethyl;

$R^4$ is selected from hydrogen, (1-4C)alkyl [optionally substituted by 1 or 2 substituents independently selected from HET-5, —$OR^5$, —$SO_2R^5$, (3-6C)cycloalkyl (optionally substituted with 1 group selected from $R^{15}$) and —C(O)$NR^5R^5$], (3-6C)cycloalkyl (optionally substituted with 1 group selected from $R^{15}$) and HET-5;

HET-5 is a 4-, 5- or 6-membered, C- or N-linked heterocyclyl ring containing 1, 2, 3 or 4 heteroatoms independently selected from O, N and S, wherein a —$CH_2$— group can optionally be replaced by a —C(O)—, and wherein a sulphur atom in the heterocyclic ring may optionally be oxidised to a S(O) or S(O)$_2$ group; which ring is optionally substituted on an available carbon or nitrogen atom by 1 or 2 (1-4C)alkyl substituents;

$R^5$ is hydrogen or (1-4C)alkyl;

or $R^4$ and $R^5$ together with the nitrogen atom to which they are attached form a 4 to 7 membered saturated or partially unsaturated heterocyclyl ring, optionally containing 1 or 2 further heteroatoms (in addition to the linking N atom) independently selected from O, N and S, wherein a —$CH_2$— group can optionally be replaced by a —C(O)— and wherein a sulphur atom in the ring may optionally be oxidised to a S(O) or S(O)$_2$ group; which ring is optionally substituted on an available carbon atom by 1 or 2 substituents independently selected from $R^8$ and/or on an available nitrogen atom by a substituent selected from $R^9$; or $R^4$ and $R^5$ together with the nitrogen atom to which they are attached form a 6-10 membered bicyclic saturated or partially unsaturated heterocyclyl ring, optionally containing 1 further nitrogen atom (in addition to the linking N atom), wherein a —$CH_2$— group can optionally be replaced by a —C(O)—; which ring is optionally substituted on an available carbon by 1 substituent selected from hydroxy, methyl and halo, or on an available nitrogen atom by methyl;

$R^6$ is independently selected from (1-4C)alkyl, halo, hydroxy(1-4C)alkyl, (1-4C)alkoxy(1-4C)alkyl, (1-4C)alkylS(O)p(1-4C)alkyl, amino(1-4C)alkyl, (1-4C)alkylamino(1-4C)alkyl and di(1-4C)alkylamino(1-4C)alkyl;

$R^7$ is independently selected from (1-4C)alkyl, hydroxy(1-4C)alkyl, (1-4C)alkoxy(1-4C)alkyl, (1-4C)alkylS(O)p(1-4C)alkyl, amino(1-4C)alkyl, (1-4C)alkylamino(1-4C)alkyl and di(1-4C)alkylamino(1-4C)alkyl;

$R^8$ is selected from hydroxy, (1-4C)alkoxy, (1-4C)alkyl, aminocarbonyl, (1-4C)alkylaminocarbonyl, di(1-4C)alkylaminocarbonyl, (1-4C)alkylamino, di(1-4C)alkylamino, (1-4C)alkoxy(1-4C)alkyl, hydroxy(1-4C)alkyl and —S(O)p(1-4C)alkyl;

$R^9$ is selected from (1-4C)alkyl, —C(O)(1-4C)alkyl, aminocarbonyl, (1-4C)alkylaminocarbonyl, di(1-4C)alkylaminocarbonyl, (1-4C)alkoxy(1-4C)alkyl, hydroxy(1-4C)alkyl and —S(O)p(1-4C)alkyl;

$R^{15}$ is independently selected from (1-4C)alkyl, hydroxy(1-4C)alkyl and hydroxy;

n is 0 or 1;

p is (independently at each occurrence) 0, 1 or 2;

or a salt thereof.

In another aspect of the invention there is provided a compound of Formula (III):

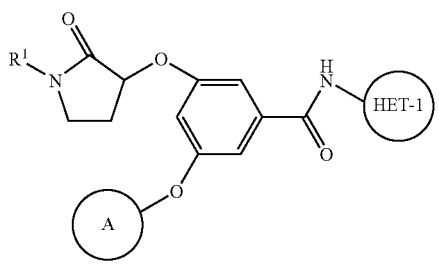

(III)

wherein:
R¹ is selected from (1-4C)alkyl and (3-6C)cycloalkyl;
HET-1 is a 5- or 6-membered, C-linked heteroaryl ring containing a nitrogen atom in the 2-position relative to the amide nitrogen to which the ring is attached and optionally 1 or 2 further ring heteroatoms independently selected from O, N and S; which ring is optionally substituted on any nitrogen atom (provided it is not thereby quaternised) by a substituent selected from $R^7$ and/or on 1 or 2 available carbon atoms by a substituent independently selected from $R^6$;
Ring A is HET-2;
HET-2 is a 5- or 6-membered heteroaryl ring, containing 1, 2 or 3 ring hetereoatoms independently selected from O, S and N; which ring is substituted on an available carbon atom by a substituent selected from $R^2$, and is optionally further substituted on 1 or 2 available carbon atoms by a substituent independently selected from $R^3$ and/or on an available nitrogen atom (provided it is not thereby quaternised) by a substituent selected from $R^{10}$;
$R^2$ is selected from —C(O)NR⁴R⁵, SOpR⁴, and —SO₂NR⁴R⁵;
$R^3$ is selected from halo, methyl and trifluoromethyl;
$R^4$ is selected from hydrogen, (1-4C)alkyl [optionally substituted by 1 or 2 substituents independently selected from HET-5, —OR⁵, —SO₂R⁵, (3-6C)cycloalkyl (optionally substituted with 1 group selected from $R^{15}$) and —C(O)NR⁵R⁵], (3-6C)cycloalkyl (optionally substituted with 1 group selected from $R^{15}$) and HET-5;
HET-5 is a 4-, 5- or 6-membered, C- or N-linked heterocyclyl ring containing 1, 2, 3 or 4 heteroatoms independently selected from O, N and S, wherein a —CH₂— group can optionally be replaced by a —C(O)—, and wherein a sulphur atom in the heterocyclic ring may optionally be oxidised to a S(O) or S(O)₂ group; which ring is optionally substituted on an available carbon or nitrogen atom by 1 or 2 (1-4C)alkyl substituents;
$R^5$ is hydrogen or (1-4C)alkyl;
or
$R^4$ and $R^5$ together with the nitrogen atom to which they are attached form a 4 to 7 membered saturated or partially unsaturated heterocyclyl ring, optionally containing 1 or 2 further heteroatoms (in addition to the linking N atom) independently selected from O, N and S, wherein a —CH₂— group can optionally be replaced by a —C(O)— and wherein a sulphur atom in the ring may optionally be oxidised to a S(O) or S(O)₂ group; which ring is optionally substituted on an available carbon atom by 1 or 2 substituents independently selected from $R^8$ and/or on an available nitrogen atom by a substituent selected from $R^9$; or
$R^4$ and $R^5$ together with the nitrogen atom to which they are attached form a 6-10 membered bicyclic saturated or partially unsaturated heterocyclyl ring, optionally containing 1 further nitrogen atom (in addition to the linking N atom), wherein a —CH₂— group can optionally be replaced by a —C(O)—; which ring is optionally substituted on an available carbon by 1 substituent selected from hydroxy, methyl and halo, or on an available nitrogen atom by methyl;
$R^6$ is independently selected from (1-4C)alkyl, halo, hydroxy(1-4C)alkyl, (1-4C)alkoxy(1-4C)alkyl, (1-4C)alkylS(O)p(1-4C)alkyl, amino(1-4C)alkyl, (1-4C)alkylamino(1-4C)alkyl and di(1-4C)alkylamino(1-4C)alkyl;
$R^7$ is independently selected from (1-4C)alkyl, hydroxy(1-4C)alkyl, (1-4C)alkoxy(1-4C)alkyl, (1-4C)alkylS(O)p(1-4C)alkyl, amino(1-4C)alkyl, (1-4C)alkylamino(1-4C)alkyl and di(1-4C)alkylamino(1-4C)alkyl;
$R^8$ is selected from hydroxy, (1-4C)alkoxy, (1-4C)alkyl, aminocarbonyl, (1-4C)alkylaminocarbonyl, di(1-4C)alkylaminocarbonyl, (1-4C)alkylamino, di(1-4C)alkylamino, (1-4C)alkoxy(1-4C)alkyl, hydroxy(1-4C)alkyl and —S(O)p(1-4C)alkyl;
$R^9$ is selected from (1-4C)alkyl, —C(O)(1-4C)alkyl, aminocarbonyl, (1-4C)alkylaminocarbonyl, di(1-4C)alkylaminocarbonyl, (1-4C)alkoxy(1-4C)alkyl, hydroxy(1-4C)alkyl and —S(O)p(1-4C)alkyl;
$R^{10}$ is selected from (1-4C)alkyl, (3-6C)cycloalkyl, hydroxy(1-4C)alkyl, (1-4C)alkoxy(1-4C)alkyl, —C(O)(1-4C)alkyl, benzyl, and (1-4C)alkylsulfonyl;
$R^{15}$ is independently selected from (1-4C)alkyl, hydroxy(1-4C)alkyl and hydroxy;
n is 0 or 1;
p is (independently at each occurrence) 0, 1 or 2;
or a salt thereof.

In another aspect of the invention there is provided a compound of Formula (IV):

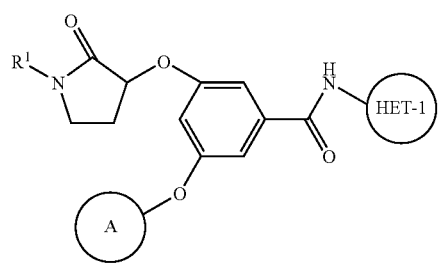

(IV)

wherein:
R¹ is selected from (1-4C)alkyl and (3-6C)cycloalkyl;
HET-1 is a 5- or 6-membered, C-linked heteroaryl ring containing a nitrogen atom in the 2-position relative to the amide nitrogen to which the ring is attached and optionally 1 or 2 further ring heteroatoms independently selected from O, N and S; which ring is optionally substituted on any nitrogen atom (provided it is not thereby quaternised) by a substituent selected from $R^7$ and/or on 1 or 2 available carbon atoms by a substituent independently selected from $R^6$;
$R^6$ is independently selected from (1-4C)alkyl, halo, hydroxy(1-4C)alkyl, (1-4C)alkoxy(1-4C)alkyl, (1-4C)alkylS(O)p(1-4C)alkyl, amino(1-4C)alkyl, (1-4C)alkylamino(1-4C)alkyl and di(1-4C)alkylamino(1-4C)alkyl;
$R^7$ is independently selected from (1-4C)alkyl, hydroxy(1-4C)alkyl, (1-4C)alkoxy(1-4C)alkyl, (1-4C)alkylS(O)p(1-4C)alkyl, amino(1-4C)alkyl, (1-4C)alkylamino(1-4C)alkyl and di(1-4C)alkylamino(1-4C)alkyl;
Ring A is HET-3;
HET-3 is a fused bicyclic ring system of formula —B—C;

wherein B is a ring directly attached to the linking oxygen atom and Ring B is phenyl or is a 5- or 6-membered heteroaryl ring containing 1, 2 or 3 heteroatoms independently selected from O, N and S (provided there are no O—O, S—S or O—S bonds in the ring);

wherein Ring B is optionally substituted on any nitrogen atom by a substituent selected from $R^{11}$ and/or on any available carbon atom by 1 or 2 substituents independently selected from $R^{12}$;

$R^{11}$ is independently selected from (1-4C)alkyl, hydroxy(1-4C)alkyl, (1-4C)alkoxy(1-4C)alkyl, (1-4C)alkylS(O)p(1-4C)alkyl, amino(1-4C)alkyl, (1-4C)alkylamino(1-4C) alkyl, di(1-4C)alkylamino(1-4C)alkyl and HET-4;

$R^{12}$ is independently selected from (1-4C)alkyl, halo, hydroxy(1-4C)alkyl, (1-4C)alkoxy(1-4C)alkyl, (1-4C) alkylS(O)p(1-4C)alkyl, amino(1-4C)alkyl, (1-4C)alkylamino(1-4C)alkyl, di(1-4C)alkylamino(1-4C)alkyl and HET-4;

HET-4 is a 5- or 6-membered, C- or N-linked unsubstituted heteroaryl ring containing 1, 2 or 3 ring heteroatoms independently selected from O, N and S;

Ring C is a 5-7 membered heterocyclic ring fused to Ring B, containing 1, 2 or 3 ring hetereoatoms independently selected from O, S and N (provided that there are no O—O, S—O or S—S bonds within the ring), wherein any ring carbon or sulfur atom may optionally be oxidised and wherein Ring C is optionally substituted on any nitrogen atom by a substituent selected from $R^{13}$ and/or on any available carbon atom by 1 or 2 substituents independently selected from $R^{14}$;

$R^{13}$ is selected from (1-4C)alkyl, (3-6C)cycloalkyl, benzyl, (1-4C)alkylcarbonyl, (1-4C)alkylsulphonyl, hydroxy(1-4C)alkyl and (1-4C)alkoxy(1-4C)alkyl;

$R^{14}$ is selected from (1-4C)alkyl, (3-6C)cycloalkyl, (1-4C) alkoxy, hydroxy, fluoro and chloro;

n is 0 or 1;

p is (independently at each occurrence) 0, 1 or 2;

or a salt thereof.

Reference hereinafter to a compound of formula (I) should be understood to apply equally to compounds of formula (II), (III) or (IV), even where not explicitly stated.

It will be appreciated that, where the definition of heterocyclyl group HET-1 encompass heteroaryl rings which may be substituted on nitrogen, such substitution may not result in charged quaternary nitrogen atoms, removal of aromaticity of the ring or unstable structures. It will be appreciated that the definition of HET-1 is not intended to include any O—O, O—S or S—S bonds. It will be appreciated that the definition of HET-1 is not intended to include unstable structures.

It will be understood that any single carbon atom in HET-1 may only be substituted by one group $R^6$ in order to maintain aromaticity of the ring. Up to two different carbon atoms in a HET-1 ring may be substituted by an $R^6$ group, each of which may be the same or different, provided the structure thereby formed is stable and aromatic.

It will be understood that $R^8$ can be present on any or all available carbon atoms in the heterocyclic ring formed by $NR^4R^5$; each carbon atom can be substituted with 1 or 2 $R^8$ groups which may be the same or different, provided the structure thereby formed is stable (so, for example, it is not intended to cover gem-dihydroxy substitution).

It will be understood that where a compound of the formula (I) contains more than one group $R^5$, they may be the same or different.

It will be understood that where a compound of the formula (I) contains more than one group $R^3$, they may be the same or different.

A similar convention applies for all other groups and substituents on a compound of formula (I) as hereinbefore defined.

Compounds of Formula (I) may form salts which are within the ambit of the invention. Pharmaceutically acceptable salts are preferred although other salts may be useful in, for example, isolating or purifying compounds.

In another aspect, the invention relates to compounds of formula (I) as hereinabove defined or to a pharmaceutically acceptable salt.

In another aspect, the invention relates to compounds of formula (I) as hereinabove defined or to a pro-drug thereof. Suitable examples of pro-drugs of compounds of formula (I) are in-vivo hydrolysable esters of compounds of formula (I). Therefore in another aspect, the invention relates to compounds of formula (I) as hereinabove defined or to an in-vivo hydrolysable ester thereof.

In this specification the generic term "alkyl" includes both straight-chain and branched-chain alkyl groups. However references to individual alkyl groups such as "propyl" are specific for the straight chain version only and references to individual branched-chain alkyl groups such as t-butyl are specific for the branched chain version only. For example, "(1-4C)alkyl" includes methyl, ethyl, propyl, isopropyl and t-butyl. An analogous convention applies to other generic terms.

For the avoidance of doubt, reference to the group HET-1 containing a nitrogen in the 2-position, is intended to refer to the 2-position relative to the amide nitrogen atom to which the group is attached. For example, HET-1 encompasses but is not limited to the heterocycles shown in the following structures:

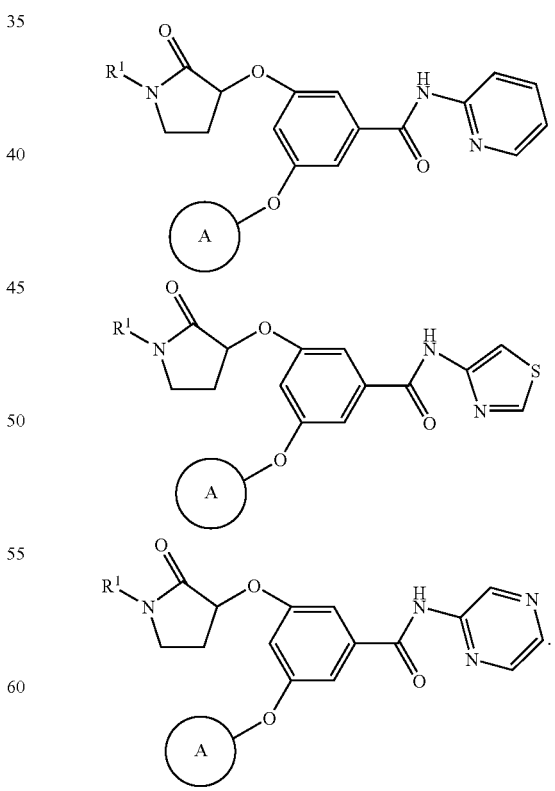

Suitable examples of HET-1 as a 5- or 6-membered, C-linked heteroaryl ring as hereinbefore defined, include thiazolyl, isothiazolyl, thiadiazolyl, pyridyl, pyrazinyl, pyridazinyl, pyrazolyl, imidazolyl, pyrimidinyl, oxazolyl, isoxazolyl, oxadiazolyl and triazolyl.

Suitable examples of HET-2 include thienyl, furyl, thiazolyl, isothiazolyl, thiadiazolyl, pyridyl, pyrazinyl, pyridazinyl, pyrazolyl, imidazolyl, pyrimidinyl, oxazolyl, isoxazolyl, oxadiazolyl and triazolyl. Further suitable examples of HET-2 include aromatic heterocycles where a ring nitrogen or sulfur atom has been oxidised but aromaticity has been preserved, for example a pyridine N-oxide. Further suitable examples of HET-2 include thiazolyl, pyridyl, pyrazinyl, pyridazinyl and pyrimidinyl.

Suitable examples for a 4-7 membered ring formed by $R^4$ and $R^5$ together with the nitrogen to which they are attached, as hereinbefore defined, include morpholino, thiomorpholino (and versions thereof wherein the sulfur is oxidised to an SO or $S(O)_2$ group), piperidinyl, piperazinyl, pyrrolidinyl, azetidinyl, homopiperazinyl, homo-morpholino, homo-thiomorpholino (and versions thereof wherein the sulfur is oxidised to an SO or $S(O)_2$ group) and homo-piperidinyl.

Suitable examples for a 6-10 membered bicyclic heterocyclic ring formed by $R^4$ and $R^5$ together with the nitrogen to which they are attached, as hereinbefore defined, are bicyclic saturated or partially unsaturated heterocyclyl ring such as those illustrated by the structures shown below (wherein the dotted line indicates the point of attachment to the rest of the molecule and wherein R represents the optional substituents on carbon or nitrogen defined hereinbefore):

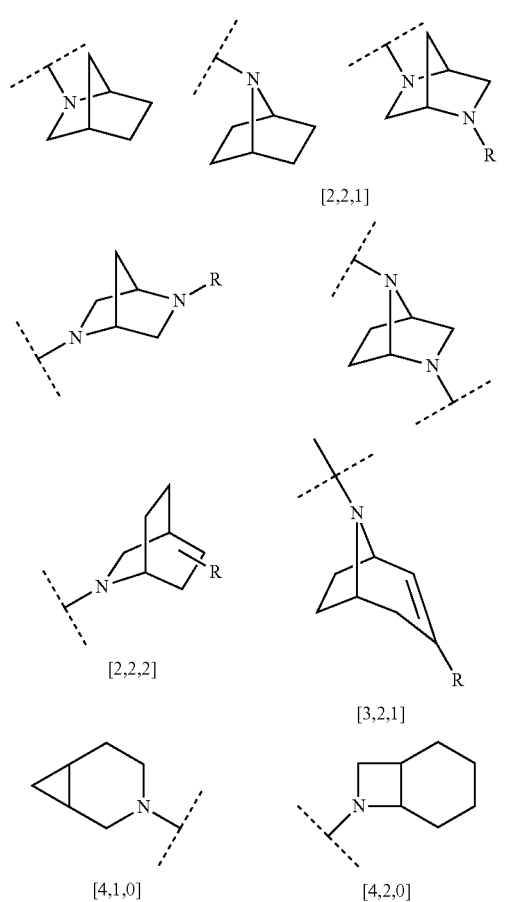

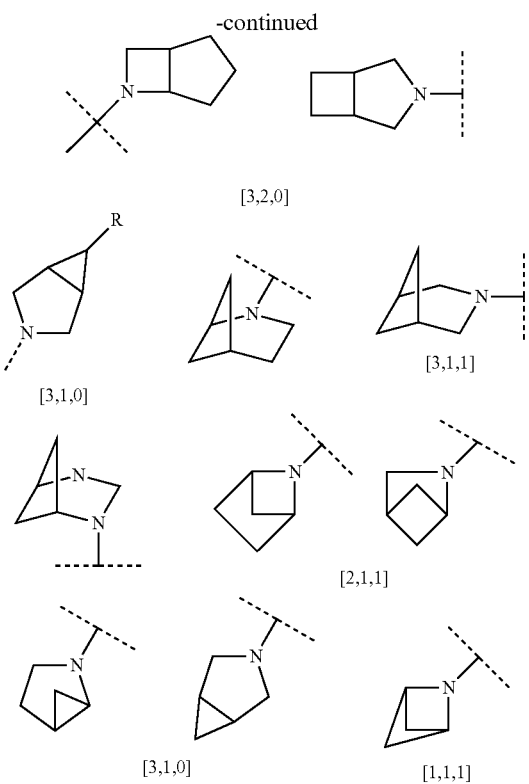

In particular such a ring system is a [2.2.1] system such as

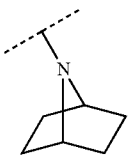

(7-azabicyclo[2.2.1]hept-7-yl).

In another embodiment, such a ring system is a [2.1.1] system such as

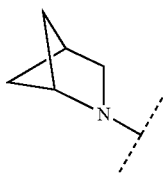

(2-azabicyclo[2.1.1]hex-2-yl).

Suitable values for the bicyclic system HET-3 formed by ring B fused to Ring C include those where Ring C is pyridyl, pyrazinyl, pyrimidinyl, piperidinyl, piperazinyl, homopiperazinyl, morpholinyl, homomorpholinyl, thiomorpholinyl, homothiomorpholinyl, oxathianyl, homooxathianyl, furyl, thienyl, pyrrolyl, pyrrolidinyl, 1,3-dioxolanyl, oxazolyl, thiazolyl, imidazolyl, imidazolidinyl, pyrazolyl, isoxazolyl, isothiazolyl, pyranyl, 1,4-dioxolanyl, dihydrothienyl, dihydrofuryl and oxathiazepinyl. Further suitable values include those wherein Ring C is oxathiazepinyl, dihydrothienyl, dihydrofuryl, and piperidinyl.

Further suitable values include such ring systems where one or more carbon atoms in Ring C have been oxidised to a carbonyl group, and/or where one or more sulfur atoms in Ring C have been oxidised to an S(O) or S(O)₂ group.

Suitable values for Ring B as a 5- or 6-membered heterocyclyl ring are furyl, thienyl, pyrrolyl, pyrrolidinyl, oxazolyl, thiazolyl, imidazolyl, pyrazolyl, isoxazolyl, isothiazolyl, pyridyl, pyrazinyl, pyrimidinyl and pyridazinyl. Further suitable values for Ring B are thiazolyl, pyridyl, pyrazinyl, pyrimidinyl and pyridazinyl. Still further suitable values for Ring B are thiazolyl and pyridyl. In another aspect Ring B is phenyl.

For example, HET-3 may suitably be selected from the structures below (which may optionally be substituted as hereinbefore defined):

-continued

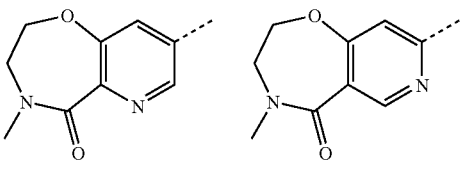

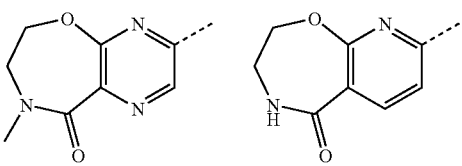

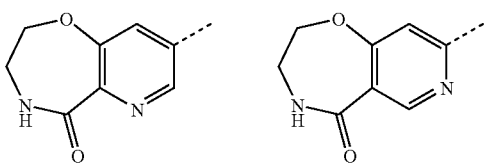

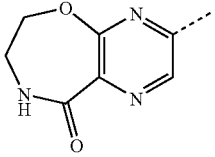

In a further aspect, suitable values for HET-3 are ring systems where Ring C is a 7-membered ring, for example:

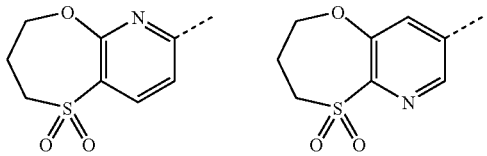

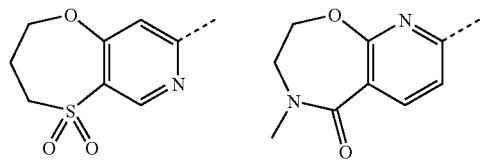

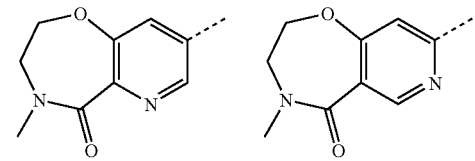

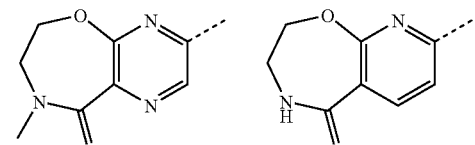

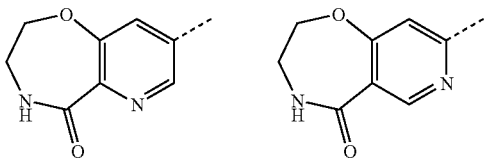

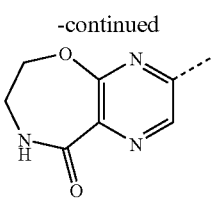

Further suitable values for HET-3 include the following formulae A to F, wherein each $R^{12a}$ is independently hydrogen or is $R^{12}$ as hereinbefore defined, each $R^{13a}$ is independently hydrogen or is $R^{13}$ as hereinbefore defined, each $R^{14a}$ is independently hydrogen or is $R^{14}$ as hereinbefore defined:

A

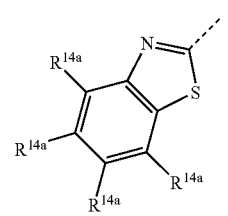

B

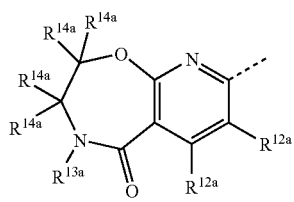

C

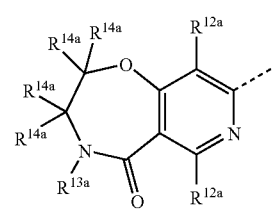

D

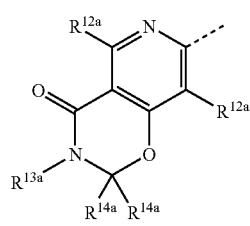

E

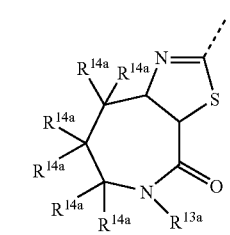

F

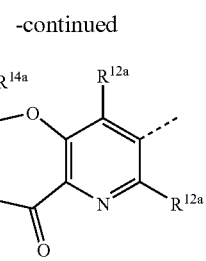

Further suitable values for HET-3 include formulae G to P as follows:

H

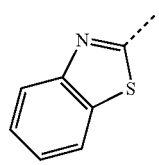

J

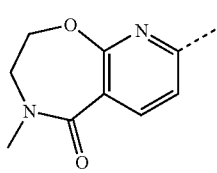

K

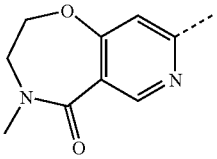

L

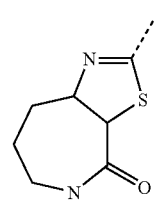

M

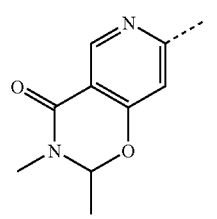

N

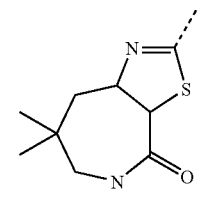

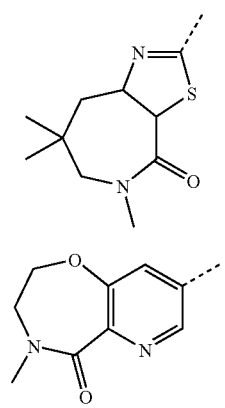

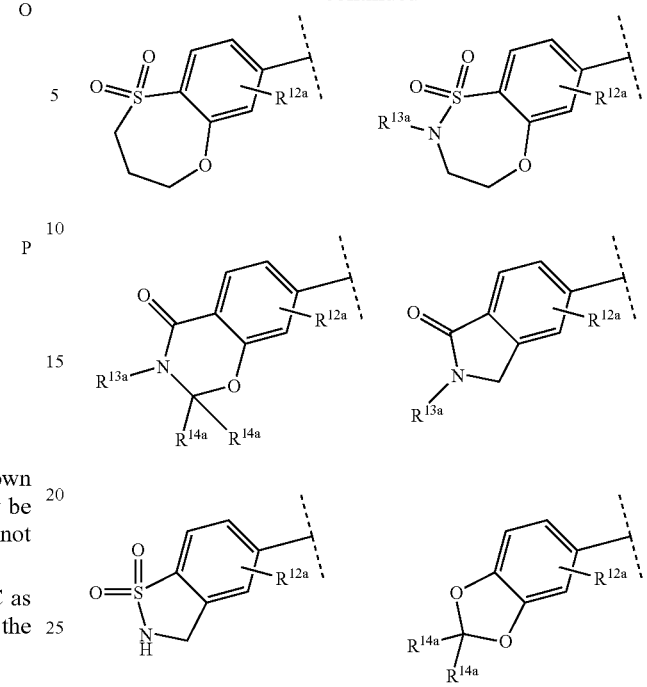

It will be appreciated that the bicyclic ring systems shown above are to illustrate the definitions of Ring C and may be applied to any of the possible values for Ring B, even if not shown above.

It will be understood that references herein to Ring C as 1,3-dioxolyl are intended to refer to structures such as the following (illustrated with Ring B is phenyl):

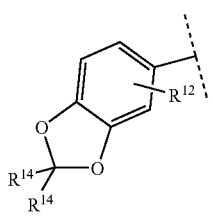

It will be understood that references herein to Ring C as 1,4-dioxolanyl are intended to refer to structures such as the following (illustrated with Ring B is phenyl):

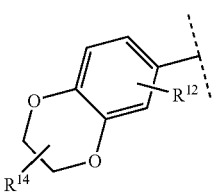

For example suitable values for the bicyclic system formed by Ring C fused to Ring B as phenyl include the following (wherein each $R^{13a}$ is hydrogen or is selected from $R^{13}$ as hereinbefore defined, $R^{14a}$ is hydrogen or is selected from $R^{14}$ as hereinbefore defined and each $R^{12a}$ is hydrogen or is $R^{12}$ as hereinbefore defined):

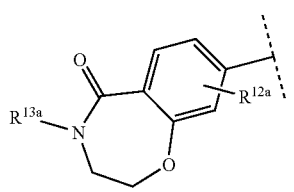

In another aspect, the bicyclic system formed by Ring C fused to Ring B as phenyl is selected from formulae AA to MM (wherein $R^{12a}$ is hydrogen or is selected from $R^{12}$ as hereinbefore defined, $R^{13a}$ is hydrogen or is selected from $R^{13}$ as hereinbefore defined and each $R^{14a}$ is hydrogen or $R^{14}$ as hereinbefore defined):

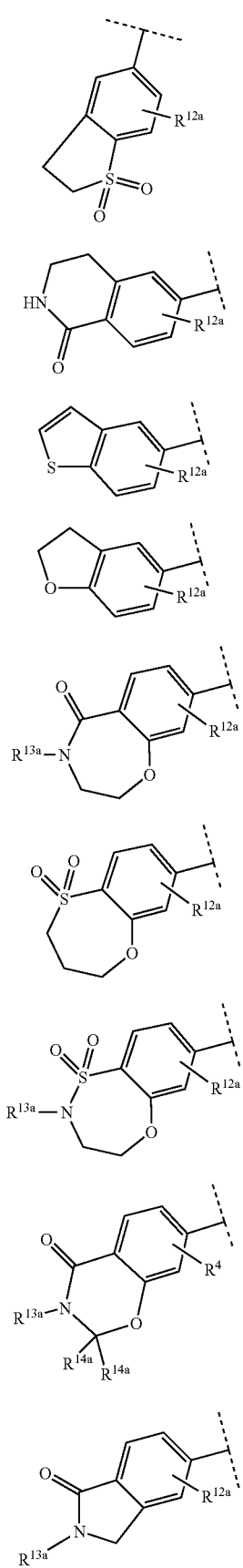

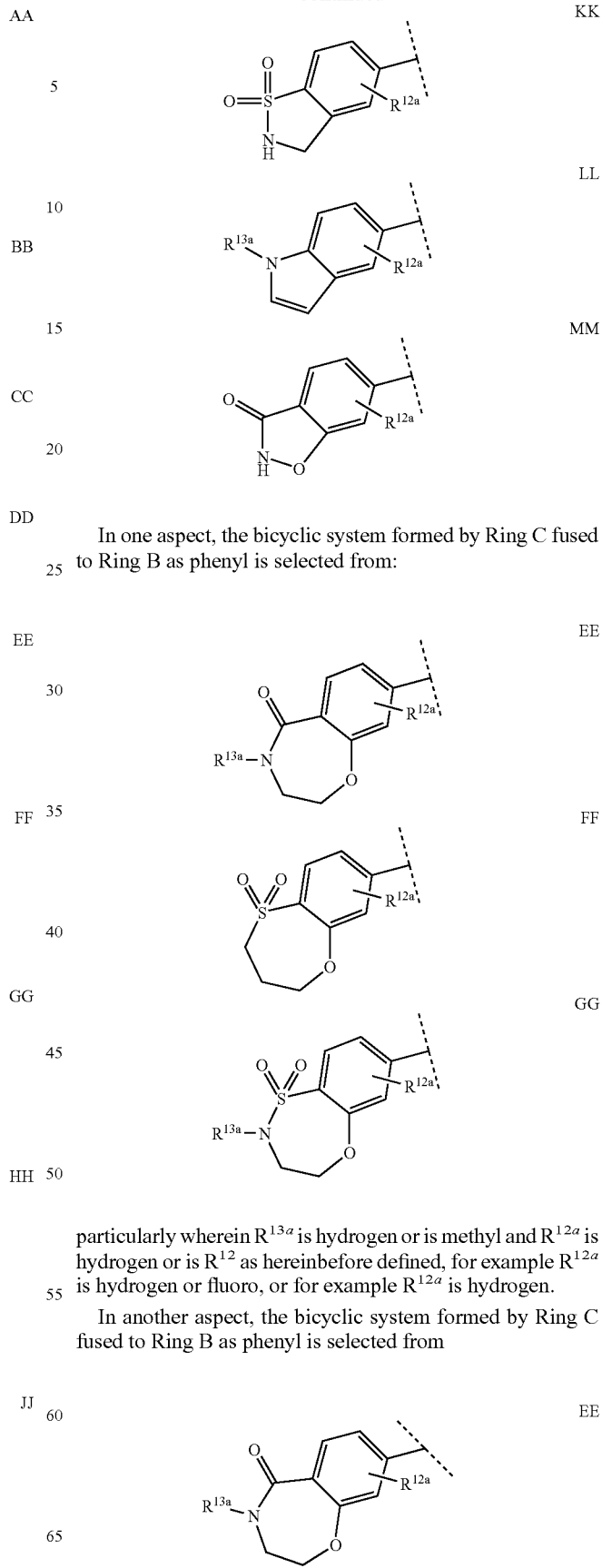

In one aspect, the bicyclic system formed by Ring C fused to Ring B as phenyl is selected from:

particularly wherein $R^{13a}$ is hydrogen or is methyl and $R^{12a}$ is hydrogen or is $R^{12}$ as hereinbefore defined, for example $R^{12a}$ is hydrogen or fluoro, or for example $R^{12a}$ is hydrogen.

In another aspect, the bicyclic system formed by Ring C fused to Ring B as phenyl is selected from

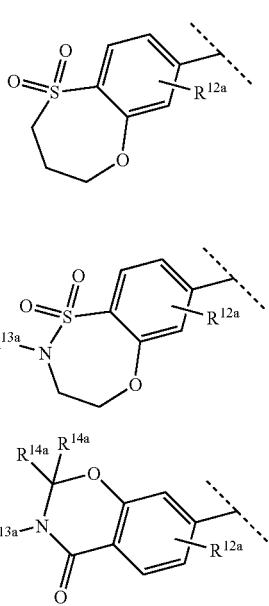

particularly, wherein both $R^{14a}$ are hydrogen, $R^{13a}$ is hydrogen or is methyl and $R^{12a}$ is hydrogen or is $R^{12}$ as hereinbefore defined, for example $R^{12a}$ is hydrogen or fluoro, or for example $R^{12a}$ is hydrogen. In one embodiment of this aspect, the bicyclic system formed by Ring C fused to Ring B as phenyl is of formula EE. In another embodiment of this aspect, the bicyclic system formed by Ring C fused to Ring B as phenyl is of formula FF. In another embodiment of this aspect, the bicyclic system formed by Ring C fused to Ring B as phenyl is of formula GG. In another embodiment of this aspect, the bicyclic system formed by Ring C fused to Ring B as phenyl is of formula HH.

In another aspect, the bicyclic system formed by Ring C fused to Ring B as phenyl is of formula (Z):

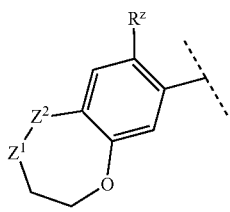

wherein $R^z$ is hydrogen or fluoro, $Z^1$ is $CH_2$ or $NR^{13a}$, $R^{13a}$ is hydrogen or methyl, and $Z^2$ is $C(=O)$ or $SO_2$.

In a further aspect, Ring C is an optionally substituted 5-7 membered heterocyclic ring fused to the benzene ring, containing 1, 2 or 3 ring hetereoatoms independently selected from O, S and N (provided that there are no O—O, S—O or S—S bonds within the ring), wherein any ring carbon or sulfur atom may optionally be oxidised, provided that where Ring C contains two ring heteroatoms they are not both oxygen (such that for example, Ring C is not dioxolyl or dioxolanyl).

Suitable examples of HET-4 include thiazolyl, isothiazolyl, thiadiazolyl, pyridyl, pyrazinyl, pyridazinyl, pyrazolyl, imidazolyl, pyrimidinyl, oxazolyl, isoxazolyl, oxadiazolyl and triazolyl.

It will be understood that HET-5 can be a saturated, or partially or fully unsaturated ring.

Suitable examples of HET-5 include azetidinyl, furyl, thienyl, thiazolyl, isothiazolyl, thiadiazolyl, pyridyl, pyrazinyl, pyridazinyl, pyrazolyl, imidazolyl, pyrimidinyl, oxazolyl, isoxazolyl, oxadiazolyl, morpholino, morpholinyl, piperidinyl, piperazinyl, morpholinyl, thiomorpholinyl, pyrrolyl, pyrrolidinyl, pyrrolidonyl, 2,5-dioxopyrrolidinyl, 1,1-dioxotetrahydrothienyl, 2-oxoimidazolidinyl, 2,4-dioxoimidazolidinyl, 2-oxo-1,3,4-(4-triazolinyl), 2-oxazolidinonyl, 2-oxotetrahydrofuranyl, tetrahydrofuranyl, tetrahydropyranyl, 1,1-dioxothiomorpholino, 1,3-dioxolanyl, 1,2,4-triazolyl, 1,2,3-triazolyl, pyranyl, and 4-pyridonyl.

It will be understood that HET-5 may be linked by any appropriate available C or N atom, therefore for example, for HET-5 as "imidazolyl" includes 1-, 2-, 4- and 5-imidazolyl.

Examples of (1-4C)alkyl include methyl, ethyl, propyl, isopropyl, butyl and tert-butyl; examples of (3-6C)cycloalkyl include cyclopropyl, cyclobutyl, cyclopentyl and cyclohexyl; examples of halo include fluoro, chloro, bromo and iodo; examples of hydroxy(1-4C)alkyl include hydroxymethyl, 1-hydroxyethyl, 2-hydroxyethyl, 2-hydroxypropyl, 3-hydroxypropyl, 1-hydroxyisopropyl and 4-hydroxybutyl; examples of (1-4C)alkoxy(1-4C)alkyl include methoxymethyl, ethoxymethyl, tert-butoxymethyl, 2-methoxyethyl, 2-ethoxyethyl, methoxypropyl, 2-methoxypropyl and methoxybutyl; example of (1-4C)alkoxy include methoxy, ethoxy, propoxy, isopropxy, butoxy and tert-butoxy; examples of (1-4C)alkylS(O)p (1-4C)alkyl (where p is 0, 1 or 2) include methylsulfinylmethyl, ethylsulfinylmethyl, ethylsulfinylethyl, methylsulfinylpropyl, methylsulfinylbutyl, methylsulfonylmethyl, ethylsulfonylmethyl, ethylsulfonylethyl, methylsulfonylpropyl, methylsulfonylbutyl, methylthiomethyl, ethylthiomethyl, ethylthioethyl, methylthiopropyl, and methylthiobutyl; examples of (1-4C)alkylsulfonyl include methylsulfonyl, ethylsulfonyl, propylsulfonyl, isopropylsulfonyl and tert-butylsulfonyl; examples of —S(O)p(1-4C)alkyl include (1-4C)alkylsulfonyl, methylsulfinyl, ethylsulfinyl, propylsulfinyl, isopropylsulfinyl, tert-butylsulfinyl, methylthio, ethylthio, propylthio, isopropylthio and tert-butylthio; examples of amino(1-4C)alkyl include aminomethyl, aminoethyl, 2-aminopropyl, 3-aminopropyl, 1-aminoisopropyl and 4-aminobutyl; examples of (1-4C)alkylamino(1-4C)alkyl include (N-methyl)aminomethyl, (N-ethyl)aminomethyl, 1-((N-methyl)amino)ethyl, 2-((N-methyl)amino)ethyl, (N-ethyl)aminoethyl, (N-methyl)aminopropyl, and 4-((N-methyl)amino)butyl; examples of di(1-4C)alkylamino(1-4C) alkyl include dimethylaminomethyl, methyl(ethyl)aminomethyl, methyl(ethyl)aminoethyl, (N,N-diethyl)aminoethyl, (N,N-dimethyl)aminopropyl and (N,N-dimethyl)aminobutyl; examples of —C(O)(1-4C)alkyl and (1-4C)alkylcarbonyl include methylcarbonyl, ethylcarbonyl, propylcarbonyl and tert-butyl carbonyl; examples of (1-4C)alkylamino include methylamino, ethylamino, propylamino, isopropylamino, butylamino and tert-butylamino; examples of di(1-4C)alkylamino include dimethylamino, diethylamino, N-methyl-N-ethylamino, dipropylamino, N-isopropyl-N-methyamino and dibutylamino; examples of (1-4C)alkylaminocarbonyl include methylaminocarbonyl, ethylaminocarbonyl, propylaminocarbonyl, isopropylaminocarbonyl, butylaminocarbonyl and tert-butylaminocarbonyl; examples of di(1-4C)alkylaminocarbonyl include dimethylaminocarbonyl, diethylaminocarbonyl, N-methyl-N-ethylaminocarbonyl, dipropylaminocarbonyl, N-isopropyl-N-methyaminocarbonyl and dibutylaminocarbonyl.

It is to be understood that, insofar as certain of the compounds of Formula (I) defined above may exist in optically active or racemic forms by virtue of one or more asymmetric carbon atoms, the invention includes in its definition any such optically active or racemic form which possesses the property of stimulating GLK directly or inhibiting the GLK/GLKRP interaction. The synthesis of optically active forms may be carried out by standard techniques of organic chemistry well known in the art, for example by synthesis from optically active starting materials or by resolution of a racemic form. It is also to be understood that certain compounds may exist in tautomeric forms and that the invention also relates to any and all tautomeric forms of the compounds of the invention which activate GLK.

In one aspect, the compound of formula (I) has the (S)-configuration at the pyrrolidone ring and is thereby a compound of formula (IA):

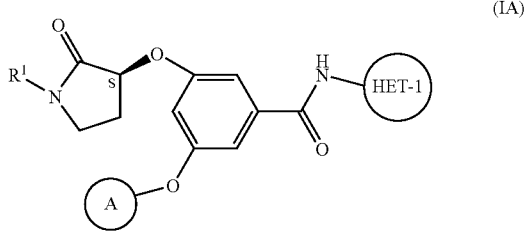

(IA)

In another aspect, the compound of formula (I) has the (R)-configuration at the pyrrolidone ring and is thereby a compound of formula (IB):

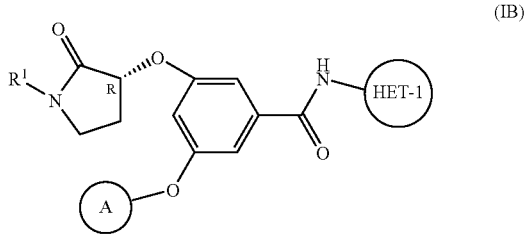

(IB)

The above convention applies equally to compounds of formulae (II), (III) and (IV), so that, for example, when a compound of formula (II) has the pyrrolidine in the S-configuration, it may be described as a compound of formula (IIA), and when a compound of formula (II) has the pyrrolidone substituent in the (R)-configuration it may be described as a compound of formula (IIB).

Thus reference herein to a compound of formula (I) should be understood to refer equally to a compound of formula (I), (IA), (IB), (II), (IIA), (IIB), (III), (IIIA), (IIIB), (IV), (IVA) and (IVB).

It is also to be understood that certain compounds of the formula (I) and salts thereof can exist in solvated as well as unsolvated forms such as, for example, hydrated forms. It is to be understood that the invention encompasses all such solvated forms which activate GLK.

In one embodiment of the invention are provided compounds of formula (I), in an alternative embodiment are provided pharmaceutically-acceptable salts of compounds of formula (I), in a further alternative embodiment are provided in-vivo hydrolysable esters of compounds of formula (I), and in a further alternative embodiment are provided pharmaceutically-acceptable salts of in-vivo hydrolysable esters of compounds of formula (I).

Preferred values of each variable group are as follows. Such values may be used where appropriate with any of the values, definitions, claims, aspects or embodiments defined hereinbefore or hereinafter. In particular, each may be used as an individual limitation on the broadest definition of formulae (I), (TI), (III) and/or (IV), as appropriate. Further, each of the following values may be used in combination with one or more of the other following values to limit the broadest definition of formulae (I), (II), (III) and/or (IV), as appropriate.

(1) $R^1$ is (1-4C)alkyl
(2) $R^1$ is methyl or ethyl
(3) $R^1$ is (3-6C)acycloalkyl, such as cyclobutyl
(4) $R^1$ is methyl, ethyl or cyclobutyl
(5) HET-1 is a 5-membered heteroaryl ring
(6) HET-1 is a 6-membered heteroaryl ring
(7) HET-1 is substituted with 1 or 2 substituents independently selected from $R^6$
(8) HET-1 is substituted with 1 substituent selected from $R^6$
(9) HET-1 is substituted with 1 substituent selected from $R^7$
(10) HET-1 is unsubstituted
(11) HET-1 is selected from thiazolyl, isothiazolyl, thiadiazolyl, pyridyl, pyrazinyl, pyridazinyl, pyrazolyl, imidazolyl, pyrimidinyl, oxazolyl, isoxazolyl, oxadiazolyl, and triazolyl
(12) HET-1 is selected from thiazolyl, isothiazolyl, thiadiazolyl, pyrazolyl, imidazolyl, oxazolyl, isoxazolyl and oxadiazolyl
(13) HET-1 is pyrazolyl, optionally substituted with a methyl group on an available carbon
(14) HET-1 is pyrazinyl, optionally substituted with a methyl group on an available carbon atom
(15) HET-1 is thiazolyl, optionally substituted with a methyl group on an available carbon atom
(16) HET-1 is pyrazinyl, pyrazolyl or thiazolyl, optionally substituted with a methyl group on an available carbon atom
(17) $R^6$ is selected from (1-4C)alkyl, halo, hydroxy(1-4C)alkyl and di(1-4C)alkylamino(1-4C)alkyl
(18) $R^6$ is selected from methyl, ethyl, bromo, chloro, fluoro, hydroxymethyl, methoxymethyl, aminomethyl, N-methylaminomethyl, dimethylaminomethyl
(19) $R^6$ is selected from (1-4C)alkyl, halo, hydroxy(1-4C)alkyl, (1-4C)alkoxy(1-4C)alkyl, (1-4C)alkylS(O)p(1-4C)alkyl, amino(1-4C)alkyl, (1-4C)alkylamino(1-4C)alkyl, and di(1-4C)alkylamino(1-4C)alkyl
(20) $R^6$ is selected from methyl, ethyl, bromo, chloro, fluoro, hydroxymethyl and methoxymethyl
(21) $R^6$ is selected from methyl, ethyl, chloro and fluoro
(22) $R^6$ is methyl
(23) $R^7$ is selected from (1-4C)alkyl, hydroxy(1-4C)alkyl and di(1-4C)alkylamino(1-4C)alkyl
(24) $R^7$ is selected from methyl, ethyl, hydroxymethyl, methoxymethyl, aminomethyl, N-methylaminomethyl, dimethylaminomethyl
(25) $R^7$ is selected from (1-4C)alkyl, hydroxy(1-4C)alkyl, (1-4C)alkoxy(1-4C)alkyl, (1-4C)alkylS(O)p(1-4C)alkyl, amino(1-4C)alkyl, (1-4C)alkylamino(1-4C)alkyl, and di(1-4C)alkylamino(1-4C)alkyl
(26) $R^7$ is selected from methyl, ethyl, aminomethyl, N-methylaminomethyl, and dimethylaminomethyl
(27) $R^7$ is selected from methyl, ethyl, hydroxymethyl and methoxymethyl
(28) $R^7$ is selected from methyl and ethyl
(29) $R^7$ is methyl
(30) Ring A is phenyl
(31) Ring A is HET-2
(32) Ring A is HET-3

(33) $R^3$ is chloro or fluoro
(34) $R^3$ is chloro
(35) $R^3$ is fluoro
(36) $R^2$ is —C(O)NR$^4$R$^5$
(37) $R^2$ is —SO$_2$NR$^4$R$^5$
(38) $R^2$ is SOpR$^4$
(39) $R^2$ is —C(O)NR$^4$R$^5$ or SOpR$^4$
(40) $R^4$ is selected from hydrogen, optionally substituted (1-4C)alkyl and optionally substituted (3-6C)cycloalkyl
(41) $R^4$ is (1-4C)alkyl, such as methyl
(42) $R^5$ is (1-4C)alkyl, such as methyl
(43) $R^5$ is hydrogen
(44) $R^4$ and $R^5$ together with the nitrogen atom to which they are attached form a 4 membered ring
(45) $R^4$ and $R^5$ together with the nitrogen atom to which they are attached form a 5 membered ring
(46) $R^4$ and $R^5$ together with the nitrogen atom to which they are attached form a 6 membered ring
(47) $R^4$ and $R^5$ together with the nitrogen atom to which they are attached form a 7 membered ring
(48) $R^4$ and $R^5$ together with the nitrogen atom to which they are attached form a fully saturated ring
(49) $R^4$ and $R^5$ together with the nitrogen atom to which they are attached form a ring selected from morpholino, piperidinyl, piperazinyl, pyrrolidinyl and azetidinyl
(50) $R^4$ and $R^5$ together with the nitrogen atom to which they are attached form an azetidinyl ring
(51) $R^4$ and $R^5$ together with the nitrogen atom to which they are attached form an unsubstituted ring
(52) $R^4$ and $R^5$ together with the nitrogen atom to which they are attached form a ring mono-substituted either with a substituent $R^8$ or with a substituent $R^9$
(53) $R^4$ and $R^5$ together with the nitrogen atom to which they are attached form a 6-10 membered bicyclic saturated or partially unsaturated ring
(54) $R^8$ is selected from hydroxy, (1-4C)alkoxy, (1-4C)alkyl
(55) $R^8$ is selected from hydroxy, methoxy and methyl
(56) $R^9$ is selected from (1-4C)alkyl and —C(O)(1-4C)alkyl
(57) $R^2$ is azetidinylcarbonyl
(58) HET-2 is a 5-membered heteroaryl ring
(59) HET-2 is a 6-membere heteroaryl ring
(60) HET-2 is selected from pyrazinyl and pyridyl
(61) HET-2 is substituted with a substituent selected from $R^3$
(62) HET-2 has one nitrogen substituent selected from $R^{10}$
(63) $R^{10}$ is (1-4C)alkyl
(64) $R^{10}$ is (3-6C)cycloalkyl
(65) $R^{10}$ is hydroxy(1-4C)alkyl or (1-4C)alkoxy(1-4C)alkyl
(66) $R^{10}$ is —C(O)(1-4C)alkyl
(67) $R^{10}$ is benzyl
(68) $R^{10}$ is (1-4C)alkylsulfonyl
(69) $R^{10}$ is (1-4C)alkyl or benzyl
(70) n=0
(71) n=1
(72) Ring B is phenyl
(73) Ring B is 5- or 6-membered heteroaryl ring
(74) Ring B is phenyl or a 6-membered heteroaryl ring
(75) Ring B is a 5-membered heteroaryl ring
(76) Ring B is a 6-membered heteroaryl ring
(77) Ring C is a 5-membered ring
(78) Ring C is a 6-membered ring
(79) Ring C is a 7-membered ring
(80) Ring C is unsubstituted
(81) Ring C is substituted on an available nitrogen atom by $R^{13}$
(82) Ring C is substituted on each available nitrogen atom by a substituent $R^{13}$, wherein each $R^{13}$ is independently selected from (1-4C)alkyl and benzyl
(83) Ring C is substituted on an available carbon atom by $R^{14}$
(84) Ring C is substituted on more than one available carbon atom by substituents independently selected from $R^{14}$
(85) Ring C is substituted on one or more available carbon atom by methyl, and/or twice on one carbon atom by methyl
(86) Ring B is heteroaryl and Ring C is phenyl
(87) Ring B is heteroaryl and Ring C is heterocyclyl
(88) HET-3 is a 5,6 fused bicyclic system
(89) HET-3 is a 5,5 fused bicyclic system
(90) HET-3 is a 6,6 fused bicyclic system
(91) HET-3 is a 5,7 fused bicyclic system
(92) HET-3 is a 6,7 fused bicyclic system
(93) HET-3 is selected from structures A to F as hereinbefore defined, particularly wherein
$R^{13}$ and $R^{14}$ are both methyl and $R^{12}$ is chloro or fluoro
(94) HET-3 is selected from structures G to P as hereinbefore defined
(95) Ring C is substituted by two $R^{14}$ and both are either methyl or fluoro
(96) Ring C is gem di-substituted by $R^{14}$ and both are either methyl or fluoro
(97) $R^{12}$ is hydrogen
(98) $R^{12}$ is fluoro
(99) $R^{12}$ is chloro
(100) $R^{12}$ is hydrogen or fluoro
(101) HET-3 is selected from structures AA to MM as hereinbefore defined
(102) HET-3 is selected from structures EE, FF, GG and HH
(103) HET-3 is selected from structures EE, FF and GG According to a further feature of the invention there is provided the following preferred groups of compounds of the invention:

In one aspect there is provided a compound of formula (I), or a salt thereof, wherein:

$R^1$ is selected from (1-4C)alkyl and (3-6C)cycloalkyl;

HET-1 is a 5- or 6-membered, C-linked heteroaryl ring containing a nitrogen atom in the 2-position relative to the amide nitrogen to which the ring is attached and optionally 1 or 2 further ring heteroatoms independently selected from O, N and S; which ring is optionally substituted on any nitrogen atom (provided it is not thereby quaternised) by a substituent selected from $R^7$ and/or on 1 or 2 available carbon atoms by a substituent independently selected from $R^6$;

Ring A is selected from phenyl, HET-2 and HET-3; wherein when Ring A is phenyl it is substituted by $R^2$ and optionally further substituted by a group selected from $R^3$;

$R^2$ is selected from —C(O)NR$^4$R$^5$, SOpR$^4$, and —SO$_2$NR$^4$R$^5$;

$R^3$ is selected from halo, methyl and trifluoromethyl;

$R^4$ is selected from hydrogen and (1-4C)alkyl [optionally substituted by a substituent selected from —OR$^5$ and —C(O)NR$^5$R$^5$];

$R^5$ is hydrogen or (1-4C)alkyl;

or $R^4$ and $R^5$ together with the nitrogen atom to which they are attached form a 4 to 7 membered saturated or partially unsaturated heterocyclyl ring, optionally containing 1 or 2 further heteroatoms (in addition to the linking N atom) independently selected from O, N and S, wherein a —CH$_2$— group can optionally be replaced by a —C(O)— and wherein a sulphur atom in the ring may optionally be oxidised to a S(O) or S(O)$_2$ group;

$R^6$ is (1-4C)alkyl;

$R^7$ is (1-4C)alkyl;

HET-2 is a 5- or 6-membered heteroaryl ring, containing 1, 2 or 3 ring hetereoatoms independently selected from O, S and N; which ring is substituted on an available carbon atom by a substituent selected from $R^2$, and is optionally further substituted on 1 or 2 available carbon atoms by a substituent independently selected from $R^3$ and/or on an available nitrogen atom (provided it is not thereby quaternised) by a substituent selected from $R^{10}$;

$R^{10}$ is (1-4C)alkyl;

HET-3 is a fused bicyclic ring system of formula —B—C;

wherein B is a Ring is directly attached to the linking oxygen atom and Ring B is phenyl or is a 5- or 6-membered heteroaryl ring containing 1, 2 or 3 heteroatoms independently selected from O, N and S (provided there are no O—O, S—S or O—S bonds in the ring);

wherein Ring B is optionally substituted on any nitrogen atom by a substituent selected from $R^{11}$ and/or on any available carbon atom by 1 or 2 substituents independently selected from $R^{12}$;

$R^{11}$ is (1-4C)alkyl;

$R^{12}$ is independently selected from (1-4C)alkyl and halo;

Ring C is a 5-7 membered heterocyclic ring fused to Ring B, containing 1, 2 or 3 ring hetereoatoms independently selected from O, S and N (provided that there are no O—O, S—O or S—S bonds within the ring), wherein any ring carbon or sulfur atom may optionally be oxidised and wherein Ring C is optionally substituted on any nitrogen atom by a substituent selected from $R^{13}$ and/or on any available carbon atom by 1 or 2 substituents independently selected from $R^{14}$;

$R^{13}$ is (1-4C)alkyl;

$R^{14}$ is selected from (1-4C)alkyl, fluoro and chloro;

n is 0 or 1;

p is (independently at each occurrence) 0, 1 or 2.

In another aspect of the invention there is provided a compound of formula (II), or a salt thereof, wherein $R^1$ is selected from (1-4C)alkyl and (3-6C)cycloalkyl;

HET-1 is a 5- or 6-membered, C-linked heteroaryl ring containing a nitrogen atom in the 2-position relative to the amide nitrogen to which the ring is attached and optionally 1 or 2 further ring heteroatoms independently selected from O, N and S; which ring is optionally substituted on any nitrogen atom (provided it is not thereby quaternised) by a substituent selected from $R^7$ and/or on 1 or 2 available carbon atoms by a substituent independently selected from $R^6$;

Ring A is phenyl, substituted by $R^2$ and optionally further substituted by a group selected from $R^3$;

$R^2$ is selected from —C(O)NR$^4$R$^5$, SOpR$^4$ and —SO$_2$NR$^4$R$^5$;

$R^3$ is halo;

$R^4$ is selected from hydrogen and (1-4C)alkyl [optionally substituted by a substituent selected from —OR$^5$ and —C(O)NR$^5$R$^5$];

$R^5$ is hydrogen or (1-4C)alkyl;

or $R^4$ and $R^5$ together with the nitrogen atom to which they are attached form a 4 to 7 membered saturated or partially unsaturated heterocyclyl ring, optionally containing 1 or 2 further heteroatoms (in addition to the linking N atom) independently selected from O, N and S, wherein a —CH$_2$— group can optionally be replaced by a —C(O)— and wherein a sulphur atom in the ring may optionally be oxidised to a S(O) or S(O)$_2$ group;

$R^6$ is (1-4C)alkyl;

$R^7$ is (1-4C)alkyl;

n is 0 or 1;

p is (independently at each occurrence) 0, 1 or 2.

In a further aspect of the invention there is provided a compound of formula (IV), or a salt thereof, wherein:

$R^1$ is selected from (1-4C)alkyl and (3-6C)cycloalkyl;

HET-1 is a 5- or 6-membered, C-linked heteroaryl ring containing a nitrogen atom in the 2-position relative to the amide nitrogen to which the ring is attached and optionally 1 or 2 further ring heteroatoms independently selected from O, N and S; which ring is optionally substituted on any nitrogen atom (provided it is not thereby quaternised) by a substituent selected from $R^7$ and/or on 1 or 2 available carbon atoms by a substituent independently selected from $R^6$;

Ring A is HET-3;

HET-3 is a fused bicyclic ring system selected from formulae A to P as hereinbefore defined;

$R^{12}$ is independently selected from (1-4C)alkyl and halo;

$R^{13}$ is (1-4C)alkyl;

$R^{14}$ is selected from (1-4C)alkyl, fluoro and chloro;

$R^6$ is (1-4C)alkyl;

$R^7$ is (1-4C)alkyl;

n is 0 or 1;

p is (independently at each occurrence) 0, 1 or 2.

In a further aspect of the invention there is provided a compound of formula (IV), or a salt thereof, wherein:

$R^1$ is selected from (1-4C)alkyl and (3-6C)cycloalkyl;

HET-1 is a 5- or 6-membered, C-linked heteroaryl ring containing a nitrogen atom in the 2-position relative to the amide nitrogen to which the ring is attached and optionally 1 or 2 further ring heteroatoms independently selected from O, N and S; which ring is optionally substituted on any nitrogen atom (provided it is not thereby quaternised) by a substituent selected from $R^7$ and/or on 1 or 2 available carbon atoms by a substituent independently selected from $R^6$;

Ring A is HET-3;

HET-3 is a fused bicyclic ring system selected from formulae AA to MM as hereinbefore defined;

$R^{12}$ is independently selected from (1-4C)alkyl and halo;

$R^{13}$ is (1-4C)alkyl;

$R^{14}$ is selected from (1-4C)alkyl, fluoro and chloro;

$R^6$ is (1-4C)alkyl;

$R^7$ is (1-4C)alkyl;

n is 0 or 1;

p is (independently at each occurrence) 0, 1 or 2.

In a further aspect of the invention there is provided a compound of formula (IV), or a salt thereof, wherein:

$R^1$ is selected from (1-4C)alkyl and (3-6C)cycloalkyl;

HET-1 is a 5- or 6-membered, C-linked heteroaryl ring containing a nitrogen atom in the 2-position relative to the amide nitrogen to which the ring is attached and optionally 1 or 2 further ring heteroatoms independently selected from O, N and S; which ring is optionally substituted on any nitrogen atom (provided it is not thereby quaternised) by a substituent selected from $R^7$ and/or on 1 or 2 available carbon atoms by a substituent independently selected from $R^6$;

Ring A is HET-3;

HET-3 is a fused bicyclic ring system selected from formulae EE, FF, GG and HH as hereinbefore defined;

$R^{12}$ is independently selected from (1-4C)alkyl and halo;

$R^{13}$ is (1-4C)alkyl;

$R^{14}$ is selected from (1-4C)alkyl, fluoro and chloro;

$R^6$ is (1-4C)alkyl;

$R^7$ is (1-4C)alkyl;

n is 0 or 1;

p is (independently at each occurrence) 0, 1 or 2.

According to a further feature of the invention there is provided any one, two or more of the following compounds, or salts thereof:

3-[6-(azetidine-1-carbonyl)pyridin-3-yl]oxy-5-[(3S)-1-methyl-2-oxo-pyrrolidin-3-yl]oxy-N-(5-methylpyrazin-2-yl)benzamide;

3-[6-(azetidine-1-carbonyl)pyridin-3-yl]oxy-5-[(3R)-1-methyl-2-oxo-pyrrolidin-3-yl]oxy-N-(5-methylpyrazin-2-yl)benzamide;

3-[5-(azetidine-1-carbonyl)pyrazin-2-yl]oxy-5-[(3S)-1-methyl-2-oxo-pyrrolidin-3-yl]oxy-N-(4-methyl 1,3-thiazol-2-yl)benzamide;

3-[5-(azetidine-1-carbonyl)pyrazin-2-yl]oxy-5-[(3R)-1-methyl-2-oxo-pyrrolidin-3-yl]oxy-N-(4-methyl 1,3-thiazol-2-yl)benzamide;

3-[4-(azetidine-1-carbonyl)phenoxy]-5-[(3S)-1-methyl-2-oxo-pyrrolidin-3-yl]oxy-N-(1H-pyrazol-3-yl)benzamide;

3-[5-(azetidine-1-carbonyl)-3-chloro-pyridin-2-yl]oxy-5-[(3S)-1-methyl-2-oxo-pyrrolidin-3-yl]oxy-N-(5-methylpyrazin-2-yl)benzamide;

3-[(3S)-1-methyl-2-oxo-pyrrolidin-3-yl]oxy-N-(5-methylpyrazin-2-yl)-5-(4-methylsulfonylphenoxy)benzamide;

3-[4-(azetidine-1-carbonyl)phenoxy]-5-[(3S)-1-methyl-2-oxo-pyrrolidin-3-yl]oxy-N-(5-methylpyrazin-2-yl)benzamide;

3-[(2,2-dioxo-6-oxa-2-$\lambda^6$-thiabicyclo[5.4.0]undeca-7,9,11-trien-9-yl)oxy]-5-[(3S)-1-methyl-2-oxo-pyrrolidin-3-yl]oxy-N-(5-methylpyrazin-2-yl)benzamide;

3-[6-(azetidine-1-carbonyl)pyridin-3-yl]oxy-5-(1-ethyl-2-oxo-pyrrolidin-3-yl)oxy-N-(5-methylpyrazin-2-yl)benzamide;

3-[(5-methyl-6,6-dioxo-2-oxa-6-$\lambda^6$-thia-5-azabicyclo[5.4.0]undeca-8,10,12-trien-10-yl)oxy]-5-(1-methyl-2-oxo-pyrrolidin-3-yl)oxy-N-(5-methylpyrazin-2-yl)benzamide;

3-[6-(azetidine-1-carbonyl)pyridin-3-yl]oxy-5-[(3S)-1-methyl-2-oxo-pyrrolidin-3-yl]oxy-N-pyrazin-2-yl-benzamide;

3-[6-(azetidine-1-carbonyl)pyridin-3-yl]oxy-5-[(3S)-1-methyl-2-oxo-pyrrolidin-3-yl]oxy-N-pyridin-2-yl-benzamide;

3-[(11-chloro-5-methyl-6-oxo-2-oxa-5-azabicyclo[5.4.0]undeca-8,10,12-trien-10-yl)oxy]-5-[(3S)-1-methyl-2-oxo-pyrrolidin-3-yl]oxy-N-(5-methylpyrazin-2-yl)benzamide;

3-[(4-methyl-5-oxo-2-oxa-4-azabicyclo[4.4.0]deca-6,8,10-trien-9-yl)oxy]-5-(1-methyl-2-oxo-pyrrolidin-3-yl)oxy-N-(5-methylpyrazin-2-yl)benzamide;

3-[(5-methyl-6-oxo-2-oxa-5-azabicyclo[5.4.0]undeca-8,10,12-trien-10-yl)oxy]-5-[(3S)-1-methyl-2-oxo-pyrrolidin-3-yl]oxy-N-(5-methylpyrazin-2-yl)benzamide;

3-[6-(azetidine-1-carbonyl)pyridin-3-yl]oxy-5-(1-cyclobutyl-2-oxo-pyrrolidin-3-yl)oxy-N-(5-methylpyrazin-2-yl)benzamide;

3-[6-(Azetidine-1-carbonyl)pyridin-3-yl]oxy-5-[(3R)-1-cyclopropyl-2-oxo-pyrrolidin-3-yl]oxy-N-(5-methylpyrazin-2-yl)benzamide;

3-[6-(Azetidine-1-carbonyl)pyridin-3-yl]oxy-5-[(3S)-1-cyclopropyl-2-oxo-pyrrolidin-3-yl]oxy-N-(5-methylpyrazin-2-yl)benzamide;

3-[6-(Azetidine-1-carbonyl)pyridin-3-yl]oxy-5-[(3R)-1-cyclobutyl-2-oxo-pyrrolidin-3-yl]oxy-N-(5-methylpyrazin-2-yl)benzamide;

3-[6-(Azetidine-1-carbonyl)pyridin-3-yl]oxy-5-[(3S)-1-clobutyl-2-oxo-pyrrolidin-3-yl]oxy-N-(5-methylpyrazin-2-yl)benzamide;

3-[6-(Azetidine-1-carbonyl)pyridin-3-yl]oxy-5-[(3R)-1-ethyl-2-oxo-pyrrolidin-3-yl]oxy-N-(5-methylpyrazin-2-yl)benzamide;

3-[6-(Azetidine-1-carbonyl)pyridin-3-yl]oxy-5-[(3S)-1-ethyl-2-oxo-pyrrolidin-3-yl]oxy-N-(5-methylpyrazin-2-yl)benzamide;

N,N-Dimethyl-5-[3-[(3S)-1-methyl-2-oxo-pyrrolidin-3-yl]oxy-5-[(5-methylpyrazin-2-yl)carbamoyl]phenoxy]pyrazine-2-carboxamide;

3-[(2,2-Dioxo-6-oxa-2-$\lambda^6$-thiabicyclo[5.4.0]undeca-7,9,11-trien-9-yl)oxy]-5-[(3S)-1-methyl-2-oxo-pyrrolidin-3-yl]oxy-N-(1H-pyrazol-3-yl)benzamide;

3-[2-Chloro-4-(dimethylcarbamoyl)phenoxy]-5-[(3S)-1-methyl-2-oxo-pyrrolidin-3-yl]oxy-N-(5-methylpyrazin-2-yl)benzamide;

3-[(6,6-dioxo-2-oxa-6-$\lambda^6$-thia-5-azabicyclo[5.4.0]undeca-8,10,12-trien-10-yl)oxy]-5-[(3S)-1-methyl-2-oxo-pyrrolidin-3-yl]oxy-N-(5-methylpyrazin-2-yl)benzamide;

3-[(3S)-1-methyl-2-oxo-pyrrolidin-3-yl]oxy-N-(5-methylpyrazin-2-yl)-5-(6-methylsulfonylpyridin-3-yl)oxy-benzamide;

N,N-dimethyl-5-[3-[(3S)-1-methyl-2-oxo-pyrrolidin-3-yl]oxy-5-[(5-methylpyrazin-2-yl)carbamoyl]phenoxy]pyridine-2-carboxamide;

3-[(9-methyl-10-oxo-7-oxa-9-azabicyclo[4.4.0]deca-2,4,11-trien-4-yl)oxy]-5-[(3S)-1-methyl-2-oxo-pyrrolidin-3-yl]oxy-N-(1H-pyrazol-3-yl)benzamide;

N,N-dimethyl-5-[3-[(3S)-1-methyl-2-oxo-pyrrolidin-3-yl]oxy-5-[(3-methyl-1,2,4-thiadiazol-5-yl)carbamoyl]phenoxy]pyrazine-2-carboxamide; and N,N-Dimethyl-5-[3-[(3S)-1-methyl-2-oxo-pyrrolidin-3-yl]oxy-5-[(4-methyl-1,3-thiazol-2-yl)carbamoyl]phenoxy]pyrazine-2-carboxamide.

The compounds of the invention may be administered in the form of a pro-drug. A pro-drug is a bioprecursor or pharmaceutically acceptable compound being degradable in the body to produce a compound of the invention (such as an ester or amide of a compound of the invention, particularly an in-vivo hydrolysable ester). Various forms of prodrugs are known in the art. For examples of such prodrug derivatives, see:

a) Design of Prodrugs, edited by H. Bundgaard, (Elsevier, 1985) and Methods in Enzymology, Vol. 42, p. 309-396, edited by K. Widder, et al. (Academic Press, 1985);

b) A Textbook of Drug Design and Development, edited by Krogsgaard-Larsen;

c) H. Bundgaard, Chapter 5 "Design and Application of Prodrugs", by H. Bundgaard p. 113-191 (1991);

d) H. Bundgaard, Advanced Drug Delivery Reviews, 8, 1-38 (1992);

e) H. Bundgaard, et al., Journal of Pharmaceutical Sciences, 77, 285 (1988); and f) N. Kakeya, et al., Chem Pharm Bull, 32, 692 (1984).

The contents of the above cited documents are incorporated herein by reference.

Examples of pro-drugs are as follows. An in-vivo hydrolysable ester of a compound of the invention containing a carboxy or a hydroxy group is, for example, a pharmaceutically-acceptable ester which is hydrolysed in the human or animal body to produce the parent acid or alcohol. Suitable pharmaceutically-acceptable esters for carboxy include $C_1$ to $C_6$alkoxymethyl esters for example methoxymethyl, $C_1$ to $C_6$alkanoyloxymethyl esters for example pivaloyloxymethyl, phthalidyl esters, $C_3$ to $C_8$cycloalkoxycarbonyloxy$C_1$ to $C_6$alkyl esters for example 1-cyclohexylcarbonyloxyethyl;

1,3-dioxolen-2-onylmethyl esters, for example 5-methyl-1,3-dioxolen-2-onylmethyl; and $C_{1-6}$alkoxycarbonyloxyethyl esters.

An in-vivo hydrolysable ester of a compound of the invention containing a hydroxy group includes inorganic esters such as phosphate esters (including phosphoramidic cyclic esters) and α-acyloxyalkyl ethers and related compounds which as a result of the in-vivo hydrolysis of the ester breakdown to give the parent hydroxy group/s. Examples of α-acyloxyalkyl ethers include acetoxymethoxy and 2,2-dimethylpropionyloxy-methoxy. A selection of in-vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl.

Under certain conditions, compounds of Formula (I) may form pharmaceutically acceptable salts. A suitable pharmaceutically-acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulphuric, phosphoric, trifluoroacetic, citric or maleic acid. In addition a suitable pharmaceutically acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

A further feature of the invention is a pharmaceutical composition comprising a compound of Formula (I) as defined above, or a pharmaceutically-acceptable salt thereof, together with a pharmaceutically-acceptable diluent or carrier.

According to another aspect of the invention there is provided a compound of Formula (I) as defined above or a pharmaceutically-acceptable salt thereof for use as a medicament.

According to another aspect of the invention there is provided a compound of Formula (I), or a pharmaceutically-acceptable salt thereof as defined above for use as a medicament for treatment of a disease mediated through GLK, in particular type 2 diabetes.

Further according to the invention there is provided the use of a compound of Formula (I) or a pharmaceutically-acceptable salt thereof in the preparation of a medicament for treatment of a disease mediated through GLK, in particular type 2 diabetes.

The compound is suitably formulated as a pharmaceutical composition for use in this way.

According to another aspect of the present invention there is provided a method of treating GLK mediated diseases, especially diabetes, by administering an effective amount of a compound of Formula (I) or a pharmaceutically-acceptable salt thereof, to a mammal in need of such treatment.

According to another aspect of the present invention there is provided the use of a compound of Formula (I), or a pharmaceutically-acceptable salt thereof, for treatment of a disease mediated through GLK.

According to another aspect of the present invention there is provided the use of a compound of Formula (I), or a pharmaceutically-acceptable salt thereof, for treatment of type 2 diabetes.

Specific diseases which may be treated by a compound or composition of the invention include: blood glucose lowering in Type 2 Diabetes Mellitus without a serious risk of hypoglycaemia (and potential to treat type 1), dyslipidemia, obesity, insulin resistance, metabolic syndrome X, impaired glucose tolerance.

As discussed above, thus the GLK/GLKRP system can be described as a potential "Diabesity" target (of benefit in both Diabetes and Obesity). Thus, according to another aspect of the invention there is provided the use of a compound of Formula (I) or a pharmaceutically-acceptable salt thereof, in the preparation of a medicament for use in the combined treatment or prevention, particularly treatment, of diabetes and obesity.

According to another aspect of the invention there is provided the use of a compound of Formula (I) or a pharmaceutically-acceptable salt thereof, in the preparation of a medicament for use in the treatment or prevention of obesity.

According to a further aspect of the invention there is provided a method for the combined treatment of obesity and diabetes by administering an effective amount of a compound of Formula (I) or a pharmaceutically-acceptable salt thereof, to a mammal in need of such treatment.

According to another aspect of the invention there is provided a compound of Formula (I) or a pharmaceutically-acceptable salt thereof as defined above for use as a medicament for treatment or prevention, particularly treatment of obesity.

According to a further aspect of the invention there is provided a method for the treatment of obesity by administering an effective amount of a compound of Formula (I) or a pharmaceutically-acceptable salt thereof, to a mammal in need of such treatment.

Compounds of the invention may be particularly suitable for use as pharmaceuticals because of advantageous physical and/or pharmacokinetic properties, and/or favourable toxicity profile.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing). Dosage forms suitable for oral use are preferred.

The compositions of the invention may be obtained by conventional procedures using conventional pharmaceutical excipients, well known in the art. Thus, compositions intended for oral use may contain, for example, one or more colouring, sweetening, flavouring and/or preservative agents.

Suitable pharmaceutically acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), colouring agents, flavouring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavouring and colouring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavouring and preservative agents.

Syrups and elixirs may be formulated with sweetening agents such as glycerol, propylene glycol, sorbitol, aspartame or sucrose, and may also contain a demulcent, preservative, flavouring and/or colouring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Compositions for administration by inhalation may be in the form of a conventional pressurised aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on formulation the reader is referred to Chapter 25.2 in Volume 5 of Comprehensive Medicinal Chemistry (Corwin Hansch; Chairman of Editorial Board), Pergamon Press 1990.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

The size of the dose for therapeutic or prophylactic purposes of a compound of the Formula (I) will naturally vary according to the nature and severity of the conditions, the age and sex of the animal or patient and the route of administration, according to well known principles of medicine.

In using a compound of the Formula (I) for therapeutic or prophylactic purposes it will generally be administered so that a daily dose in the range, for example, 0.5 mg to 75 mg per kg body weight is received, given if required in divided doses. In general lower doses will be administered when a parenteral route is employed. Thus, for example, for intravenous administration, a dose in the range, for example, 0.5 mg to 30 mg per kg body weight will generally be used. Similarly, for administration by inhalation, a dose in the range, for example, 0.5 mg to 25 mg per kg body weight will be used. Oral administration is however preferred.

The elevation of GLK activity described herein may be applied as a sole therapy or in combination with one or more other substances and/or treatments for the indication being treated. Such conjoint treatment may be achieved by way of the simultaneous, sequential or separate administration of the individual components of the treatment. Simultaneous treatment may be in a single tablet or in separate tablets. For example in the treatment of diabetes mellitus, chemotherapy may include the following main categories of treatment:
1) Insulin and insulin analogues;
2) Insulin secretagogues including sulphonylureas (for example glibenclamide, glipizide), prandial glucose regulators (for example repaglinide, nateglinide);
3) Agents that improve incretin action (for example dipeptidyl peptidase IV inhibitors, and GLP-1 agonists);
4) Insulin sensitising agents including PPARgamma agonists (for example pioglitazone and rosiglitazone), and agents with combined PPARalpha and gamma activity;

5) Agents that modulate hepatic glucose balance (for example metformin, fructose 1, 6 bisphosphatase inhibitors, glycogen phopsphorylase inhibitors, glycogen synthase kinase inhibitors);
6) Agents designed to reduce the absorption of glucose from the intestine (for example acarbose);
7) Agents that prevent the reabsorption of glucose by the kidney (SGLT inhibitors);
8) Agents designed to treat the complications of prolonged hyperglycaemia (for example aldose reductase inhibitors);
9) Anti-obesity agents (for example sibutramine and orlistat);
10) Anti-dyslipidaemia agents such as, HMG-CoA reductase inhibitors (eg statins); PPARα agonists (fibrates, eg gemfibrozil); bile acid sequestrants (cholestyramine); cholesterol absorption inhibitors (plant stanols, synthetic inhibitors); bile acid absorption inhibitors (IBATi) and nicotinic acid and analogues (niacin and slow release formulations);
11) Antihypertensive agents such as, β blockers (eg atenolol, inderal); ACE inhibitors (eg lisinopril); Calcium antagonists (eg. nifedipine); Angiotensin receptor antagonists (eg candesartan), α antagonists and diuretic agents (eg. furosemide, benzthiazide);
12) Haemostasis modulators such as, antithrombotics, activators of fibrinolysis and antiplatelet agents; thrombin antagonists; factor Xa inhibitors; factor VIa inhibitors); antiplatelet agents (eg. aspirin, clopidogrel); anticoagulants (heparin and Low molecular weight analogues, hirudin) and warfarin;
13) Agents which antagonise the actions of glucagon; and
14) Anti-inflammatory agents, such as non-steroidal anti-inflammatory drugs (eg. aspirin) and steroidal anti-inflammatory agents (eg. cortisone).

According to another aspect of the present invention there is provided individual compounds produced as end products in the Examples set out below and salts thereof.

A compound of the invention, or a salt thereof, may be prepared by any process known to be applicable to the preparation of such compounds or structurally related compounds. Functional groups may be protected and deprotected using conventional methods. For examples of protecting groups such as amino and carboxylic acid protecting groups (as well as means of formation and eventual deprotection), see T. W. Greene and P. G. M. Wuts, "Protective Groups in Organic Synthesis", Second Edition, John Wiley & Sons, New York, 1991.

Processes for the synthesis of compounds of Formula (I) are provided as a further feature of the invention. Thus, according to a further aspect of the invention there is provided a process for the preparation of a compound of Formula (I), which comprises a process a) to g) (wherein the variables are as defined hereinbefore for compounds of Formula (I) unless otherwise defined):

(a) reaction of an acid of Formula (V) or activated derivative thereof with a compound of Formula (VI);

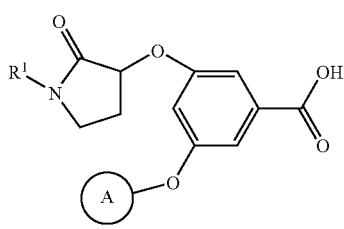
(V)

(VI)

or (b) reaction of a compound of Formula (VII) with a compound of Formula (VIII),

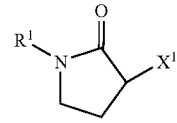
(VII)

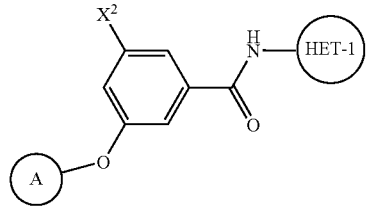
(VIII)

wherein $X^1$ is a leaving group and $X^2$ is a hydroxyl group or $X^1$ is a hydroxyl group and $X^2$ is a leaving group;

process (b) could also be accomplished using the intermediate ester Formula (IX), wherein $P^1$ is a protecting group as hereinafter described, followed by ester hydrolysis and amide formation by procedures described elsewhere and well known to those skilled in the art;

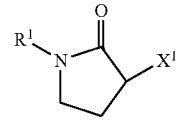
(VII)

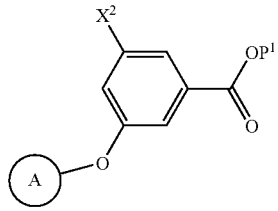
(IX)

or (c) reaction of a compound of Formula (X) with a compound of Formula (XI):

(X)

(XI)

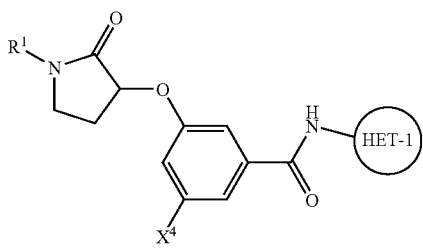

wherein X³ is a leaving group or an organometallic reagent and X⁴ is a hydroxyl group or X³ is a hydroxyl group and X⁴ is a leaving group or an organometallic reagent;

process (c) could also be accomplished using the intermediate ester Formula (XII), followed by ester hydrolysis and amide formation by procedures described elsewhere and well known to those skilled in the art;

(X)

(XII)

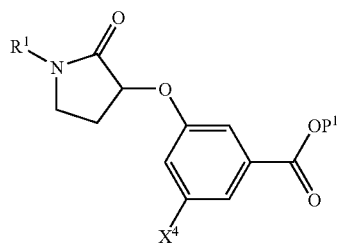

(d) reaction of a compound of Formula (XIII) with a compound of Formula (XIV), (XIII)

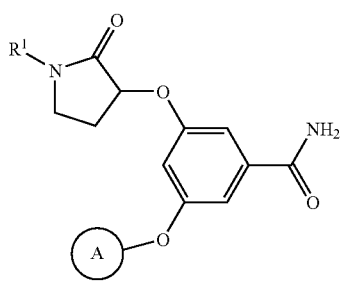

(XIV)

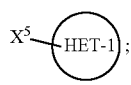

wherein X⁵ is a leaving group; or e) when A is phenyl or HET-2, by reaction of a compound of formula (XV)

(XV)

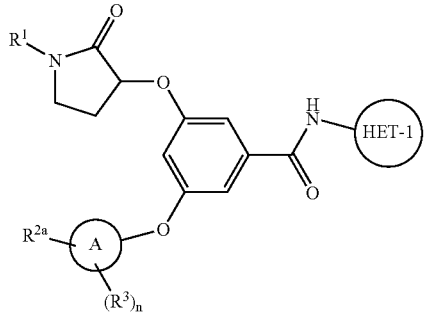

wherein $R^{2a}$ is a precursor to $R^2$, such as a carboxylic acid, ester or anhydride (for $R^2$=—$CONR^4R^5$) or the sulfonic acid equivalents (for $R^2$ is —$SO_2 NR^4R^5$); with an amine of formula —$NR^4R^5$;

f) when A is HET-3, by cyclisation of a compound of formula (XVI) to a compound of formula (I)

(XVI)

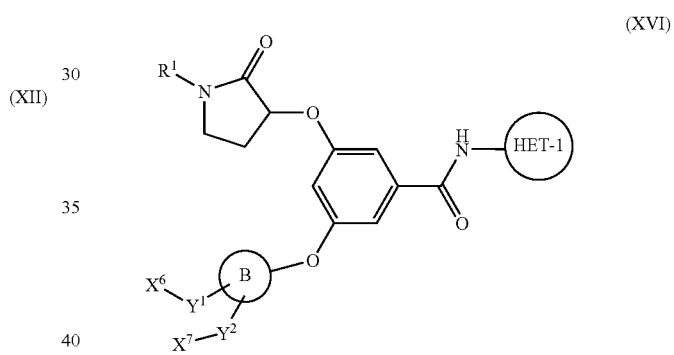

wherein $Y^1$ and $Y^2$ are 0-4 atom linkers, wherein each linker atom is independently selected from C, N, S or O (wherein any C or S can be optionally oxidised and any atom can be optionally substituted provided it is not quaternised and there are no S—S or O—O bonds), $X^6$ can be any nucleophilic species and $X^7$ a leaving group or vice versa;

process (f) could also be accomplished using the intermediate ester Formula (XVII), followed by ester hydrolysis and amide formation by procedures described elsewhere and well known to those skilled in the art;

(XVII)

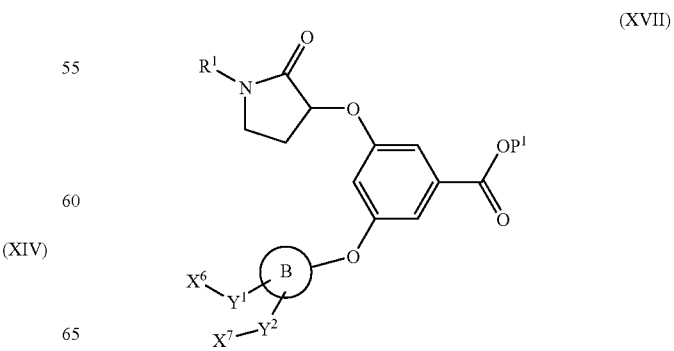

(g) reaction of a compound of Formula (XX) with a suitable metal iodide, such as sodium iodide, and a (1-4C)alkylamine or (3-6C)cycloalkylamine, in a suitable solvent, for example acetonitrile, and at a suitable temperature with heating in a microwave, for example 100 to 130° C., more suitably 115 to 125° C.;

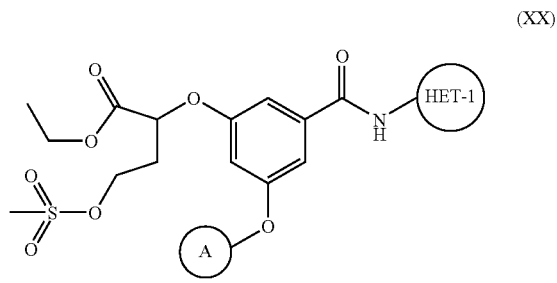

(XX)

and thereafter, if necessary:

i) converting a compound of Formula (I) into another compound of Formula (I);
ii) removing any protecting groups; and/or
iii) forming a salt thereof.

Suitable leaving groups $X^1$ to $X^5$ for processes b) to d) are any leaving group known in the art for these types of reactions, for example halo, alkoxy, trifluoromethanesulfonyloxy, methanesulfonyloxy, or p-toluenesulfonyloxy; or a group (such as a hydroxy group) that may be converted into a leaving group (such as an oxytriphenylphosphonium group) in situ.

Suitable values for $R^1$ containing a protected hydroxy group are any suitable protected hydroxy group known in the art, for example simple ethers such as a methyl ether, tert-butyl ether or silylethers such as —OSi[(1-4C)alkyl]$_3$ (wherein each (1-4C)alkyl group is independently selected from methyl, ethyl, propyl, isopropyl, and tertbutyl). Examples of such trialkylsilyl groups are trimethylsilyl, triethylsilyl, triisopropylsilyl and tert-butyldimethylsilyl. Further suitable silyl ethers are those containing phenyl and substituted phenyl groups, such as —Si(PhMe$_2$) and —Si(TolMe$_2$) (wherein Tol=methylbenzene). Further suitable values for hydroxy protecting groups are given hereinafter.

Compounds of Formulae (V) to (XIV) are commercially available, or are known in the art, or may be made by processes known in the art, for example as shown in the accompanying Examples, or as described below. For further information on processes for making such compounds, we refer to our PCT publications WO 03/000267, WO 03/015774 and WO 03/000262 and references therein. In general it will be appreciated that any aryl-O or alkyl-O bond may be formed by nucleophilic substitution or metal catalysed processes, optionally in the presence of a suitable base.

Compounds of Formula (XV) may be made by processes such as those shown in processes a) to d) and/or by those processes mentioned above for compounds of formulae (V) to (XIV).

The pyrrolidone group in the compounds of formulae (V), (XI), (XII), (XIII), (XV) and (XVI) may be made by reaction of suitable precursors with compounds of formula (VII) or derivatives thereof, for example, by nucleophilic displacement of a leaving group $X^1$ in a compound of formula (VII). Compounds of formula (VII) are generally commercially available or maybe made by simple functional group interconversions from commercially available compounds, or by literature methods. Examples of approaches to the pyrrolidone group are outlined in Schemes 1 and 2 below and are further illustrated in the accompanying examples.

Scheme 1

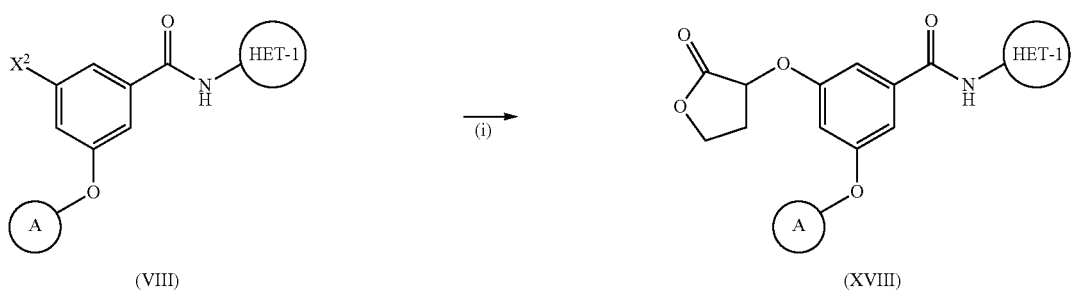

(VIII) (XVIII)

↓ (ii)

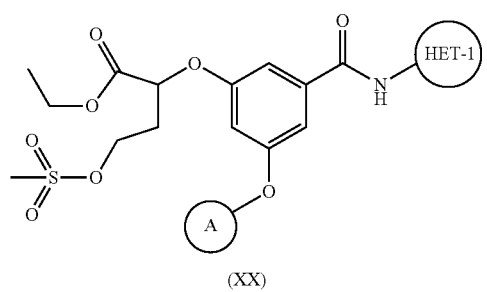

(XX)

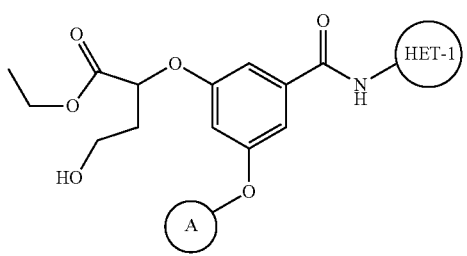

(XIX)

(iii) ←

(iv) ↓

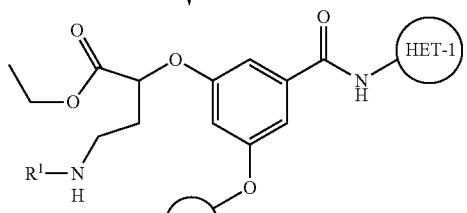

(XXI)

(v) →

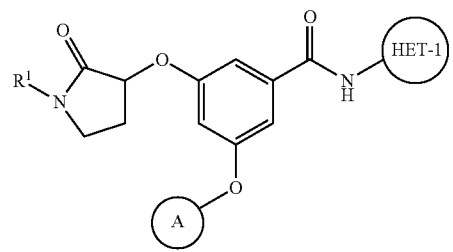

(I)

Wherein:

ring A, HET-1 and $R^1$ are as described above and $X^2$ represents a hydroxyl group. Suitable reaction conditions for steps (i) to (v) of Scheme 1 are as follows:

Step (i) proceeds according to the Mitsunobu reaction as is well known in the literature, more specifically, step (i) involves the reaction of a compound of Formula (VIII) with 3-hydroxyoxolan-2-one in the presence of triphenyl phosphine and DIAD, in a suitable solvent, for example anhydrous THF, and at a suitable temperature, for example 0 to 25° C., more suitably 20 to 25° C.;

Step (ii) involves the reaction of a compound of Formula (XVIII) with a suitable alcohol, for example ethanol, in the presence of a suitable base, for example potassium carbonate, and at a suitable temperature, for example 0 to 25° C., more suitably 20 to 25° C.;

Step (iii) involves the reaction of a compound fo Formula (XIX) with methanesulfonyl chloride in the presence of a suitable base, for example triethylamine, in a suitable solvent, for example DCM, and at a suitable temperature, for example 0 to 25° C., more suitably 20 to 25° C.; and Steps (iv) and (v) involve the reaction of a compound of Formula (XX) with a suitable metal iodide, such as sodium iodide, and a (1-4C)alkylamine or (3-6C)cycloalkylamine, in a suitable solvent, for example acetonitrile, and at a suitable temperature with heating in a microwave, for example 100 to 130° C., more suitably 115 to 125° C.

Scheme 2

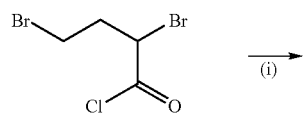

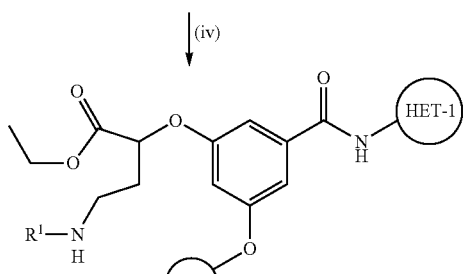

(XXIII)

(ii) →

(XXIV)

Wherein:

$R^1$ is selected from (1-4C)alkyl and (3-6C)cycloalkyl.

Suitable reaction conditions for steps (i) and (ii) of Scheme 2 are as follows:

Step (i) involves the reaction of 2,4-dibromobutanoyl chloride with a (1-4C)alkylamine or (3-6C)cycloalkylamine in a suitable solvent, such as water and DCM, and at a suitable temperature, for example 0 to 50° C., more suitably 10 to 30° C.; and Step (ii) involves the reaction of a compound of Formula (XXIII) with a suitable base, for example sodium hydride, in a suitable solvent, for example THF, and at a suitable temperature, for example 0 to 30° C., more suitably 10 to 15° C.

Examples of conversions of a compound of Formula (I) into another compound of Formula (I), well known to those skilled in the art, include functional group interconversions such as hydrolysis, hydrogenation, hydrogenolysis, oxidation or reduction, and/or further functionalisation by standard reactions such as amide or metal-catalysed coupling, or nucleophilic displacement reactions.

It will be understood that substituents $R^3$, $R^6$ and/or $R^7$ may be introduced into the molecule at any convenient point in the synthetic sequence or may be present in the starting materials. A precursor to one of these substituents may be present in the molecule during the process steps a) to e) above, and then be transformed into the desired substituent as a final step to form the compound of formula (I); followed where necessary by i) converting a compound of Formula (I) into another compound of Formula (I);
ii) removing any protecting groups; and/or
iii) forming a salt thereof.

Specific reaction conditions for the above reactions are as follows, wherein when $P^1$ is a protecting group $P^1$ is preferably (1-4C)alkyl, for example methyl or ethyl:

Process a)—coupling reactions of amino groups with carboxylic acids to form an amide are well known in the art. For example, (i) using an appropriate coupling reaction, such as a carbodiimide coupling reaction performed with EDAC (1-(3-dimethylaminopropyl)-3-ethylcarbodiimide hydrochloride) in the presence of dimethylaminopyridine (DMAP) in a suitable solvent such as dichloromethane (DCM), chloroform or dimethylformamide (DMF) at room temperature; or (ii) reaction in which the carboxylic group is activated to an acid chloride by reaction with a reagent known for such reactions such as 1-chloro-N,N,2-trimethyl-prop-1-en-1-amine in the presence of a suitable solvent such as DCM. The acid chloride can then be reacted with a compound of Formula (VI) in the presence of a base, such as triethylamine or pyridine, in a suitable solvent such as chloroform or DCM at a temperature between 0° C. and 80° C.

Process b)—compounds of Formula (VII) and (VIII) can be reacted together in a suitable solvent, such as DMF or tetrahydrofuran (THF), with a base such as sodium hydride or potassium tert-butoxide, at a temperature in the range 0 to 200° C., optionally using microwave heating or metal catalysis such as palladium(II) acetate, palladium on carbon, copper(II) acetate or copper(I) iodide; alternatively, compounds of Formula (VII) and (VIII) can be reacted together in a suitable solvent, such as THF or DCM, with a suitable phosphine such as triphenylphosphine, and an azodicarboxylate such as diethylazodicarboxylate; process b) could also be carried out using a precursor to the ester of formula (IX) such as an aryl-nitrile or trifluoromethyl derivative, followed by conversion to a carboxylic acid and amide formation as previously described;

Process c)—compounds of Formula (X) and (X$^1$) can be reacted together in a suitable solvent, such as DMF or THF, with a base such as cesium carbonate, sodium hydride or potassium tert-butoxide, at a temperature in the range 0 to 200° C., optionally using microwave heating or metal catalysis such as palladium(II) acetate, palladium on carbon, copper(II) acetate, tris(triphenylphosphine)copper bromide or copper(I) iodide; process c) could also be carried out using the ester of formula (XII) such as an aryl-nitrile or trifluoromethyl derivative, followed by conversion to a carboxylic acid and amide formation as previously described;

compounds of the formula (X) are commercially available or can be prepared from commercially available materials by processes well known to those skilled in the art, for example functional group interconversions (such as hydrolysis, hydrogenation, hydrogenolysis, oxidation or reduction), and/or further functionalisation and/or cyclisation by standard reactions (such as amide or sulphonamide or metal-catalysed coupling, or nucleophilic displacement or electrophilic substitution reactions);

for example, by addition of a formyl group to a hydroxybenzamide compound as shown below:

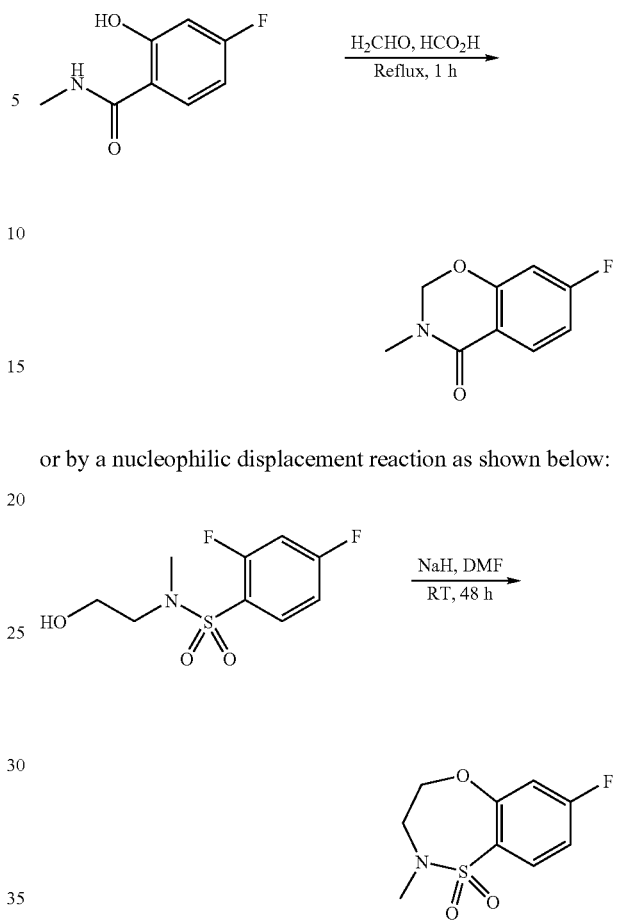

or by a nucleophilic displacement reaction as shown below:

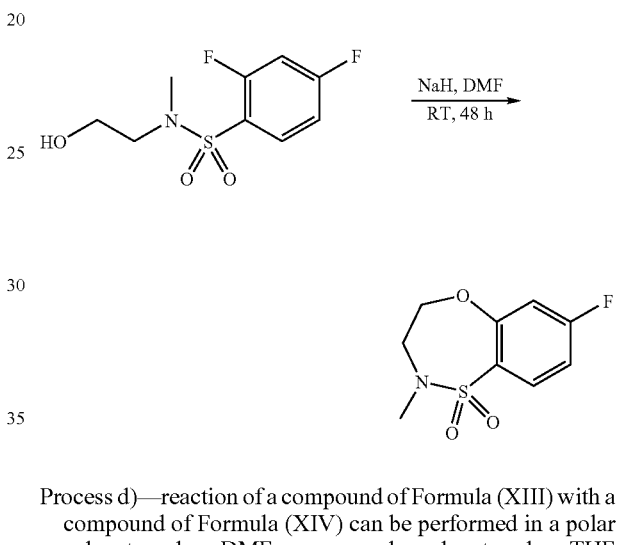

Process d)—reaction of a compound of Formula (XIII) with a compound of Formula (XIV) can be performed in a polar solvent, such as DMF or a non-polar solvent such as THF with a strong base, such as sodium hydride or potassium tert-butoxide at a temperature between 0 and 200° C., optionally using microwave heating or metal catalysis, such as palladium(II) acetate, palladium on carbon, copper (II) acetate or copper(I) iodide;

Process e)—coupling reactions of amino groups with carboxylic or sulfonic acids or acid derivatives to form an amide are well known in the art and are described above for Process a).

Process f)—cyclisations of a compound of formula (XVI) to a compound of formula (I) are well known in the art; for example, i) a coupling reaction of amino groups with carboxylic acids using coupling reagents or acid chlorides (see process a) to form amide bonds;

ii) a coupling reaction of an amino group with a sulphonyl chloride in the presence of a suitable base, such as pyridine or triethylamine, in a suitable solvent such as DCM, toluene or pyridine at a temperature between 0° C. and 80° C., to form a sulphonamide group;

iii) reaction with a suitable solvent, such as DMF or tetrahydrofuran (THF), with a base such as sodium hydride or potassium tert-butoxide, at a temperature in the range 0 to 200° C., optionally using microwave heating or metal catalysis such as palladium(II) acetate, palladium on carbon, copper(II) acetate or copper(I) iodide; alternatively, reaction in a suitable solvent, such as THF or DCM, with a suitable phosphine such as triphenylphosphine, and azodicarboxylate such as diethylazodicarboxylate;

iv) electrophilic substitution reactions (such as Friedel Crafts reactions, for compounds of Formula (XVI) where either $Y^1$ is a direct bond and $X^6$=H or $Y^2$ is a direct bond and $X^7$ is H);

compounds of the Formula (XVI) may be made from compounds of Formula (XVII), wherein each R group is independently a simple substituent (such as halo or cyano) or hydrogen, by processes well known to those skilled in the art such as functional group interconversions (for example hydrolysis, hydrogenation, hydrogenolysis, oxidation or reduction), and/or further functionalisation by standard reactions (such as amide or sulphonamide or metal-catalysed coupling, or nucleophilic displacement or electrophilic substitution reactions); compounds of formula (XVII) may be made from commercially available materials by processes such as those described herein in processes a) to e).

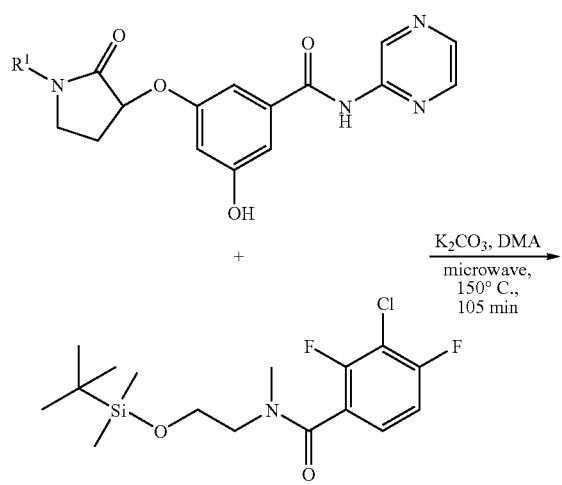

(XVII)

It will be appreciated that it is possible to form Ring C from a pre-cursor and form the phenoxy link in a one-pot reaction, so that it is unclear whether process c) or process e) is actually the final step. This is illustrated in the scheme below (for Ring B=phenyl) which illustrates that the $S_NAr$ reaction, deprotection and cyclisation to form Ring C may occur in the same reaction pot:

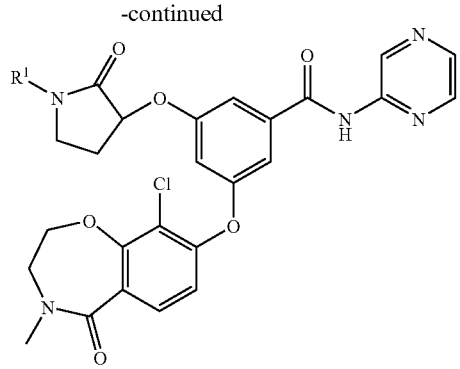

Rearrangement of Ring C may also occur in some circumstances, for example it may occur in the following circumstances:

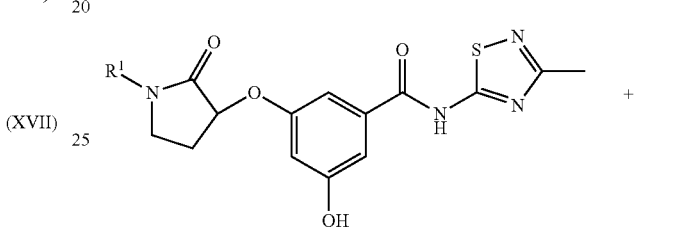

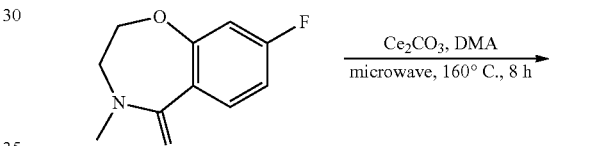

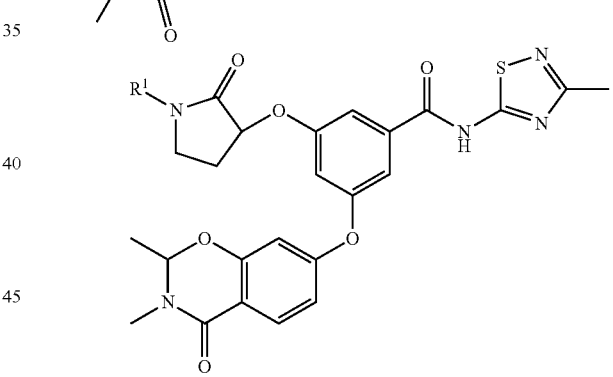

Certain intermediates of formula (V), (VII), (XI), (XII), (XIII), (XV), (XVI) and/or (XVII) wherein $R^1$ is as defined herein for a compound of formula (I) are believed to be novel and comprise an independent aspect of the invention.

During the preparation process, it may be advantageous to use a protecting group for a functional group within the molecule. Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Specific examples of protecting groups are given below for the sake of convenience, in which "lower" signifies that the group to which it is applied preferably has 1-4 carbon atoms. It will be understood that these examples are not exhaustive. Where specific examples of methods for the removal of protecting groups are given below these are similarly not exhaustive. The use of protecting groups and methods of deprotection not specifically mentioned is of course within the scope of the invention.

A carboxy protecting group may be the residue of an ester-forming aliphatic or araliphatic alcohol or of an ester-forming silanol (the said alcohol or silanol preferably containing 1-20 carbon atoms). Examples of carboxy protecting groups include straight or branched chain (1-12C)alkyl groups (e.g. isopropyl, t-butyl); lower alkoxy lower alkyl groups (e.g. methoxymethyl, ethoxymethyl, isobutoxymethyl); lower aliphatic acyloxy lower alkyl groups, (e.g. acetoxymethyl, propionyloxymethyl, butyryloxymethyl, pivaloyloxymethyl); lower alkoxycarbonyloxy lower alkyl groups (e.g. 1-methoxycarbonyloxyethyl, 1-ethoxycarbonyloxyethyl); aryl lower alkyl groups (e.g. p-methoxybenzyl, o-nitrobenzyl, p-nitrobenzyl, benzhydryl and phthalidyl); tri(lower alkyl) silyl groups (e.g. trimethylsilyl and t-butyldimethylsilyl); tri (lower alkyl)silyl lower alkyl groups (e.g. trimethylsilylethyl); and (2-6C)alkenyl groups (e.g. allyl and vinylethyl).

Methods particularly appropriate for the removal of carboxyl protecting groups include for example acid-, metal- or enzymically-catalysed hydrolysis. Hydrogenation may also be used.

Examples of hydroxy protecting groups include methyl, t-butyl, lower alkenyl groups (e.g. allyl); lower alkanoyl groups (e.g. acetyl); lower alkoxycarbonyl groups (e.g. t-butoxycarbonyl); lower alkenyloxycarbonyl groups (e.g. allyloxycarbonyl); aryl lower alkoxycarbonyl groups (e.g. benzoyloxycarbonyl, p-methoxybenzyloxycarbonyl, o-nitrobenzyloxycarbonyl, p-nitrobenzyloxycarbonyl); tri lower alkyl/arylsilyl groups (e.g. trimethylsilyl, t-butyldimethylsilyl, t-butyldiphenylsilyl); tetrahydropyran-2-yl; aryl lower alkyl groups (e.g. benzyl) groups; and triaryl lower alkyl groups (e.g. triphenylmethyl). Examples of amino protecting groups include formyl, aralkyl groups (e.g. benzyl and substituted benzyl, e.g. p-methoxybenzyl, nitrobenzyl and 2,4-dimethoxybenzyl, and triphenylmethyl); di-p-anisylmethyl and furylmethyl groups; lower alkoxycarbonyl (e.g. t-butoxycarbonyl); lower alkenyloxycarbonyl (e.g. allyloxycarbonyl); aryl lower alkoxycarbonyl groups (e.g. benzyloxycarbonyl, p-methoxybenzyloxycarbonyl, o-nitrobenzyloxycarbonyl, p-nitrobenzyloxycarbonyl; trialkylsilyl (e.g. trimethylsilyl and t-butyldimethylsilyl); alkylidene (e.g. methylidene); benzylidene and substituted benzylidene groups.

Methods appropriate for removal of hydroxy and amino protecting groups include, for example, hydrogenation, nucleophilic displacement, acid-, base, metal- or enzymically-catalysed hydrolysis, catalytic hydrogenolysis or photolytically for groups such as o-nitrobenzyloxycarbonyl, or with fluoride ions for silyl groups. For example, methylether protecting groups for hydroxy groups may be removed by trimethylsilyliodide. A tert-butyl ether protecting group for a hydroxy group may be removed by hydrolysis, for example by use of hydrochloric acid in methanol.

Examples of protecting groups for amide groups include aralkoxymethyl (e.g. benzyloxymethyl and substituted benzyloxymethyl); alkoxymethyl (e.g. methoxymethyl and trimethylsilylethoxymethyl); tri alkyl/arylsilyl (e.g. trimethylsilyl, t-butyldimethylsily, t-butyldiphenylsilyl); tri alkyl/ arylsilyloxymethyl (e.g. 1-butyldimethylsilyloxymethyl, t-butyldiphenylsilyloxymethyl); 4-alkoxyphenyl (e.g. 4-methoxyphenyl); 2,4-di(alkoxy)phenyl (e.g. 2,4-dimethoxyphenyl); 4-alkoxybenzyl (e.g. 4-methoxybenzyl); 2,4-di(alkoxy)benzyl (e.g. 2,4-di(methoxy)benzyl); and alk-1-enyl (e.g. allyl, but-1-enyl and substituted vinyl e.g. 2-phenylvinyl).

Aralkoxymethyl, groups may be introduced onto the amide group by reacting the latter group with the appropriate aralkoxymethyl chloride, and removed by catalytic hydrogenation. Alkoxymethyl, tri alkyl/arylsilyl and tri alkyl/silyloxymethyl groups may be introduced by reacting the amide with the appropriate chloride and removing with acid; or in the case of the silyl containing groups, fluoride ions. The alkoxyphenyl and alkoxybenzyl groups are conveniently introduced by arylation or alkylation with an appropriate halide and removed by oxidation with ceric ammonium nitrate. Finally alk-1-enyl groups may be introduced by reacting the amide with the appropriate aldehyde and removed with acid.

In the above other pharmaceutical composition, process, method, use and medicament manufacture features, the alternative and preferred aspects and embodiments of the compounds of the invention described herein also apply.

The following examples are for illustration purposes and are not intended to limit the scope of this application. Each exemplified compound represents a particular and independent aspect of the invention. In the following non-limiting Examples, unless otherwise stated:

(i) evaporations were carried out by rotary evaporation under reduced pressure and work-up procedures were carried out after removal of residual solids such as drying agents by filtration;

(ii) operations were carried out at room temperature, that is in the range 18-25° C. and under an atmosphere of an inert gas such as argon or nitrogen;

(iii) yields are given for illustration only and are not necessarily the maximum attainable;

(iv) the structures of the end-products of the Formula (I) were confirmed by nuclear (generally proton) magnetic resonance (NMR) and mass spectral techniques; proton magnetic resonance chemical shift values were measured on the delta scale and peak multiplicities are shown as follows: s, singlet; d, doublet; t, triplet; m, multiplet; br, broad; q, quartet, quin, quintet;

(v) intermediates were not generally fully characterised and purity was assessed by thin layer chromatography (TLC), high-performance liquid chromatography (HPLC), infra-red (IR) or NMR analysis;

(vi) flash chromatography was carried out on silica unless otherwise stated.

| | Abbreviations |
|---|---|
| DCM | dichloromethane; |
| DEAD | diethylazodicarboxylate; |
| DMA | dimethylacetamide |
| DIAD | diisopropylazodicarboxylate; |
| DMSO | dimethyl sulphoxide; |
| DMF | dimethylformamide; |
| EDAC | 1-(3-dimemylaminopropyl)-3-ethylcarbodiimide hydrochloride; |
| HPLC | high pressure liquid chromatography |
| HPMC | Hydroxypropylmethylcellulose; |
| LCMS | liquid chromatography/mass spectroscopy; |
| NMR | nuclear magnetic resonance spectroscopy |
| RT | room temperature; and |
| THF | tetrahydrofuran |

EXAMPLE 1

3-[6-(Azetidine-1-carbonyl)pyridin-3-yl]oxy-5-[(3S)-1-methyl-2-oxo-pyrrolidin-3-yl]oxy-N-(5-methylpyrazin-2-yl)benzamide

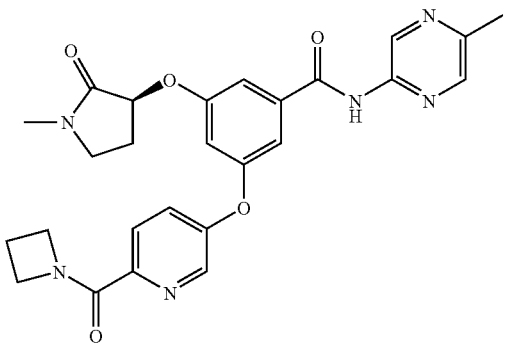

3-[6-(Azetidine-1-carbonyl)pyridin-3-yl]oxy-5-hydroxy-N-(5-methylpyrazin-2-yl)benzamide (442 mg, 1.1 mmol) (Intermediate 1) and 3-bromo-1-methyl-pyrrolidin-2-one (Intermediate 4) (385 mg, 2.2 mmol) were dissolved in DMF and treated with potassium carbonate (377 mg, 2.7 mmol) and stirred at room temperature for 21 hours. The DMF was evaporated, the residue partitioned between ethyl acetate (90 mL) and water (20 mL). The organic layer was separated, washed with brine, dried (MgSO$_4$) and evaporated to give an oil which was purified by chromatography on silica eluting with 0-6% methanol in DCM to give the racemic product (420 mg). 3-[6-(Azetidine-1-carbonyl)pyridin-3-yl]oxy-5-[(3S)-1-methyl-2-oxo-pyrrolidin-3-yl]oxy-N-(5-methylpyrazin-2-yl)benzamide was separated from its enantiomer by chiral HPLC using a Merck 50 mm 20 μm Chiralcel OJ No. CE001 column eluting with methanol at a flow rate of 50 mL/min; 420 mg of racemic material was separated in 3 injections of 15 mL at 11 mg/ml in 1:1:1 acetonitrile/ethanol/methanol to afford the product (179 mg, 32%) which eluted after its enantiomer. $^1$H NMR δ (400 MHz, CDCl$_3$): 2.08-2.18 (m, 1H), 2.28 (quintet, 2H), 2.47-2.57 (m, 1H), 2.48 (s, 3H), 2.86 (s, 3H), 3.29-3.37 (m, 1H), 3.42-3.48 (m, 1H), 4.18 (t, 2H), 4.64 (t, 2H), 4.86 (t, 1H), 6.91 (s, 1H), 7.14 (s, 1H), 7.32 (d, 1H), 7.39 (s, 1H), 8.05 (d, 1H), 8.07 (s, 1H), 8.26 (s, 1H), 8.37 (s, 1H), 9.45 (s, 1H); m/z 503 (M+H)$^+$

EXAMPLE 2

3-[6-(Azetidine-1-carbonyl)pyridin-3-yl]oxy-5-[(3R)-1-methyl-2-oxo-pyrrolidin-3-yl]oxy-N-(5-methylpyrazin-2-yl)benzamide

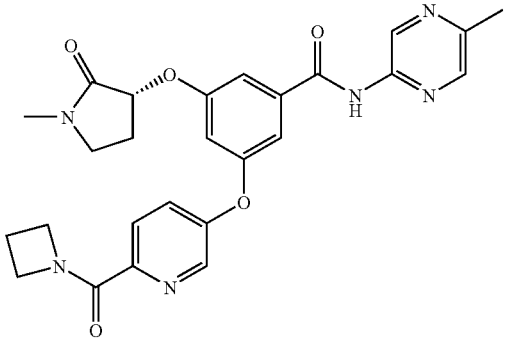

3-[6-(Azetidine-1-carbonyl)pyridin-3-yl]oxy-5-hydroxy-N-(5-methylpyrazin-2-yl)benzamide (442 mg, 1.1 mmol) (Intermediate 1) and 3-bromo-1-methyl-pyrrolidin-2-one (385 mg, 2.2 mmol) (Intermediate 4) were dissolved in DMF and treated with potassium carbonate (377 mg, 2.7 mmol) and stirred at room temperature for 21 hours. The DMF was evaporated, the residue was partitioned between ethyl acetate (90 mL) and water (20 mL). The organic layer was separated, washed with brine, dried (MgSO$_4$) and evaporated to give an oil which was purified by chromatography on silica eluting with 0-6% methanol in DCM to give the racemic product (420 mg). 3-[6-(Azetidine-1-carbonyl)pyridin-3-yl]oxy-5-[(3R)-1-methyl-2-oxo-pyrrolidin-3-yl]oxy-N-(5-methylpyrazin-2-yl)benzamide was separated from its enantiomer by chiral HPLC using a Merck 50 mm 20 μm Chiralcel OJ No. CE001 column eluting with methanol at a flow rate of 50 mL/min; 420 mg of racemic material was separated in 3 injections of 15 mL at 11 mg/ml in 1:1:1 acetonitrile/ethanol/methanol to afford the product (187 mg, 33%) which eluted before its enantiomer. $^1$H NMR δ (400 MHz, CDCl$_3$): 2.08-2.18 (m, 1H), 2.28 (quintet, 2H), 2.47-2.57 (m, 1H), 2.48 (s, 3H), 2.86 (s, 3H), 3.29-3.37 (m, 1H), 3.42-3.48 (m, 1H), 4.18 (t, 2H), 4.64 (t, 2H), 4.86 (t, 1H), 6.91 (s, 1H), 7.14 (s, 1H), 7.32 (d, 1H), 7.39 (s, 1H), 8.05 (d, 1H), 8.07 (s, 1H), 8.26 (s, 1H), 8.37 (s, 1H), 9.45 (s, 1H); m/z 503 (M+H)$^+$

EXAMPLE 3

3-[5-(Azetidine-1-carbonyl)pyrazin-2-yl]oxy-5-[(3S)-1-methyl-2-oxo-pyrrolidin-3-yl]oxy-N-(4-methyl1,3-thiazol-2-yl)benzamide

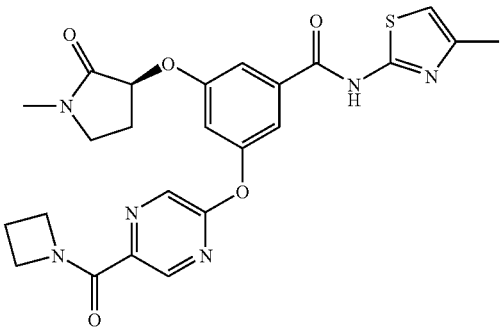

1-Chloro-N,N,2-trimethyl-prop-1-en-1-amine (0.10 mL, 0.75 mmol) was added to a solution of the 3-[5-(azetidine-1-carbonyl)pyrazin-2-yl]oxy-5-[(3S)-1-methyl-2-oxo-pyrrolidin-3-yl]oxy-benzoic acid (Intermediate 6) (265 mg, 0.62 mmol) in DCM (5 mL) and stirred at ambient temperature for 30 minutes, a further aliquot of 1-chloro-N,N,2-trimethyl-prop-1-en-1-amine (0.10 mL) was added and stirring continued for a further 30 minutes. 4-Methyl-1,3-thiazol-2-amine (142 mg, 1.2 mmol) and pyridine (0.10 mL, 1.2 mmol) were added and the reaction stirred for 16 hours. The solvent was evaporated under reduced pressure. The residue was dissolved in ethyl acetate (15 mL) and DCM (15 mL), washed with water (2×10 mL) and brine (10 mL), dried (MgSO$_4$), filtered and evaporated under reduced pressure to give the crude product which was purified by flash chromatography on silica, eluting with a gradient of 0-5% methanol in DCM, to afford the product (181 mg, 58%). $^1$H NMR δ (300 MHz, CDCl$_3$) 2.10-2.26 (m, 4H), 2.38 (quintet, 2H), 2.50-2.63 (m, 1H), 2.93 (s, 3H), 3.33-3.56 (m, 2H), 4.26 (t, 2H), 4.69 (t, 2H), 4.84 (t, 1H), 6.54 (s, 1H), 7.15 (s, 1H), 7.36 (s, 1H), 7.53 (s, 1H), 8.32 (s, 1H), 8.82 (s, 1H), 10.43 (s, 1H); m/z 509 (M+H)+

EXAMPLE 4

3-[5-(Azetidine-1-carbonyl)pyrazin-2-yl]oxy-5-[(3R)-1-methyl-2-oxo-pyrrolidin-3-yl]oxy-N-(4-methyl1,3-thiazol-2-yl)benzamide

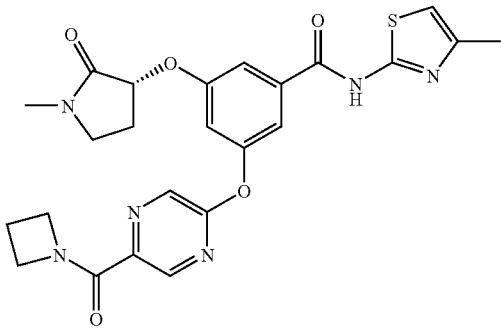

1-Chloro-N,N,2-trimethyl-prop-1-en-1-amine (0.16 mL, 1.2 mmol) was added to a solution of 3-[5-(azetidine-1-carbonyl)pyrazin-2-yl]oxy-5-(1-methyl-2-oxo-pyrrolidin-3-yl)oxy-benzoic acid (Intermediate 10) (288 mg, 0.68 mmol) in DCM (5 mL) and stirred at ambient temperature for 30 minutes. 4-Methyl-1,3-thiazol-2-amine (156 mg, 1.36 mmol) and pyridine (0.11 mL, 1.4 mmol) were added and the reaction stirred for 16 hours. The solvent was evaporated under reduced pressure. The residue dissolved in ethyl acetate (30 mL), washed with water (2×10 mL) and brine (10 mL), dried (MgSO₄), filtered and evaporated under reduced pressure. The residue was purified by flash chromatography on silica, eluting with a gradient of 0-5% methanol in DCM, to afford the product (117 mg, 34%). ¹H NMR δ (300 MHz, CDCl₃) 2.10-2.26 (m, 4H), 2.38 (quintet, 2H), 2.50-2.63 (m, 1H), 2.93 (s, 3H), 3.33-3.56 (m, 2H), 4.26 (t, 2H), 4.69 (t, 2H), 4.84 (t, 1H), 6.54 (s, 1H), 7.15 (s, 1H), 7.36 (s, 1H), 7.53 (s, 1H), 8.32 (s, 1H), 8.82 (s, 1H), 10.43 (s, 1H); m/z 509 (M+H)+

EXAMPLE 5

3-[4-(Azetidine-1-carbonyl)phenoxy]-5-[(3S)-1-methyl-2-oxo-pyrrolidin-3-yl]oxy-N-(1H-pyrazol-3-yl)benzamide

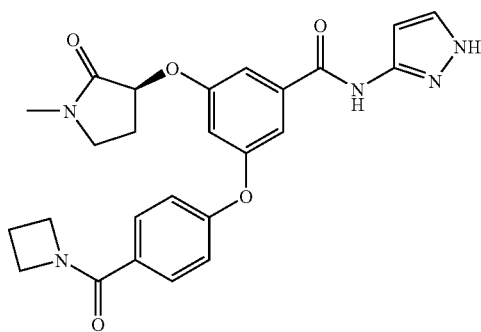

Tert-butyl 3-[[3-[4-(azetidine-1-carbonyl)phenoxy]-5-[(3S)-1-methyl-2-oxo-pyrrolidin-3-yl]oxy-benzoyl]amino]pyrazole-1-carboxylate (Intermediate 14) (388 mg, 0.67 mmol) was dissolved in acetonitrile (5 mL) and heated in a microwave for 12 minutes at 150° C., the solution was concentrated under reduced pressure to afford the product (261 mg, 82%). ¹H NMR δ (300 MHz, CDCl₃) 2.06-2.21 (m, 1H), 2.34 (quintet, 2H), 2.49-2.63 (m, 1H), 2.92 (s, 3H), 3.31-3.52 (m, 2H), 4.15-4.38 (m, 4H), 4.87 (t, 1H), 6.77 (s, 1H), 6.80 (s, 1H), 6.98 (d, 2H), 7.17 (s, 1H), 7.38 (s, 1H), 7.48 (s, 1H), 7.61 (d, 2H), 10.29 (s, 1H); m/z 476 (M+H)⁺.

EXAMPLE 6

3-[5-(Azetidine-1-carbonyl)-3-chloro-pyridin-2-yl]oxy-5-[(3S)-1-methyl-2-oxo-pyrrolidin-3-yl]oxy-N-(5-methylpyrazin-2-yl)benzamide

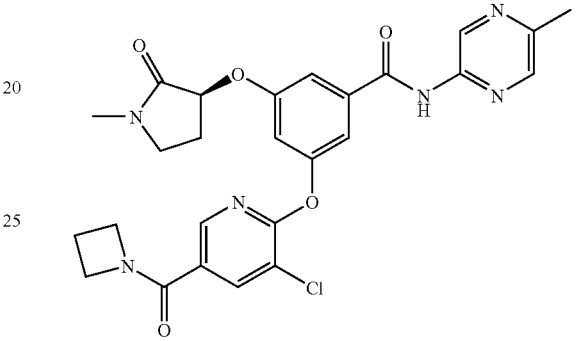

A mixture of 3-hydroxy-5-[(3S)-1-methyl-2-oxo-pyrrolidin-3-yl]oxy-N-(5-methylpyrazin-2-yl)benzamide (Intermediate 18) (136 mg, 0.4 mmol), azetidin-1-yl-(5,6-dichloropyridin-3-yl)methanone (Intermediate 21) (103 mg, 0.44 mmol) and potassium carbonate (111 mg, 0.8 mmol) in DMA (5 mL) was stirred at 120° C. for 2 hours. The solution was evaporated under reduced pressure, the residue dissolved in ethyl acetate (40 mL) washed with water (2×20 mL), brine (20 mL), dried (MgSO₄), filtered and the solvent removed under reduced pressure. The residue was purified by flash chromatography on silica, eluting with a gradient of 0-4% methanol in DCM to afford the product (188 mg, 87%). ¹H NMR δ (300 MHz, CDCl₃) 2.16-2.29 (m, 1H), 2.40 (quintet, 2H), 2.50-2.72 (m, 4H), 2.95 (s, 3H), 3.36-3.58 (m, 2H), 4.18-4.42 (m, 4H), 4.95 (t, 1H), 7.15 (s, 1H), 7.37 (s, 1H), 7.55 (s, 1H), 8.15 (s, 2H), 8.25 (s, 1H), 8.55 (s, 1H), 9.54 (s, 1H); m/z 537 (M+H)⁺.

EXAMPLE 7

3-[(3S)-1-Methyl-2-oxo-pyrrolidin-3-yl]oxy-N-(5-methylpyrazin-2-yl)-5-(4-methylsulfonylphenoxy)benzamide

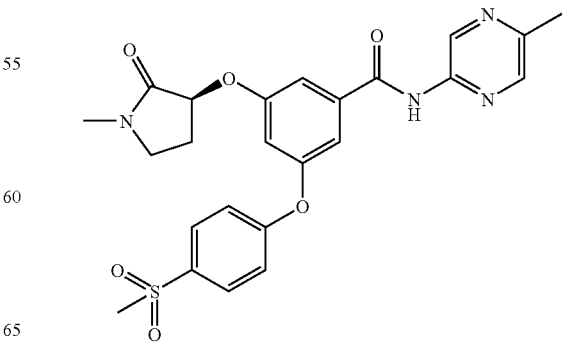

A mixture of 3-hydroxy-5-[(3S)-1-methyl-2-oxo-pyrrolidin-3-yl]oxy-N-(5-methylpyrazin-2-yl)benzamide (Intermediate 18) (136 mg, 0.4 mmol), 1-fluoro-4-methylsulfonylbenzene (105 mg, 0.6 mmol) and potassium carbonate (111 mg, 0.8 mmol) in DMA (5 mL) was stirred at 120° C. for 2 hours. The solution was evaporated under reduced pressure, the residue dissolved in ethyl acetate (40 mL), washed with water (2×20 mL), brine (20 mL), dried (MgSO$_4$), filtered and the solvent removed under reduced pressure. The residue was purified by flash chromatography on silica, eluting with a gradient of 0-4% methanol in DCM to afford product (135 mg, 68%). $^1$H NMR δ (300 MHz, CDCl$_3$) 2.15-2.30 (m, 1H), 2.53-2.69 (m, 4H), 2.94 (s, 3H), 3.08 (s, 3H), 3.36-3.58 (m, 2H), 4.96 (t, 1H), 7.02 (s, 1H), 7.15 (d, 2H), 7.25 (s, 1H), 7.50 (s, 1H), 7.93 (d, 2H), 8.15 (s, 1H), 8.55 (s, 1H), 9.53 (s, 1H); m/z 497 (M+H)$^+$.

EXAMPLE 8

3-[4-(Azetidine-1-carbonyl)phenoxy]-5-[(3S)-1-methyl-2-oxo-pyrrolidin-3-yl]oxy-N-(5-methylpyrazin-2-yl)benzamide

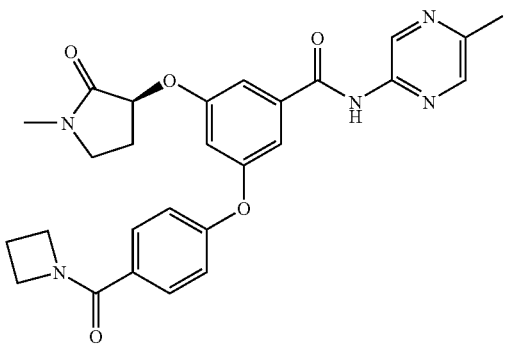

A solution of 3-[4-(azetidine-1-carbonyl)-2-chloro-phenoxy]-5-[(3S)-1-methyl-2-oxo-pyrrolidin-3-yl]oxy-N-(5-methylpyrazin-2-yl)benzamide (Intermediate 22) (120 mg, 0.22 mmol) and 10% palladium on carbon (20 mg, catalytic) in THF (5 mL) and ethanol (5 mL) was stirred under an atmosphere of hydrogen for 16 hours. The palladium on carbon was removed by filtration and the filtrate evaporated under reduced pressure. The residue was dissolved in ethyl acetate (30 mL), washed with water (10 mL), brine (10 mL), dried (MgSO$_4$), filtered and evaporated under reduced pressure to give product (98 mg, 89%). $^1$H NMR δ (300 MHz, CDCl$_3$) 2.12-2.26 (m, 1H), 2.36 (quintet, 2H), 2.52-2.67 (m, 4H), 2.94 (s, 3H), 3.35-3.57 (m, 2H), 4.19-4.42 (m, 4H), 4.93 (t, 1H), 6.93 (s, 1H), 7.03 (d, 2H), 7.20 (s, 1H), 7.42 (s, 1H), 7.66 (d, 2H), 8.15 (s, 1H), 8.54 (s, 1H), 9.52 (s, 1H); m/z 502 (M+H)$^+$.

EXAMPLE 9

3-[(2,2-Dioxo-6-oxa-2-λ$^6$-thiabicyclo[5.4.0]undeca-7,9,11-trien-9-yl)oxy]-5-[(3S)-1-methyl-2-oxo-pyrrolidin-3-yl]oxy-N-(5-methylpyrazin-2-yl)benzamide

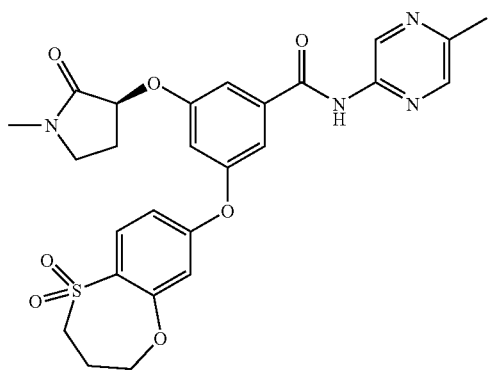

3-Hydroxy-5-[(3S)-1-methyl-2-oxo-pyrrolidin-3-yl]oxy-N-(5-methylpyrazin-2-yl)benzamide (Intermediate 18) (171 mg, 0.5 mmol), 9-fluoro-6-oxa-2-X$^6$-thiabicyclo[5.4.0]undeca-7,9,11-triene 2,2-dioxide (Intermediate 23) (130 mg, 0.6 mmol) and potassium carbonate (139 mg, 1 mmol) in acetonitrile (5 mL) were heated in a microwave at 160° C. for 5 hours. The precipitate was filtered and purified by column chromatography on silica eluting with 0-4% methanol/DCM to give product (204 mg, 76%). $^1$H NMR δ (300 MHz, CDCl$_3$) 2.13-2.28 (m, 1H), 2.37-2.48 (m, 2H), 2.53-2.68 (m, 4H), 2.94 (s, 3H), 3.31-3.57 (m, 4H), 4.26 (t, 2H), 4.94 (t, 1H), 6.76 (s, 1H), 6.87 (d, 1H), 6.99 (s, 1H), 7.24 (s, 1H), 7.50 (s, 1H), 7.93 (d, 1H), 8.13 (s, 1H), 8.55 (s, 1H), 9.52 (s, 1H); m/z 539 (M+H)$^+$.

EXAMPLE 10

3-[6-(Azetidine-1-carbonyl)pyridin-3-yl]oxy-5-(1-ethyl-2-oxo-pyrrolidin-3-yl)oxy-N-(5-methylpyrazin-2-yl)benzamide

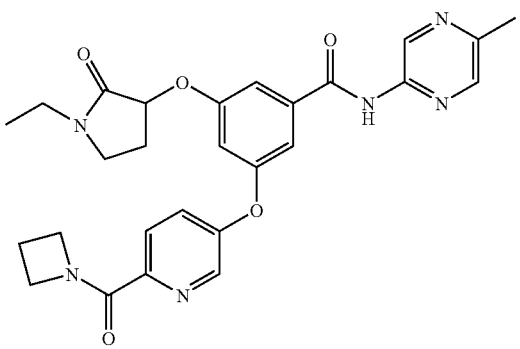

Ethyl 2-[3-[6-(azetidine-1-carbonyl)pyridin-3-yl]oxy-5-[(5-methylpyrazin-2-yl)carbamoyl]phenoxy]-4-methylsulfonyloxy-butanoate (Intermediate 27) (27 mg, 0.04 mmol), sodium iodide (7 mg, 0.04 mmol) and ethylamine (2M in THF; 45 µL, 0.09 mmol) in acetonitrile (2 mL) were heated in a microwave at 120° C. for 90 minutes. Solvent evaporated under reduced pressure and the residue diluted with ethyl acetate (20 mL) and brine (20 mL). The organics were separated and the aqueous layer re-extracted with ethyl acetate (20 mL). The combined organics were dried (MgSO$_4$) and concentrated and the residue purified by preparative HPLC, eluting with a gradient of 5 to 95% acetonitrile in water containing 0.2% trifluoroacetic acid on a Phenomenex Luna 10u C18(2) 100A column, to afford product (24 mg, 87%). $^1$H NMR δ (300 MHz, CDCl$_3$) 1.19 (3H, t), 2.17-2.26 (1H, m), 2.34-2.44 (2H, m), 2.62-2.74 (4H, m), 3.39-3.59 (4H, m), 4.30 (2H, s), 4.76 (2H, s), 5.11 (1H, t), 6.95 (1H, t), 7.29 (1H, t), 7.39-7.42 (1H, m), 7.52 (1H, d), 8.10 (1H, d), 8.19 (1H, s), 8.36 (1H, d), 9.65 (1H, d); m/z 517 (M+H)$^+$.

EXAMPLE 11

3-[(5-methy-6,6-dioxo-2-oxa-6-λ$^6$-thia-5-azabicyclo[5.4.0]undeca-8,10,12-trien-10-yl)oxy]-5-(1-methyl-2-oxo-pyrrolidin-3-yl)oxy-N-(5-methylpyrazin-2-yl)benzamide

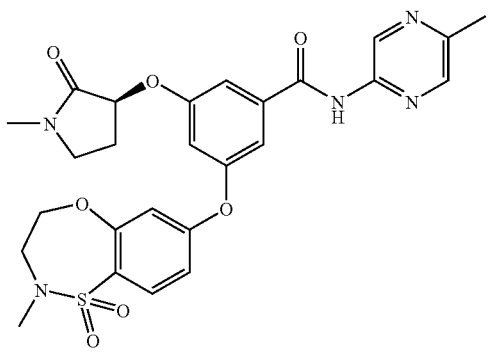

3-Hydroxy-5-(1-methyl-2-oxo-pyrrolidin-3-yl)oxy-N-(5-methylpyrazin-2-yl)benzamide (Intermediate 18) (0.279 g, 0.82 mmol), 10-fluoro-5-methyl-2-oxa-6-λ$^6$-thia-5-azabicyclo[5.4.0]undeca-8,10,12-triene 6,6-dioxide (Intermediate 35) (0.227 g, 0.98 mmol) and potassium carbonate (0.226 g, 1.63 mmol) were dissolved in acetonitrile (5 mL) and heated in a microwave at 160° C. for 10 hours. The solvent was removed under reduced pressure and water (20 mL) and ethyl acetate (50 mL) was added. The ethyl acetate layer was separated, washed with brine (50 mL), dried (MgSO$_4$) and concentrated under reduced pressure. The residue was purified by chromatography on silica eluting with 0-4% methanol/DCM to give product (253 mg, 56%). $^1$H NMR δ (300 MHz, CDCl$_3$) 2.14-2.29 (m, 1H), 2.54-2.67 (m, 4H), 2.82 (s, 3H), 2.93 (s, 3H), 3.35-3.58 (m, 2H), 3.74 (t, 2H), 4.21 (t, 2H), 4.94 (t, 1H), 6.76 (s, 1H), 6.84 (d, 1H), 6.99 (s, 1H), 7.25 (s, 1H), 7.49 (s, 1H), 7.79 (d, 1H), 8.14 (s, 1H), 8.53 (s, 1H), 9.53 (s, 1H); m/z 554 (M+H)$^+$.

EXAMPLE 12

3-[6-(Azetidine-1-carbonyl)pyridin-3-yl]oxy-5-[(3S)-1-methyl-2-oxo-pyrrolidin-3-yl]oxy-N-pyrazin-2-yl-benzamide

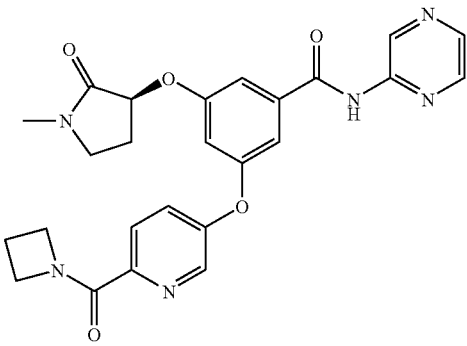

1-Chloro-N,N,2-trimethyl-prop-1-en-1-amine (0.08 0 mL, 0.60 mmol) was added to a solution of 3-[6-(azetidine-1-carbonyl)pyridin-3-yl]oxy-5-[(3S)-1-methyl-2-oxo-pyrrolidin-3-yl]oxy-benzoic acid (Intermediate 30) (202 mg, 0.49 mmol) in DCM (5 mL) and stirred at ambient temperature for 50 minutes. 2-Amino-pyrazine (CAS no. 5049-61-6) (94 mg, 0.98 mmol) and pyridine (0.80 mL, 0.98 mmol) were added and the reaction stirred for 16 hours. The solvent was removed under reduced pressure and the residue taken up in ethyl acetate (40 mL), washed with saturated sodium bicarbonate (20 mL), water (10 mL), and brine (10 mL), dried (MgSO$_4$) and evaporated under reduced pressure to give the crude product. The residue was purified by chromatography on silica, eluting with a gradient of 0-4% methanol in DCM to give product (53 mg, 22%). $^1$H NMR δ300 MHz, CDCl$_3$) 2.13-2.27 (m, 1H), 2.35 (quintet, 2H), 2.52-2.67 (m, 1H), 2.93 (s, 3H), 3.34-3.59 (m, 2H), 4.24 (t, 2H), 4.70 (t, 2H), 4.94 (t, 1H), 6.98 (s, 1H), 7.23 (s, 1H), 7.39 (d, 1H), 7.48 (s, 1H), 8.12 (d, 1H), 8.27 (q, 1H), 8.33 (d, 1H), 8.39 (d, 1H), 8.66 (s, 1H), 9.66 (s, 1H); m/z 489 (M+H)$^+$.

EXAMPLE 13

3-[6-(Azetidine-1-carbonyl)pyridin-3-yl]oxy-5-[(3S)-1-methyl-2-oxo-pyrrolidin-3-yl]oxy-N-pyridin-2-yl-benzamide

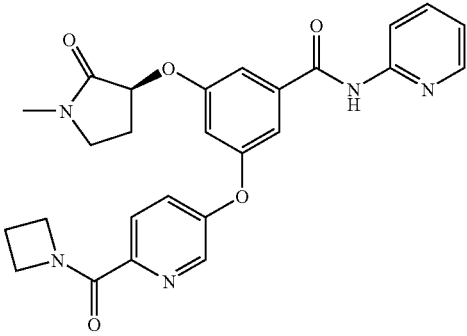

1-Chloro-N,N,2-trimethyl-prop-1-en-1-amine (0.077 mL, 0.58 mmol) was added to a solution of 3-[6-(azetidine-1-carbonyl)pyridin-3-yl]oxy-5-[(3S)-1-methyl-2-oxo-pyrrolidin-3-yl]oxy-benzoic acid (Intermediate 30) (200 mg, 0.49 mmol) in DCM (5 mL) and stirred at ambient temperature for 50 minutes. 2-Amino-pyridine (93 mg, 0.98 mmol) and pyridine (0.080 mL, 0.98 mmol) were added and the reaction stirred for 16 hours. The solvent was removed under reduced pressure and the residue was dissolved in ethyl acetate (40 mL), washed with water (10 mL), and brine (10 mL), dried (MgSO$_4$) and evaporated under reduced pressure. The residue was purified by flash chromatography, eluting with a gradient of 0-100% methanol in DCM to afford the product (112 mg, 47%). $^1$H NMR δ (300 MHz, CDCl$_3$) 2.12-2.26 (m, 1H), 2.35 (quintet, 2H), 2.53-2.66 (m, 1H), 2.93 (s, 3H), 3.34-3.57 (m, 2H), 4.25 (t, 2H), 4.70 (t, 2H), 4.93 (t, 1H), 6.97 (s, 1H), 7.08 (t, 1H), 7.22 (s, 1H), 7.38 (d, 1H), 7.45 (s, 1H), 7.75 (t, 1H), 8.11 (d, 1H), 8.29 (d, 1H), 8.33 (q, 2H), 8.68 (s, 1H); m/z 488 (M+H)$^+$.

EXAMPLE 14

3-[(11-Chloro-5-methyl-6-oxo-2-oxa-5-azabicyclo[5.4.0]undeca-8,10,12-trien-10-yl)oxy]-5-[(3S)-1-methyl-2-oxo-pyrrolidin-3-yl]oxy-N-(5-methylpyrazin-2-yl)benzamide

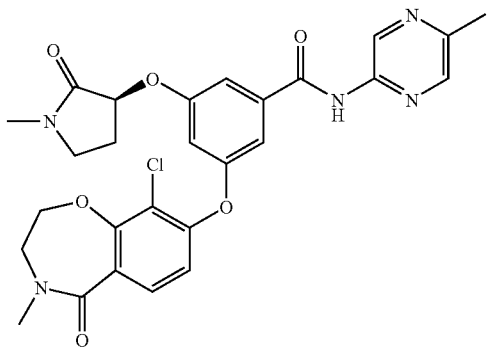

A mixture of 3-hydroxy-5-[(3S)-1-methyl-2-oxo-pyrrolidin-3-yl]oxy-N-(5-methylpyrazin-2-yl)benzamide (Intermediate 18) (137 mg, 0.4 mmol), 3-chloro-2,4-difluoro-N-(2-hydroxyethyl)-N-methyl-benzamide (Intermediate 37) (151 mg, 0.6 mmol) and potassium carbonate (111 mg, 0.8 mmol) in acetonitrile (5 mL) was stirred at 160° C. for 6 hours. The solution was evaporated under reduced pressure, the residue dissolved in ethyl acetate (40 mL) washed with water (2×20 mL), brine (10 mL), dried (MgSO$_4$) and the solvent removed under reduced pressure. The residue was purified by chromatography on silica eluting with 0-4%% methanol/DCM to afford the crude product which was taken up in ethyl acetate and washed with 0.5N hydrochloric acid, dried (MgSO$_4$) and concentrated under reduced pressure to afford the product (50 mg, 23%). $^1$H NMR δ (300 MHz, CDCl$_3$) 2.12-2.25 (m, 1H), 2.52-2.66 (m, 4H), 2.93 (s, 3H), 3.24 (s, 3H), 3.35-3.55 (m, 2H), 3.59 (t, 2H), 4.54 (t, 2H), 4.92 (t, 1H), 6.83 (d, 1H), 6.90 (s, 1H), 7.17 (s, 1H), 7.41 (s, 1H), 7.71 (d, 1H), 8.13 (s, 1H), 8.52 (s, 1H), 9.52 (s, 1H); m/z 552 (M+H)$^+$.

EXAMPLE 15

3-[(4-Methyl-5-oxo-2-oxa-4-azabicyclo[4.4.0]deca-6,8,10-trien-9-yl)oxy]-5-(1-methyl-2-oxo-pyrrolidin-3-yl)oxy-N-(5-methylpyrazin-2-yl)benzamide

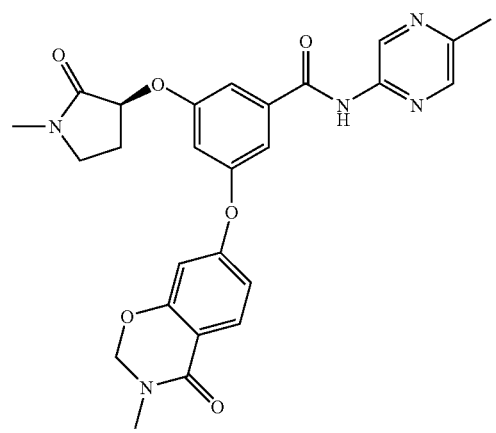

A mixture of 3-hydroxy-5-[(3S)-1-methyl-2-oxo-pyrrolidin-3-yl]oxy-N-(5-methylpyrazin-2-yl)benzamide (Intermediate 18) (279 mg, 0.82 mmol), 9-fluoro-4-methyl-2-oxa-4-azabicyclo[4.4.0]deca-7,9,11-trien-5-one (Intermediate 38) (163 mg, 0.9 mmol) and potassium carbonate (226 mg, 1.63 mmol) in acetonitrile (10 mL) was heated in a microwave at 160° C. for 12 hours. The solvent was evaporated under reduced pressure, ethyl acetate (50 mL) was added and the resulting mixture was washed with water (2×20 mL), 0.5N hydrochloric acid (5 mL), water (10 mL) and brine (20 mL), dried (MgSO$_4$) and evaporated under reduced pressure. The residue was purified by chromatography on silica eluting with 0-4% methanol in DCM to give product (138 mg, 33%). $^1$H NMR δ (300 MHz, CDCl$_3$) 2.13-2.28 (m, 1H), 2.53-2.68 (m, 4H), 2.93 (s, 3H), 3.10 (s, 3H), 3.35-3.57 (m, 2H), 4.93 (t, 1H), 5.17 (s, 2H), 6.54 (s, 1H), 6.75 (d, 1H), 6.97 (s, 1H), 7.21 (s, 1H), 7.46 (s, 1H), 7.94 (d, 1H), 8.14 (s, 1H), 8.50 (s, 1H), 9.52 (s, 1H); m/z 504 (M+H)$^+$.

EXAMPLE 16

3-[(5-Methyl-6-oxo-2-oxa-5-azabicyclo[5.4.0]undeca-8,10,12-trien-10-yl)oxy]-5-[(3S)-1-methyl-2-oxo-pyrrolidin-3-yl]oxy-N-(5-methylpyrazin-2-yl)benzamide

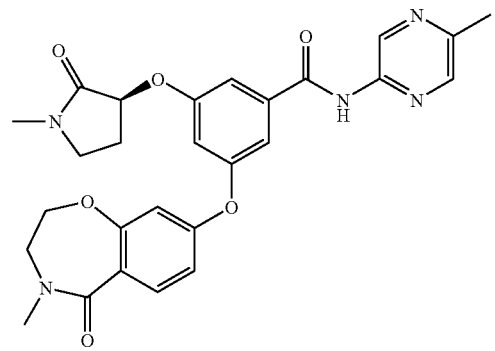

To a solution of 3-[(1'-chloro-5-methyl-6-oxo-2-oxa-5-azabicyclo[5.4.0]undeca-8,10,12-trien-10-yl)oxy]-5-[(3S)-1-methyl-2-oxo-pyrrolidin-3-yl]oxy-N-(5-methylpyrazin-2-yl)benzamide (Example 14, 50 mg, 0.09 mmol) in ethanol (5 mL) was added ammonium formate (57 mg, 0.90 mmol) followed by 10% palladium on carbon (10 mg, catalytic) was added. The mixture was heated to 140° C. for 60 minutes in a microwave. The catalyst was filtered off and the volatiles removed under reduced pressure. The residue was dissolved in ethyl acetate (30 mL), washed with water (10 mL), 0.5N hydrochloric acid (5 mL), saturated sodium bicarbonate (5 mL) and brine (10 mL), dried (MgSO$_4$) and evaporated under reduced pressure. The residue was purified by flash chromatography on silica eluting with 4% methanol in DCM to afford the product (18 mg, 39%). $^1$H NMR δ (300 MHz, CDCl$_3$) 2.11-2.26 (m, 1H), 2.53-2.67 (m, 4H), 2.94 (s, 3H), 3.21 (s, 3H), 3.35-3.55 (m, 2H), 3.58 (t, 2H), 4.41 (t, 2H), 4.94 (t, 1H), 6.59 (s, 1H), 6.78 (d, 1H), 6.95 (s, 1H), 7.23 (s, 1H), 7.44 (s, 1H), 7.88 (d, 1H), 8.13 (s, 1H), 8.66 (s, 1H), 9.53 (s, 1H); m/z 518 (M+H)$^+$.

EXAMPLE 17

3-[6-(Azetidine-1-carbonyl)pyridin-3-yl]oxy-5-(1-cyclobutyl-2-oxo-pyrrolidin-3-yl)oxy-N-(5-methylpyrazin-2-yl)benzamide

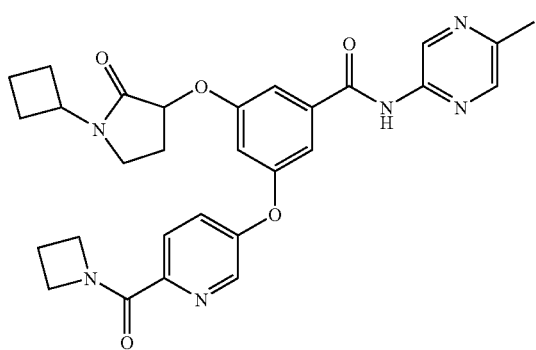

To a solution of ethyl 2-[3-[6-(azetidine-1-carbonyl)pyridin-3-yl]oxy-5-[(5-methylpyrazin-2-yl)carbamoyl]phenoxy]-4-methylsulfonyloxy-butanoate (Intermediate 27) (250 mg, 0.41 mmol) in acetonitrile (5 mL), was added sodium iodide (62 mg, 0.41 mmol) and cyclobutylamine (70 μL, 0.81 mmol). The resulting mixture was heated in a microwave at 120° C. for 60 minutes. The solvent was evaporated under reduced pressure and the residue purified by flash chromatography eluting with 0-40% methanol in DCM to afford the product (95 mg, 43%). $^1$H NMR δ (300 MHz, CDCl$_3$) 1.69-1.78 (2H, m), 2.13-2.23 (5H, m), 2.30-2.40 (2H, m), 2.55-2.64 (4H, m), 3.39-3.47 (1H, m), 3.57-3.64 (1H, m), 4.24 (2H t), 4.62-4.72 (3H, m), 4.91-4.96 (1H, m), 6.96 (1H, t), 7.22 (1H t), 7.36-7.40 (1H, m), 7.45 (1H, t), 8.09-8.13 (2H, m), 8.32 (1H, d), 8.61 (1H, s), 9.51 (1H, d); m/z 543 (M+H)$^+$.

EXAMPLE 18

3-[6-(Azetidine-1-carbonyl)pyridin-3-yl]oxy-5-[(3R)-1-cyclopropyl-2-oxo-pyrrolidin-3-yl]oxy-N-(5-methylpyrazin-2-yl)benzamide

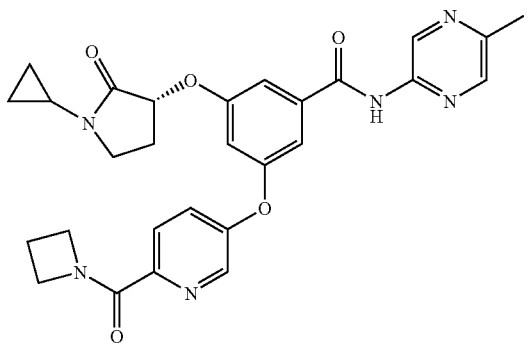

To a solution of ethyl 2-[3-[6-(azetidine-1-carbonyl)pyridin-3-yl]oxy-5-[(5-methylpyrazin-2-yl)carbamoyl]phenoxy]-4-methylsulfonyloxy-butanoate (Intermediate 27) (250 mg, 0.41 mmol) in acetonitrile (5 mL), was added NaI (62 mg, 0.41 mmol) and cyclopropylamine (56 μL, 0.81 mmol). The resulting mixture was heated in a microwave at 120° C. for 60 minutes. The solvent was evaporated under reduced pressure and the residue purified by flash chromatography eluting with 0-40% methanol in DCM to afford the racemic product (91 mg, 42%). 3-[6-(Azetidine-1-carbonyl)pyridin-3-yl]oxy-5-[(3R)-1-cyclopropyl-2-oxo-pyrrolidin-3-yl]oxy-N-(5-methylpyrazin-2-yl)benzamide was separated from its enantiomer by chiral HPLC using a Merck 50 mm 20 μm Chiralcel OJ column eluting with methanol at a flow rate of 60 mL/min. 91 mg of racemic material was separated in 1 injection of 5 mL at 18 mg/ml in methanol to afford the product which eluted before its enantiomer (27 mg, 12%). $^1$H NMR δ (300 MHz, CDCl$_3$) 0.66-0.91 (m, 4H), 2.14 (sextet, 1H), 2.35 (quintet, 2H), 2.48-2.62 (m, 4H), 2.66-2.78 (m, 1H), 3.27-3.49 (m, 2H), 4.25 (t, 2H), 4.70 (t, 2H), 4.92 (t, 1H), 6.96 (s, 1H), 7.22 (s, 1H), 7.38 (d, 1H), 7.45 (s, 1H), 8.11 (d, 1H), 8.13 (s, 1H), 8.33 (s, 1H), 8.57 (s, 1H), 9.51 (s, 1H); m/z 529 (M+H)$^+$.

EXAMPLE 19

3-[6-(Azetidine-1-carbonyl)pyridin-3-yl]oxy-5-[(3S)-1-cyclopropyl-2-oxo-pyrrolidin-3-yl]oxy-N-(5-methylpyrazin-2-yl)benzamide

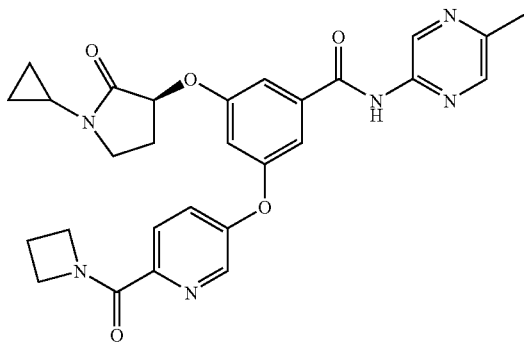

To a solution of ethyl 2-[3-[6-(azetidine-1-carbonyl)pyridin-3-yl]oxy-5-[(5-methylpyrazin-2-yl)carbamoyl]phenoxy]-4-methylsulfonyloxy-butanoate (Intermediate 27) (250 mg, 0.41 mmol) in acetonitrile (5 mL), was added NaI (62 mg, 0.41 mmol) and cyclopropylamine (56 µL, 0.81 mmol). The resulting mixture was heated in a microwave at 120° C. for 60 minutes. The solvent was evaporated under reduced pressure and the residue purified by flash chromatography eluting with 0-40% methanol in DCM to afford the racemic product (91 mg, 42%). 3-[6-(Azetidine-1-carbonyl)pyridin-3-yl]oxy-5-[(3S)-1-cyclopropyl-2-oxo-pyrrolidin-3-yl]oxy-N-(5-methylpyrazin-2-yl)benzamide was separated from its enantiomer by chiral HPLC using a Merck 50 mm 20 µm Chiralcel OJ column eluting with methanol at a flow rate of 60 mL/min. 91 mg of racemic material was separated in 1 injection of 5 mL at 18 mg/ml in methanol to afford the product which eluted after its enantiomer (29 mg, 13%). $^1$H NMR δ (300 MHz, CDCl$_3$) 0.66-0.91 (m, 4H), 2.14 (sextet, 1H), 2.35 (quintet, 2H), 2.48-2.62 (m, 4H), 2.66-2.78 (m, 1H), 3.27-3.49 (m, 2H), 4.25 (t, 2H), 4.70 (t, 2H), 4.92 (t, 1H), 6.96 (s, 1H), 7.22 (s, 1H), 7.38 (d, 1H), 7.45 (s, 1H), 8.11 (d, 1H), 8.13 (s, 1H), 8.33 (s, 1H), 8.57 (s, 1H), 9.51 (s, 1H); m/z 529 (M+H)$^+$.

EXAMPLE 20

3-[6-(Azetidine-1-carbonyl)pyridin-3-yl]oxy-5-[(3R)-1-cyclobutyl-2-oxo-pyrrolidin-3-yl]oxy-N-(5-methylpyrazin-2-yl)benzamide

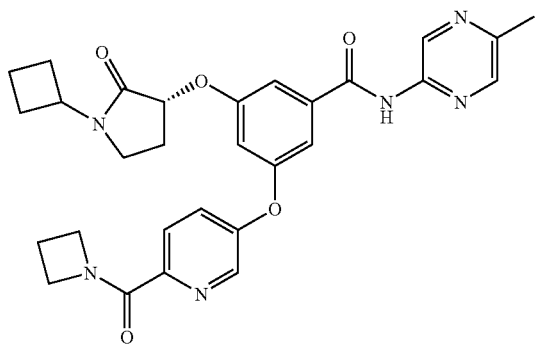

From racemic 3-[6-(azetidine-1-carbonyl)pyridin-3-yl]oxy-5-(1-cyclobutyl-2-oxo-pyrrolidin-3-yl)oxy-N-(5-methylpyrazin-2-yl)benzamide (Example 17), 3-[6-(azetidine-1-carbonyl)pyridin-3-yl]oxy-5-[(3R)-1-cyclobutyl-2-oxo-pyrrolidin-3-yl]oxy-N-(5-methylpyrazin-2-yl)benzamide was separated from its enantiomer by chiral HPLC using a Merck 50 mm 20 µm Chiralcel OJ column eluting with methanol at a flow rate of 60 mL/min. 97 mg of racemic material was separated in 1 injection of 5 mL at 20 mg/ml in methanol to afford the product which eluted before its enantiomer to afford the product (50 mg, 47%). $^1$H NMR δ (300 MHz, CDCl$_3$) 1.69-1.78 (2H, m), 2.13-2.23 (5H, m), 2.30-2.40 (2H, m), 2.55-2.64 (4H, m), 3.39-3.47 (1H, m), 3.57-3.64 (1H, m), 4.24 (2H t), 4.62-4.72 (3H, m), 4.91-4.96 (1H, m), 6.96 (1H, t), 7.22 (1H t), 7.36-7.40 (1H, m), 7.45 (1H, t), 8.09-8.13 (2H, m), 8.32 (1H, d), 8.61 (1H, s), 9.51 (1H, d); m/z 543 (M+H)$^+$.

EXAMPLE 21

3-[6-(Azetidine-1-carbonyl)pyridin-3-yl]oxy-5-[(3S)-1-cyclobutyl-2-oxo-pyrrolidin-3-yl]oxy-N-(5-methylpyrazin-2-yl)benzamide

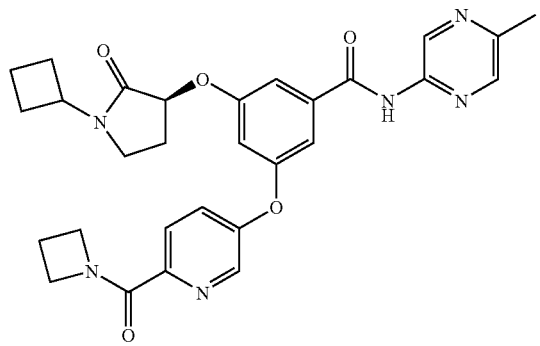

From racemic 3-[6-(azetidine-1-carbonyl)pyridin-3-yl]oxy-5-(1-cyclobutyl-2-oxo-pyrrolidin-3-yl)oxy-N-(5-methylpyrazin-2-yl)benzamide (Example 17), 3-[6-(azetidine-1-carbonyl)pyridin-3-yl]oxy-5-[(3S)-1-cyclobutyl-2-oxo-pyrrolidin-3-yl]oxy-N-(5-methylpyrazin-2-yl)benzamide was separated from its enantiomer by chiral HPLC using a Merck 50 mm 20 µm Chiralcel OJ column eluting with methanol at a flow rate of 60 mL/min. 97 mg of racemic material was separated in 1 injection of 5 mL at 20 mg/ml in methanol to afford the product which eluted after its enantiomer to afford the product (47 mg, 44%). $^1$H NMR δ (300 MHz, CDCl$_3$) 1.69-1.78 (2H, m), 2.13-2.23 (5H, m), 2.30-2.40 (2H, m), 2.55-2.64 (4H, m), 3.39-3.47 (1H, m), 3.57-3.64 (1H, m), 4.24 (2H t), 4.62-4.72 (3H, m), 4.91-4.96 (1H, m), 6.96 (1H, t), 7.22 (1H t), 7.36-7.40 (1H, m), 7.45 (1H, t), 8.09-8.13 (2H, m), 8.32 (1H, d), 8.61 (1H, s), 9.51 (1H, d); m/z 543 (M+H)$^+$.

EXAMPLE 22

-[6-(Azetidine-1-carbonyl)pyridin-3-yl]oxy-5-[(3R)-1-ethyl-2-oxo-pyrrolidin-3-yl]oxy-N-(5-methylpyrazin-2-yl)benzamide

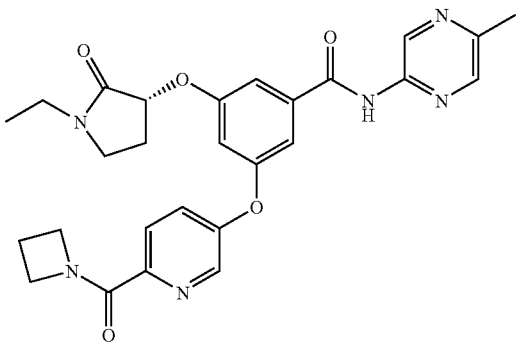

From racemic 3-[6-(Azetidine-1-carbonyl)pyridin-3-yl]oxy-5-(1-ethyl-2-oxo-pyrrolidin-3-yl)oxy-N-(5-methylpyrazin-2-yl)benzamide (197 mg, 0.38 mmol) (Example 10), 3-[6-(azetidine-1-carbonyl)pyridin-3-yl]oxy-5-[(3R)-1-ethyl-2-oxo-pyrrolidin-3-yl]oxy-N-(5-methylpyrazin-2-yl) benzamide was separated from its enantiomer by chiral HPLC using a Merck 50 mm 20 μm Chiralcel OJ column eluting with methanol at a flow rate of 60 mL/min. 197 mg of racemic material was separated in 1 injection of 5 mL at 40 mg/ml in methanol to afford the product which eluted before its enantiomer to afford the product (55 mg, 28%). ¹H NMR δ (300 MHz, CDCl₃) 1.18 (t, 3H), 2.13-2.26 (m, 1H), 2.36 (quintet, 2H), 2.52-2.69 (m, 4H), 3.36-3.58 (m, 4H), 4.25 (t, 2H), 4.71 (t, 2H), 4.95 (t, 1H), 6.98 (s, 1H), 7.22 (s, 1H), 7.39 (d, 1H), 7.47 (s, 1H), 8.12 (d, 1H), 8.14 (s, 1H), 8.33 (s, 1H), 8.56 (s, 1H), 9.53 (s, 1H); m/z 517 (M+H)⁺.

EXAMPLE 23

3-[6-(Azetidine-1-carbonyl)pyridin-3-yl]oxy-5-[(3S)-1-ethyl-2-oxo-pyrrolidin-3-yl]oxy-N-(5-methylpyrazin-2-yl)benzamide

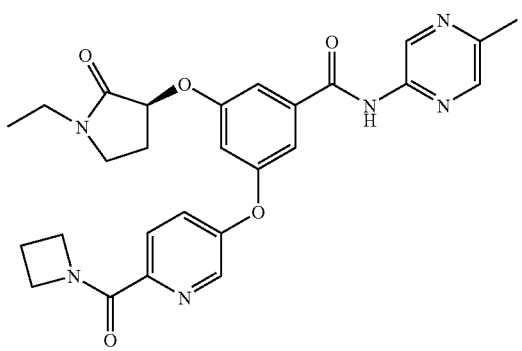

From racemic 3-[6-(azetidine-1-carbonyl)pyridin-3-yl]oxy-5-(1-ethyl-2-oxo-pyrrolidin-3-yl)oxy-N-(5-methylpyrazin-2-yl)benzamide (197 mg, 0.38 mmol) (Example 10), 3-[6-(azetidine-1-carbonyl)pyridin-3-yl]oxy-5-[(3R)-1-ethyl-2-oxo-pyrrolidin-3-yl]oxy-N-(5-methylpyrazin-2-yl) benzamide was separated from its enantiomer by chiral HPLC using a Merck 50 mm 20 μm Chiralcel OJ column eluting with methanol at a flow rate of 60 mL/min. 197 mg of racemic material was separated in 1 injection of 5 mL at 40 mg/ml in methanol to afford the product which eluted after its enantiomer to afford the product (51 mg, 26%). ¹H NMR δ (300 MHz, CDCl₃) 1.18 (t, 3H), 2.13-2.26 (m, 1H), 2.36 (quintet, 2H), 2.52-2.69 (m, 4H), 3.36-3.58 (m, 4H), 4.25 (t, 2H), 4.71 (t, 2H), 4.95 (t, 1H), 6.98 (s, 1H), 7.22 (s, 1H), 7.39 (d, 1H), 7.47 (s, 1H), 8.12 (d, 1H), 8.14 (s, 1H), 8.33 (s, 1H), 8.56 (s, 1H), 9.53 (s, 1H); m/z 517 (M+H)⁺.

EXAMPLE 24

N,N-Dimethyl-5-[3-[(3S)-1-methyl-2-oxo-pyrrolidin-3-yl]oxy-5-[(5-methylpyrazin-2-yl)carbamoyl]phenoxy]pyrazine-2-carboxamide

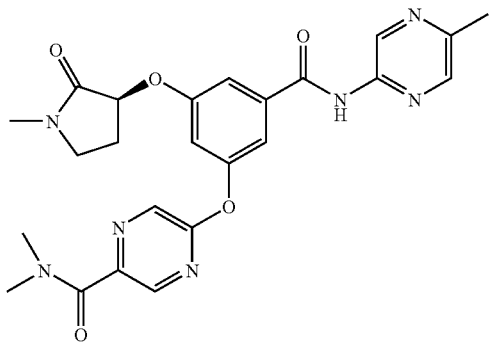

A mixture of 3-hydroxy-5-[(3S)-1-methyl-2-oxo-pyrrolidin-3-yl]oxy-N-(5-methylpyrazin-2-yl)benzamide (Intermediate 18) (188 mg, 0.55 mmol), 5-(azetidin-1-ylcarbonyl)-2-chloropyrazine (CAS no. 915949-00-7) (712 mg, 3.6 mmol) and potassium carbonate (152 mg, 0.55 mmol) in acetonitrile (5 mL) was stirred at 120° C. for 2 hours. The solution was evaporated to dryness then diluted with ethyl acetate (30 mL), washed with water (2×10 mL) and brine (20 mL), dried (MgSO₄), filtered and the solvent removed under reduced pressure. The residue was purified by flash chromatography on silica eluting with 50-100% ethyl acetate in isohexane to afford the product (210 mg, 78%). ¹H NMR δ (300 MHz, CDCL₃) 2.15-2.31 (m, 1H), 2.52-2.68 (m, 1H), 2.56 (s, 3H), 2.95 (s, 3H), 3.17 (d, 6H), 3.35-3.59 (m, 2H), 4.95 (t, 1H), 7.15 (s, 1H), 7.37 (s, 1H), 7.56 (s, 1H), 8.14 (s, 1H), 8.39 (s, 1H), 8.52 (s, 2H), 9.54 (s, 1H); m/z 492 (M+H)⁺.

EXAMPLE 25

3-[(2,2-Dioxo-6-oxa-2-λ⁶-thiabicyclo[5.4.0]undeca-7,9,11-trien-9-yl)oxy]-5-[(3S)-1-methyl-2-oxo-pyrrolidin-3-yl]oxy-N-(1H-pyrazol-3-yl)benzamide

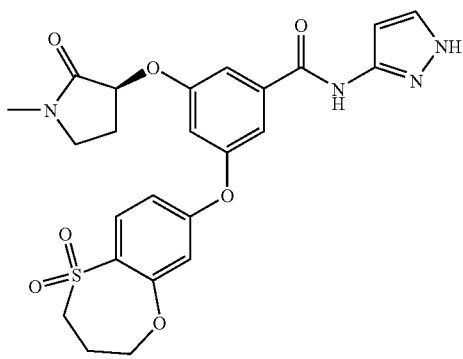

The tert-butyl 3-[[3-[(2,2-dioxo-6-oxa-2-X⁶-thiabicyclo[5.4.0]undeca-7,9,11-trien-9-yl)oxy]-5-[(3S)-1-methyl-2- oxo-pyrrolidin-3-yl]oxy-benzoyl]amino]pyrazole-1-carboxylate (412 mg, 0.67 mmol) (Intermediate 40) was dissolved in acetonitrile (5 mL) and heated in the microwave for 12 minutes at 150° C. The solvent was removed under reduced pressure to afford the product (348 mg, 100%). $^1$H NMR δ (300 MHz, CDCl$_3$) 2.10-2.24 (m, 1H), 2.35-2.45 (m, 2H), 2.48-2.66 (m, 1H), 2.92 (s, 3H), 3.29-3.53 (m, 4H), 4.22 (t, 2H), 4.89 (t, 1H), 6.71 (s, 1H), 6.77 (s, 1H), 6.80-6.86 (m, 2H), 7.19 (s, 1H), 7.44 (s, 1H), 7.47 (s, 1H), 7.89 (d, 1H), 10.24 (s, 1H); m/z 513 (M+H$^+$)

EXAMPLE 26

3-[2-Chloro-4-(dimethylcarbamoyl)phenoxy]-5-[(3S)-1-methyl-2-oxo-pyrrolidin-3-yl]oxy-N-(5-methylpyrazin-2-yl)benzamide

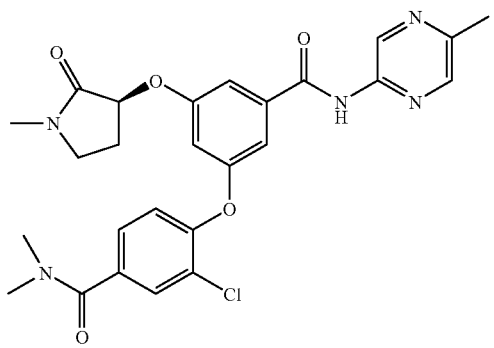

A mixture of 3-hydroxy-5-[(3S)-1-methyl-2-oxo-pyrrolidin-3-yl]oxy-N-(5-methylpyrazin-2-yl)benzamide (Intermediate 18) (206 mg, 0.6 mmol), 3-chloro-4-fluoro-N,N-dimethyl-benzamide (CAS no. 871657-07-7) (192 mg, 0.9 mmol) and potassium carbonate (166 mg, 1.2 mmol) in N,N-dimethylacetamide (5 mL) was stirred at 160° C. for 6 hours. The solution was evaporated under reduced pressure, the residue dissolved in ethyl acetate (40 mL), washed with water (2×20 mL) and brine (10 mL), dried (MgSO$_4$), filtered and the solvent removed under reduced pressure. The residue was purified by flash chromatography on silica eluting with 0-4% methanol in DCM to afford the product (98 mg, 31%). $^1$H NMR δ (300 MHz, CDCl$_3$) 2.10-2.27 (m, 1H), 2.54-2.67 (m, 1H), 2.55 (s, 3H), 2.93 (s, 3H), 2.98-3.19 (m, 6H), 3.34-3.57 (m, 2H), 4.92 (t, 1H), 6.86 (s, 1H), 7.06 (d, 1H), 7.16 (s, 1H), 7.33 (d, 1H), 7.40 (s, 1H), 7.57 (s, 1H), 8.13 (s, 1H), 8.53 (s, 1H), 9.51 (s, 1H); m/z 524 (M+H$^+$).

EXAMPLE 27

3-[(6,6-dioxo-2-oxa-6-λ$^6$-thia-5-azabicyclo[5.4.0]undeca-8,10,12-trien-10-yl)oxy]-5-[(3S)-1-methyl-2-oxo-pyrrolidin-3-yl]oxy-N-(5-methylpyrazin-2-yl)benzamide

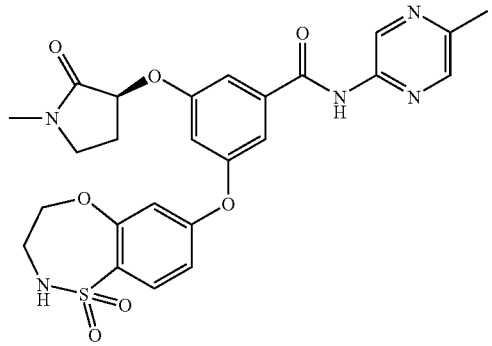

A mixture of 3-hydroxy-5-[(3S)-1-methyl-2-oxo-pyrrolidin-3-yl]oxy-N-(5-methylpyrazin-2-yl)benzamide (Intermediate 18) (206 mg, 0.6 mmol), 2,4-difluoro-N-(2-hydroxyethyl)benzenesulfonamide (CAS no. 915771-62-9) (213 mg, 0.9 mmol) and potassium carbonate (166 mg, 1.2 mmol) in N,N-dimethylacetamide (5 mL) was stirred at 160° C. for 6 hrs. The solution was evaporated under reduced pressure. The residue dissolved in ethyl acetate (32 mL) and DCM (8 mL), washed with water (2×20 mL), brine (10 mL), dried (MgSO$_4$) and the solvent removed under reduced pressure. The residue was purified by flash chromatography on silica eluting with 0-4% methanol in DCM to give afford the product (19 mg, 6%). $^1$H NMR δ (300 MHz, CDCl$_3$) 2.12-2.26 (m, 1H), 2.54-2.68 (m, 1H), 2.55 (s, 3H), 2.93 (s, 3H), 3.35-3.57 (m, 3H), 3.61-3.70 (m, 2H), 4.23 (t, 2H), 4.94 (t, 1H), 5.04 (t, 1H), 6.74 (s, 1H), 6.79 (d, 1H), 6.95 (s, 1H), 7.22 (s, 1H), 7.46 (s, 1H), 7.77 (d, 1H), 8.72 (s, 1H), 9.48 (s, 1H); m/z 540 (M+H$^+$).

EXAMPLE 28

3-[(3S)-1-methyl-2-oxo-pyrrolidin-3-yl]oxy-N-(5-methylpyrazin-2-yl)-5-(6-methylsulfonylpyridin-3-yl)oxy-benzamide

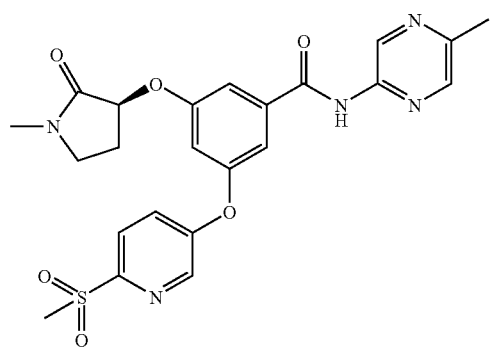

A mixture 3-hydroxy-5-[(3S)-1-methyl-2-oxo-pyrrolidin-3-yl]oxy-N-(5-methylpyrazin-2-yl)benzamide (Intermediate 18) (305 mg, 0.6 mmol), 5-bromo-2-methylsulfonyl-pyridine (CAS no. 98626-95-0) (142 mg, 0.6 mmol), cesium carbonate (390 mg, 1.2 mmol) and tris(triphenylphosphine)copper bromide (CAS no. 15709-74-7) (112 mg, 0.12 mmol) in N,N-dimethylacetamide (5 mL) was stirred in the microwave at 160° C. for 6 hours. N,N-Dimethylacetamide was removed by evaporation under reduced pressure. The residue was partitioned between ethyl acetate (30 mL) and water (50 mL). The organic phase was separated and the aqueous layer was acidified with hydrochloric acid (1N, 5 mL) and extracted with ethyl acetate (2×50 mL). The combined organic extracts were washed with brine, dried (MgSO$_4$) and concentrated under reduced pressure. The residue was purified by flash chromatography on silica eluting with 0-5% methanol in DCM to afford the product (120 mg, 40%). $^1$H NMR δ (300 MHz, CDCl$_3$) 2.14-2.32 (m, 1H), 2.52-2.69 (m, 1H), 2.55 (s, 3H), 2.94 (s, 3H), 3.23 (s, 3H), 3.35-3.59 (m, 2H), 4.96 (t, 1H), 7.05 (s, 1H), 7.27 (s, 1H), 7.48 (d, 1H), 7.54 (s, 1H), 8.07 (d, 1H), 8.14 (s, 1H), 8.49 (s, 1H), 8.55 (s, 1H), 9.51 (s, 1H); m/z 498 (M+H+).

EXAMPLE 29

N,N-dimethyl-5-[3-[(3S)-1-methyl-2-oxo-pyrrolidin-3-yl]oxy-5-[(5-methylpyrazin-2-yl)carbamoyl]phenoxy]pyridine-2-carboxamide

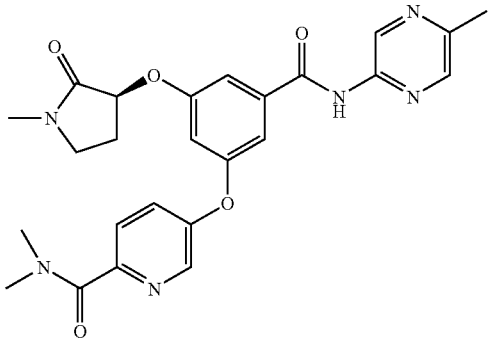

A mixture of 3-hydroxy-5-[(3S)-1-methyl-2-oxo-pyrrolidin-3-yl]oxy-N-(5-methylpyrazin-2-yl)benzamide (Intermediate 18) (206 mg, 0.6 mmol), 5-bromo-N,N-dimethyl-pyridine-2-carboxamide (CAS no. 845305-86-4) (165 mg, 0.72 mmol), cesium carbonate (587 mg, 1.8 mmol) and tris(triphenylphosphine)copper bromide (CAS no. 15709-74-7) (112 mg, 0.12 mmol) in N,N-dimethylacetamide (5 mL) was stirred at 160° C. for 6 hours. The N,N-dimethylacetamide was evaporated under reduced pressure and the residue was dissolved in water (20 mL) extracted with ethyl acetate (3×20 mL). The combined organic extracts were dried (MgSO4) and evaporated. The residue was purified by flash chromatography on silica eluting with 0-5% methanol in DCM. The resulting compound was dissolved in ethyl acetate (110 mL), washed with citric acid (1N, 10 mL), water (10 mL) and brine (10 mL), dried (MgSO4) and the solvent evaporated to afford the product (67 mg, 23%). 1H NMR δ (300 MHz, CDCl3) 2.14-2.26 (m, 1H), 2.52-2.67 (m, 1H), 2.55 (s, 3H), 2.94 (s, 3H), 3.15 (s, 6H), 3.34-3.57 (m, 2H), 4.94 (t, 1H), 6.97 (s, 1H), 7.23 (s, 1H), 7.40 (d, 1H), 7.46 (s, 1H), 7.72 (s, 1H), 8.14 (s, 1H), 8.38 (s, 1H), 8.58 (s, 1H), 9.52 (s, 1H); m/z 491 (M+H+).

EXAMPLE 30

3-[(9-methyl-10-oxo-7-oxa-9-azabicyclo[4.4.0]deca-2,4,11-trien-4-yl)oxy]-5-[(3S)-1-methyl-2-oxo-pyrrolidin-3-yl]oxy-N-(1H-pyrazol-3-yl)benzamide

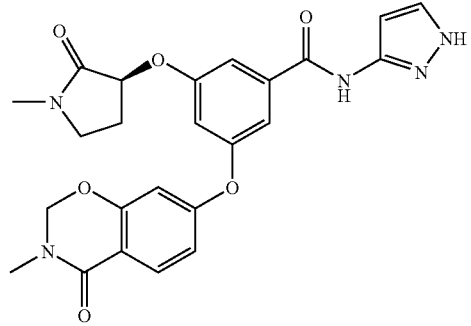

1-Chloro-N,N,2-trimethyl-prop-1-en-1-amine (0.88 mL, 0.66 mmol) was added to a solution of 3-[(9-methyl-10-oxo-7-oxa-9-azabicyclo[4.4.0]deca-2,4,11-trien-4-yl)oxy]-5-[(3S)-1-methyl-2-oxo-pyrrolidin-3-yl]oxy-benzoic acid (Intermediate 43) (209 mg, 0.66 mmol) in DCM (10 mL) and stirred at ambient temperature for 30 minutes. tert-Butyl3-aminopyrazole-1-carboxylate (CAS no. 863504-94-1) (187 mg, 1.02 mmol) and pyridine (0.084 mL, 1.0 mmol) were added and the reaction stirred overnight. The solvent was removed under reduced pressure. The residue was dissolved in ethyl acetate (30 mL), washed with water (2×10 mL), saturated sodium bicarbonate solution (10 mL) and brine (10 mL), dried (MgSO4) and evaporated under reduced pressure. The residue was purified by flash chromatography on silica, eluting with a gradient of 0 to 100% ethyl acetate in isohexane, followed by 5% methanol in DCM. The residue was dissolved in acetonitrile (5 mL) and heated in a microwave for 12 min at 150° C. The resulting mixture was evaporated to dryness and the residue purified by flash chromatography on silica, eluting with 0-5% methanol in DCM to afford the product (50 mg, 16%). 1H NMR δ (300 MHz, CDCl3) 2.05-2.21 (m, 1H), 2.44-2.63 (m, 1H), 2.68-2.85 (m, 1H), 2.89 (s, 3H), 3.08 (s, 3H), 3.31-3.51 (m, 2H), 4.82-4.96 (m, 1H), 5.15 (s, 2H), 6.51 (s, 1H), 6.70 (d, 1H), 6.78 (s, 1H), 6.81 (s, 1H), 7.22 (s, 1H), 7.41 (s, 1H), 7.43 (s, 1H), 7.90 (d, 1H), 10.29 (s, 1H); m/z 478 (M+H+).

EXAMPLE 31

N,N-dimethyl-5-[3-[(3S)-1-methyl-2-oxo-pyrrolidin-3-yl]oxy-5-[(3-methyl-1,2,4-thiadiazol-5-yl)carbamoyl]phenoxy]pyrazine-2-carboxamide

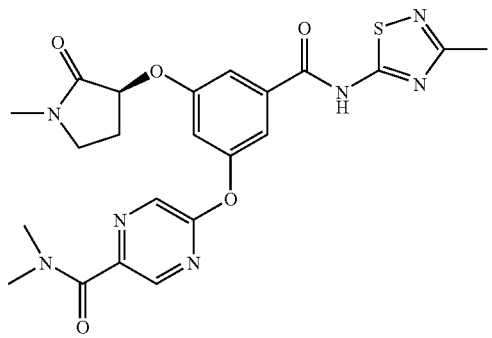

1-Chloro-N,N,2-trimethyl-prop-1-en-1-amine (0.142 mL, 1.07 mmol) was added to a solution of 3-[5-(dimethylcarbamoyl)pyrazin-2-yl]oxy-5-[(3S)-1-methyl-2-oxo-pyrrolidin-3-yl]oxy-benzoic acid (Intermediate 45) (358 mg, 0.9 mmol) in DCM (7 mL) and stirred at ambient temperature for 30 minutes. 3-Methyl-1,2,4-thiadiazol-5-amine (CAS no. 17467-35-5) (206 mg, 1.8 mmol) and pyridine (0.147 mL, 1.8 mmol) were added and the reaction stirred for 20 hours. The solvent was removed under reduced pressure. The residue was dissolved in ethyl acetate (15 mL) and DCM (15 mL), washed with water (10 mL) and filtered to give a solid which was washed with water and dried. The filtrate was washed with citric acid (1N, 10 mL), water (10 mL), saturated sodium bicarbonate solution (10 mL), brine (10 mL), dried (MgSO4) and evaporated. The residue was combined with the solid isolated from the filtration and purified by flash chromatography on silica eluting with a gradient of 0-3% methanol in DCM to afford the product (322 mg, 72%). 1H NMR δ (300

MHz, CDCl₃) 1.93-2.06 (m, 1H), 2.45 (s, 3H), 2.55-2.66 (m, 1H), 2.80 (s, 3H), 3.03 (s, 6H), 3.19-3.53 (m, 2H), 5.14 (t, 1H), 7.30 (s, 1H), 7.63 (s, 1H), 7.72 (s, 1H), 8.43 (s, 1H), 8.58 (s, 1H), 11.9-12.8 (br s, 1H); m/z 498 (M+H⁺).

EXAMPLE 32

N,N-Dimethyl-5-[3-[(3S)-1-methyl-2-oxo-pyrrolidin-3-yl]oxy-5-[(4-methyl-1,3-thiazol-2-yl)carbamoyl]phenoxy]pyrazine-2-carboxamide

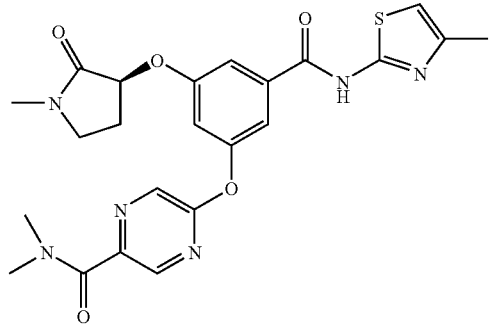

1-Chloro-N,N,2-trimethyl-prop-1-en-1-amine (0.14 mL, 1.1 mmol) was added to a solution of 3-[5-(dimethylcarbamoyl)pyrazin-2-yl]oxy-5-[(3S)-1-methyl-2-oxo-pyrrolidin-3-yl]oxy-benzoic acid (Intermediate 45) (358 mg, 0.9 mmol) in DCM (7 mL) and stirred at ambient temperature for 30 minutes. 4-Methyl-1,3-thiazol-2-amine (CAS no. 1603-91-4) (206 mg, 1.8 mmol) and pyridine (0.15 mL, 1.8 mmol) were added and the reaction stirred for 20 hours. The solvent was removed under reduced pressure. The residue was dissolved in ethyl acetate (30 mL), washed with water (2×10 mL) and brine (10 mL), dried (MgSO₄) and evaporated. The residue was purified by flash chromatography on silica eluting with a gradient of 0 to 5% methanol in DCM to afford the product (200 mg, 45%). ¹H NMR δ (300 MHz, CDCl₃) 2.09-2.22 (m, 1H), 2.25 (s, 3H), 2.50-2.65 (m, 1H), 2.93 (s, 3H), 3.18 (d, 6H), 3.34-3.55 (m, 2H), 4.86 (t, 1H), 6.56 (s, 1H), 7.16 (s, 1H), 7.37 (s, 1H), 7.54 (s, 1H), 8.37 (s, 1H), 8.51 (s, 1H), 10.0-11.0 (br s, 1H); m/z 497 (M+H⁺).

Intermediate 1

3-[6-(Azetidine-1-carbonyl)pyridin-3-yl]oxy-5-hydroxy-N-(5-methylpyrazin-2-yl)benzamide

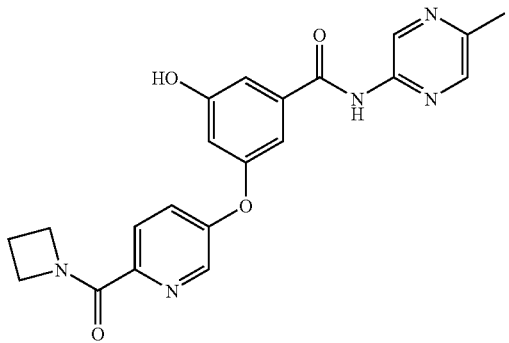

3-[6-(Azetidine-1-carbonyl)pyridin-3-yl]oxy-N-(5-methylpyrazin-2-yl)-5-phenylmethoxy-benzamide (Intermediate 2) (3.9 g, 7.9 mmol) was dissolved in ethyl acetate (200 mL) and ethanol (200 mL). 10% Palladium on carbon (390 mg, cat.) was added and the mixture stirred under an atmosphere of hydrogen for 16 hours. Methanol (150 mL) was added and the suspension was filtered. The filtrate was evaporated under reduced pressure. The residue was washed firstly with methanol (150 mL), ethyl acetate (150 mL) and DMA (10 mL) and secondly with DMF (50 mL). The combined filtrates were evaporated under reduced pressure to afford the product (3.17 g, 99%). ¹H NMR δ (400 MHz, DMSO) 11.02 (s, 1H), 10.35 (s, 1H), 9.26 (s, 1H), 8.47 (s, 1H), 8.40 (s, 1H), 8.05 (d, 1H), 7.62 (d, 1H), 7.34 (s, 1H), 7.31 (s, 1H), 6.81 (s, 1H), 4.64 (t, 2H), 4.13 (t, 2H), 2.53 (s, 3H), 2.33 (quintet, 2H); m/z 406 (M+H)⁺.

Intermediate 2

3-[6-(azetidine-1-carbonyl)pyridin-3-yl]oxy-N-(5-methylpyrazin-2-yl)-5-phenylmethoxy-benzamide

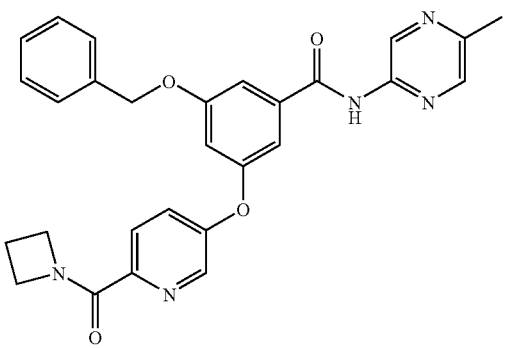

1-Chloro-N,N,2-trimethyl-prop-1-en-1-amine (2.4 mL, 18 mmol) was added to a solution of 3-[6-(azetidine-1-carbonyl)pyridin-3-yl]oxy-5-phenylmethoxy-benzoic acid (Intermediate 3) (6.19 g, 15 mmol) in DCM (100 mL) and stirred at ambient temperature for 30 minutes. Further 1-chloro-N,N,2-trimethyl-prop-1-en-1-amine (0.24 mL, 1.8 mmol) was added and stirring continued for 20 minutes. 5-Methylpyrazin-2-amine (CAS no. 5521-58-4) (3.34 g, 31 mmol) and pyridine (2.5 mL, 31 mmol) were added and the reaction stirred for a further 16 hours. The solvent was removed under reduced pressure. The residue was dissolved in ethyl acetate (350 mL), washed with water (2×100 mL) and brine (100 mL), dried (MgSO₄), and evaporated under reduced pressure. The residue was purified by flash chromatography, eluting with a gradient of 50-75% ethyl acetate in isohexane, to afford the product (4.01 g, 53%). ¹H NMR δ (400 MHz, CDCl₃) 2.28 (quintet, 2H), 2.49 (s, 3H), 4.18 (t, 2H), 4.63 (t, 2H), 5.05 (s, 2H), 6.78 (s, 1H), 7.10 (s, 1H), 7.25-7.37 (m, 7H), 8.04 (d, 1H), 8.07 (s, 1H), 8.25 (s, 2H), 9.46 (s, 1H); m/z 496 (M+H)+.

Intermediate 3

3-[6-(Azetidine-1-carbonyl)pyridin-3-yl]oxy-5-phenylmethoxy-benzoic acid

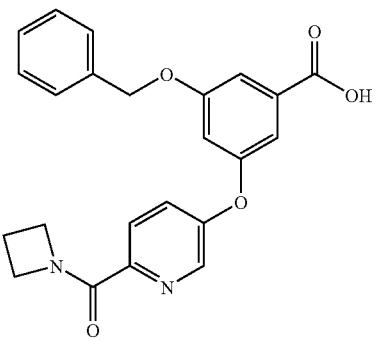

A mixture of methyl 3-hydroxy-5-phenylmethoxy-benzoate (CAS no. 54915-31-0) (5.16 g, 20 mmol), azetidin-1-yl-(5-bromopyridin-2-yl)methanone (CAS no. 845306-16-3, Intermediate 34) (5.3 g, 22 mmol), caesium carbonate (19.6 g, 60 mmol) and tris(triphenylphosphine)copper bromide (CAS no. 15709-74-7) (3.73 g, 4 mmol) in DMA (100 mL) was stirred at 160° C. for 6 hours. The DMA was evaporated under reduced pressure and the residue was dissolved in water (200 mL), washed with ethyl acetate (3×50 mL), acidified with 2N hydrochloric acid and extracted with ethyl acetate (3×100 mL). The organic layer washed with water (2×20 mL) and brine (20 mL), dried (MgSO$_4$) and the solvent removed under reduced pressure to afford the product (6.18 g, 76%). $^1$H NMR δ (400 MHz, CDCl$_3$) 2.29 (s, 2H), 4.20 (s, 2H), 4.64 (s, 2H), 5.04 (s, 2H), 6.83 (s, 1H), 7.22-7.44 (m, 7H), 7.49 (s, 1H), 7.79-8.63 (m, 2H); m/z 405 (M+H)+.

Intermediate 4

3-Bromo-1-methyl-pyrrolidin-2-one

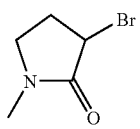

Sodium hydride (60%, 1.2 g, mmol) was added portionwise to a solution of 2,4-dibromo-N-methyl-butanamide (7.8 g, 30 mmol) (Intermediate 5, CAS no. 33693-57-1) in THF (25 mL) under argon at 10-15° C. The mixture was added slowly to an ice-water mixture and extracted with DCM. The organic layer was separated and the aqueous layer re-extracted with DCM (2×10 mL). The combined organic layers were washed with brine (20 mL), dried (MgSO$_4$) and evaporated to give a brown oil which was triturated with hexane and purified by column chromatography on silica eluting with 0-20% ethylacetate in DCM to afford the product (4.3 g, 81%). $^1$H NMR δ (400 MHz, CDCl$_3$) 2.22-2.30 (m, 1H), 2.54 (sextet, 1H), 2.84 (s, 3H), 3.22-3.29 (dt, 1H), 3.46-3.54 (dt, 1H), 4.34 (d, 1H); m/z 178 (M+H)+

Intermediate 5

2,4-dibromo-N-methyl-butanamide

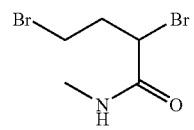

2,4-Dibromobutanoyl chloride (CAS no. 82820-87-9) (16.9 g, 64 mmol) in DCM (20 mL) was added dropwise to a solution of methylamine (20 mL) in water (30 mL) and DCM (30 mL) at 10-15° C., then warmed to 30° C. and stirred for 30 minutes. The organic layer was separated and the aqueous layer re-extracted with DCM (2×10 mL), the combined organic layers were washed with brine (20 mL), dried (MgSO$_4$) and evaporated to afford the product (16.3 g, 98%). $^1$H NMR δ (400 MHz, CDCl$_3$) 2.35-2.45 (m, 1H), 2.57-2.67 (m, 1H), 2.81 (d, 3H), 3.44-3.54 (m, 2H), 4.46 (q, 1H), 6.34 (s, 1H).

Intermediate 6

3-[5-(azetidine-1-carbonyl)pyrazin-2-yl]oxy-5-[(3S)-1-methyl-2-oxo-pyrrolidin-3-yl]oxy-benzoic acid

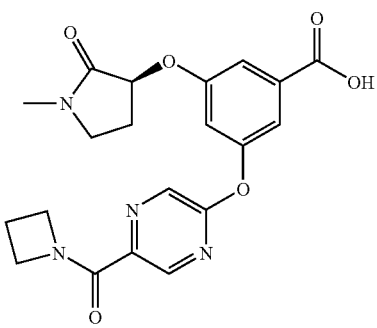

Methyl 3-[5-(azetidine-1-carbonyl)pyrazin-2-yl]oxy-5-[(3S)-1-methyl-2-oxo-pyrrolidin-3-yl]oxy-benzoate (Intermediate 7) (304 mg, 0.71 mmol) was dissolved in THF (6 mL) and methanol (2 mL); 1 N lithium hydroxide solution (0.85 mL) was added followed by water (8 mL), and the resultant solution was stirred for 1 hr at room temperature. The majority of the organic solvent was removed by distillation, the remaining aqueous solution was filtered and acidified with 2N hydrochloric acid and extracted with 1:1 ethyl acetate: DCM (2×40 mL). The combined organic extracts were washed with water (10 mL) and brine (20 mL) and dried (MgSO$_4$) to afford the product (265 mg, 96%). $^1$H NMR δ (300 MHz, CDCl$_3$) 2.12-2.27 (m, 1H), 2.38 (quintet, 2H), 2.52-2.67 (m, 1H), 2.95 (s, 3H), 3.36-3.57 (m, 2H), 4.27 (t, 2H), 4.68 (t, 2H), 4.97 (t, 1H), 7.10 (s, 1H), 7.45 (s, 1H), 7.62 (s, 1H), 8.31 (s, 1H), 8.84 (s, 1H); m/z 413 (M+H)+

Intermediate 7

Methyl 3-[5-(azetidine-1-carbonyl)pyrazin-2-yl]oxy-5-[(3S)-1-methyl-2-oxo-pyrrolidin-3-yl]oxy-benzoate

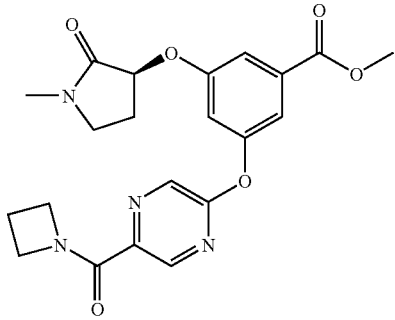

A mixture of methyl 3-hydroxy-5-[(3S)-1-methyl-2-oxo-pyrrolidin-3-yl]oxy-benzoate (Intermediate 8) (265 mg, 1.0 mmol), azetidin-1-yl-(5-chloropyrazin-2-yl)methanone (Intermediate 32) (198 mg, 1.0 mmol) and polymer supported-carbonate (690 mg, 2.0 mmol) in DMA (5 mL) was stirred at 100° C. for 1 hr. The mixture was filtered and the DMA was removed under reduced pressure. The residue was dissolved in ethyl acetate (50 mL), washed with saturated sodium bicarbonate (10 mL), water (20 mL) and brine (20 mL), dried (MgSO$_4$), filtered and the solvent removed under reduced pressure. The residue was purified by chromatography on silica eluting with 20-100% ethyl acetate in isohexane then 10% Methanol in DCM to give afford the product (304 mg, 71%). $^1$H NMR δ (300 MHz, CDCl$_3$) 2.13-2.27 (m, 1H), 2.31-2.44 (m, 2H), 2.53-2.66 (m, 1H), 2.94 (s, 3H), 3.35-3.58 (m, 2H), 3.90 (s, 3H), 4.26 (t, 2H), 4.68 (t, 2H), 4.93 (t, 1H), 7.14 (s, 1H), 7.46 (s, 1H), 7.60 (s, 1H), 8.31 (s, 1H), 8.84 (s, 1H); m/z 427 (M+H)+

Intermediate 8

Methyl 3-hydroxy-5-[(3S)-1-methyl-2-oxo-pyrrolidin-3-yl]oxy-benzoate

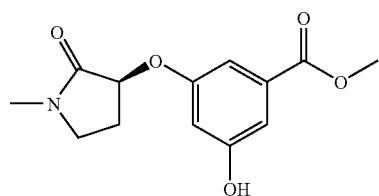

A solution of methyl 3-[(3S)-1-methyl-2-oxo-pyrrolidin-3-yl]oxy-5-phenylmethoxy-benzoate (Intermediate 9) (1.42 g, 4.0 mmol) was added to a suspension of 10% palladium on carbon (140 mg, catalytic) in THF (40 mL) and methanol (40 mL). The mixture was stirred under an atmosphere of hydrogen for 16 hours. The mixture was filtered and the filtrate evaporated under reduced pressure to give the product (1.06 g, 100%). $^1$H NMR δ (300 MHz, CDCl$_3$) 2.06-2.20 (m, 1H), 2.56-2.68 (m, 1H), 2.97 (s, 3H), 3.37-3.55 (m, 2H), 3.86 (s, 3H), 4.93 (t, 1H), 6.81 (s, 1H), 7.04 (s, 1H), 7.12 (s, 1H), 7.66 (s, 1H); m/z 266 (M+H)+

Intermediate 9

Methyl 3-[(3S)-1-methyl-2-oxo-pyrrolidin-3-yl]oxy-5-phenylmethoxy-benzoate

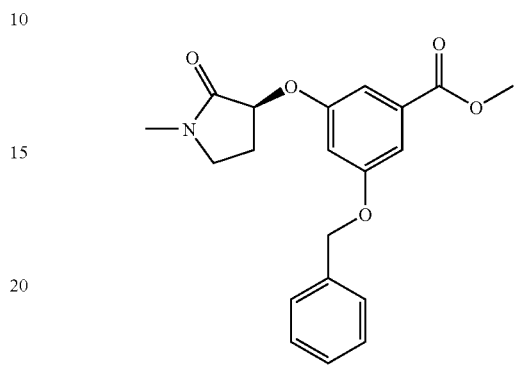

Methyl 3-hydroxy-5-phenylmethoxy-benzoate (CAS no. 54915-31-0) (10.3 g, 40 mmol) and 3-bromo-1-methyl-pyrrolidin-2-one (Intermediate 4) (8.54 g, 48 mmol) were dissolved in DMF, treated with potassium carbonate (12.1 g, 88 mmol) and stirred at room temperature for 16 hours and then at 50° C. for 3 hours. The DMF was evaporated under reduced pressure and the residue partitioned between ethyl acetate (100 mL) and water (30 mL). The organic layer was separated, washed with brine (30 mL), dried (MgSO$_4$) and evaporated under reduced pressure. The residue was purified by flash chromatography on silica eluting with 0-100% ethyl acetate in hexane to give the racemic product (8.7 g). The desired product was separated from its enantiomer by chiral HPLC using Merck 50 mm 20 μm Chiralpak AS—No ASV00SC JG001 and ASV000SC BD004 columns in series, eluting with 30% ethylacetate in isohexane at a flow rate of 60 mL/min, using 9 separate injections of 70 mL of a 14 mg/ml solution of the racemate in ethanol (32 mL) and isohexane (38 mL) to afford the product (3.6 g, 41%) which eluted before its enantiomer. $^1$H NMR δ (300 MHz, CDCl$_3$) 2.06-2.20 (m, 1H), 2.51-2.63 (m, 1H), 2.94 (s, 3H), 3.31-3.54 (m, 2H), 3.89 (s, 3H), 4.87 (t, 1H), 5.08 (s, 2H), 6.90 (t, 1H), 7.27-7.46 (m, 7H).

Intermediate 10

3-[5-(Azetidine-1-carbonyl)pyrazin-2-yl]oxy-5-[(3R)-1-methyl-2-oxo-ppyrrolidin-3-yl]oxy-benzoic acid

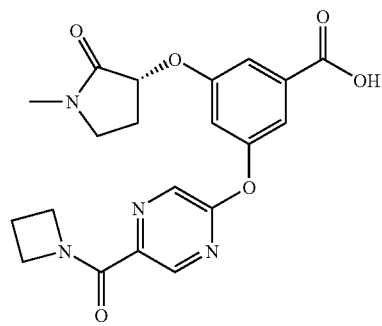

Methyl 3-[5-(azetidine-1-carbonyl)pyrazin-2-yl]oxy-5-[(3R)-1-methyl-2-oxo-pyrrolidin-3-yl]oxy-benzoate (Intermediate 11) (292 mg, 0.68 mmol) was dissolved in THF (6 mL) and methanol (2 mL) and 1 N Lithium hydroxide (0.85 mL) was added, followed by water (8 mL). The resultant solution was stirred for 1 hr at room temperature. The majority of the organic solvent was removed by distillation, the remaining aqueous solution was filtered and acidified with 2N hydrochloric acid and extracted with 1:1 ethyl acetate: DCM (2×40 mL), the organics were washed with water (10 mL) and brine (20 mL) and dried (MgSO$_4$) to afford the product (280 mg, 100%). $^1$H NMR δ (300 MHz, CDCl$_3$) 2.12-2.27 (m, 1H), 2.38 (quintet, 2H), 2.52-2.67 (m, 1H), 2.95 (s, 3H), 3.36-3.57 (m, 2H), 4.27 (t, 2H), 4.68 (t, 2H), 4.97 (t, 1H), 7.10 (s, 1H), 7.45 (s, 1H), 7.62 (s, 1H), 8.31 (s, 1H), 8.84 (s, 1H); m/z 413 (M+H)$^+$ Intermediate 11

Methyl 3-[5-(azetidine-1-carbonyl)pyrazin-2-yl]oxy-5-[(3R)-1-methyl-2-oxo-pyrrolidin-3-yl]oxy-benzoate

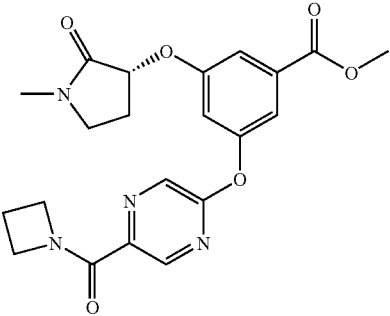

A mixture of methyl 3-hydroxy-5-[(3R)-1-methyl-2-oxo-pyrrolidin-3-yl]oxy-benzoate (Intermediate 12) (265 mg, 1 mmol), azetidin-1-yl-(5-chloropyrazin-2-yl)methanone (Intermediate 32) (298 mg, 1.5 mmol) and polymer supported-carbonate (860 mg, 2.5 mmol) in DMA (5 mL) was stirred at 100° C. for 2 hours. The mixture was filtered and the DMA was removed under reduced pressure. The residue was purified by flash chromatography on silica eluting with 20-100% ethyl acetate in isohexane then 10% methanol in DCM to afford the product (292 mg, 68%). $^1$H NMR δ (300 MHz, CDCl$_3$) 2.13-2.27 (m, 1H), 2.31-2.44 (m, 2H), 2.53-2.66 (m, 1H), 2.94 (s, 3H), 3.35-3.58 (m, 2H), 3.90 (s, 3H), 4.26 (t, 2H), 4.68 (t, 2H), 4.93 (t, 1H), 7.14 (s, 1H), 7.46 (s, 1H), 7.60 (s, 1H), 8.31 (s, 1H), 8.84 (s, 1H); m/z 427 (M+H)$^+$ Intermediate 12

Methyl 3-hydroxy-5-[(3R)-1-methyl-2-oxo-pyrrolidin-3-yl]oxy-benzoate

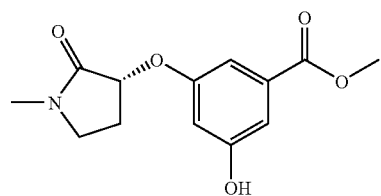

A solution of methyl 3-[(3R)-1-methyl-2-oxo-pyrrolidin-3-yl]oxy-5-phenylmethoxy-benzoate (Intermediate 13) (1.42 g, 4.0 mmol) was added to a suspension of 10% palladium on carbon (140 mg, catalytic) in THF (40 mL) and methanol (40 mL). The mixture was stirred under an atmosphere of hydrogen for 16 hours. The mixture was filtered and the filtrate evaporated under reduced pressure to give the product (1.04 g, 98%). $^1$H NMR δ (300 MHz, CDCl$_3$) 2.06-2.20 (m, 1H), 2.56-2.68 (m, 1H), 2.97 (s, 3H), 3.37-3.55 (m, 2H), 3.86 (s, 3H), 4.93 (t, 1H), 6.81 (s, 1H), 7.04 (s, 1H), 7.12 (s, 1H), 7.66 (s, 1H); m/z 266 (M+H)$^+$ Intermediate 13

Methyl 3-[(3R)-1-methyl-2-oxo-pyrrolidin-3-yl]oxy-5-phenylmethoxy-benzoate

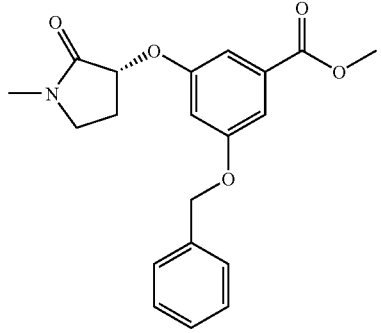

Methyl 3-hydroxy-5-phenylmethoxy-benzoate (CAS no. 54915-31-0) (10.3 g, 40 mmol) and 3-bromo-1-methyl-pyrrolidin-2-one (Intermediate 4) (8.54 g, 48 mmol) were dissolved in DMF and treated with potassium carbonate (12.1 g, 88 mmol) and stirred at room temperature for 16 hours and then at 50° C. for 3 hours. The DMF was evaporated under reduced pressure and the residue partitioned between ethyl acetate (100 mL) and water (30 mL). The organic layer was separated, washed with brine (30 mL), dried (MgSO$_4$) and evaporated under reduced pressure. The residue was purified by flash chromatography on silica eluting with 0-100% ethyl acetate in hexane to give the racemic product (8.7 g). The desired product was separated from its enantiomer by chiral HPLC using Merck 50 mm 20 µm Chiralpak AS—No ASV00SC JG001 and ASV000SC BD004 columns in series, eluting with 30% ethylacetate in isohexane at a flow rate of 60 mL/min, using 9 separate injections of 70 mL of a 14 mg/ml solution of the racemate in Ethanol (32 mL) and isohexane (38 mL) to afford the product (3.6 g, 41%) which eluted after its enantiomer. $^1$H NMR δ (300 MHz, CDCl$_3$) 2.06-2.20 (m, 1H), 2.51-2.63 (m, 1H), 2.94 (s, 3H), 3.31-3.54 (m, 2H), 3.89 (s, 3H), 4.87 (t, 1H), 5.08 (s, 2H), 6.90 (t, 1H), 7.27-7.46 (m, 7H).

Intermediate 14 tert-Butyl 3-[[3-[4-(azetidine-1-carbonyl)phenoxy]-5-[(3S)-1-methyl-2-oxo-pyrrolidin-3-yl]oxy-benzoyl]amino]pyrazole-1-carboxylate

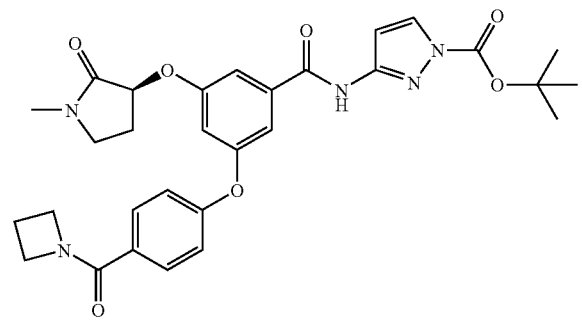

1-Chloro-N,N,2-trimethyl-prop-1-en-1-amine (0.12 mL, 0.87 mmol) was added to a solution of 3-[4-(azetidine-1-carbonyl)phenoxy]-5-[(3S)-1-methyl-2-oxo-pyrrolidin-3-yl]oxy-benzoic acid (Intermediate 15) (298 mg, 0.73 mmol) in DCM (5 mL) and stirred at ambient temperature for 30 minutes. tert-Butyl 3-aminopyrazole-1-carboxylate (CAS no. 863504-94-1) (268 mg, 1.46 mmol) and pyridine (0.119 mL, 1.46 mmol) were added and the reaction stirred for 16 hours. The solvent was removed under reduced pressure. The residue was dissolved in ethyl acetate (30 mL), washed with water (2×10 ml) and brine (10 mL), dried (MgSO$_4$), filtered and evaporated under reduced pressure. The residue was purified by flash chromatography on silica, eluting with a gradient of 0-100% ethyl acetate in isohexane, followed by 5% methanol in DCM to afford the product (388 mg, 93%). m/z 574 (M–H)$^-$ Intermediate 15

3-[4-(Azetidine-1-carbonyl)phenoxy]-5-[(3S)-1-methyl-2-oxo-pyrrolidin-3-yl]oxy-benzoic acid

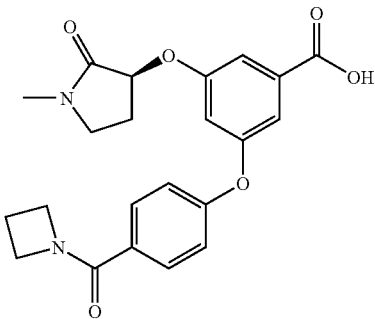

Methyl 3-[4-(azetidine-1-carbonyl)phenoxy]-5-[(3S)-1-methyl-2-oxo-pyrrolidin-3-yl]oxy-benzoate (Intermediate 16) (309 mg, 0.73 mmol) was dissolved in THF (6 mL) and methanol (2 mL) and 1N lithium hydroxide (0.88 mL) was added followed by water (8 mL). The resultant solution was stirred for 1 hr at room temperature. The majority of the organic solvent was removed by distillation under reduced pressure. The remaining aqueous solution was filtered and acidified with 2N hydrochloric acid and extracted with ethyl acetate (2×40 mL), the combined organics were washed with water (10 mL) and brine (20 mL) and dried (MgSO$_4$) to afford the product (298 mg, 100%). m/z 411 (M+H)$^+$ Intermediate 16

Methyl 3-[4-(azetidine-1-carbonyl)phenoxy]-5-[(3S)-1-methyl-2-oxo-pyrrolidin-3-yl]oxy-benzoate

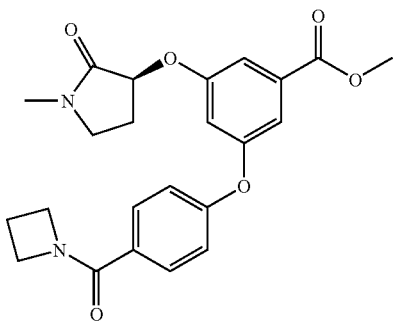

Methyl 3-[4-(azetidine-1-carbonyl)-2-chloro-phenoxy]-5-[(3S)-1-methyl-2-oxo-pyrrolidin-3-yl]oxy-benzoate (Intermediate 17) (372 mg, 0.81 mmol) was added to a suspension of 10% palladium on carbon (37 mg, catalytic) in THF (10 mL) and ethanol (10 mL) and the resulting mixture was stirred under an atmosphere of hydrogen for 16 hours. The suspension was filtered and the filtrate evaporated under reduced pressure. The residue was dissolved in ethyl acetate (30 mL), washed with water (10 mL) and brine (10 mL), dried (MgSO$_4$) and evaporated under reduced pressure to afford the product (309 mg, 90%). $^1$HNMR δ (300 MHz, CDCl$_3$) 2.10-2.23 (m, 1H), 2.36 (quintet, 2H), 2.52-2.65 (m, 1H), 2.94 (s, 3H), 3.32-3.54 (m, 2H), 3.89 (s, 3H), 4.18-4.39 (m, 4H), 4.90 (t, 1H), 6.94 (s, 1H), 7.01 (d, 2H), 7.32 (s, 1H), 7.48 (s, 1H), 7.64 (d, 2H); m/z 425 (M+H)$^+$ Intermediate 17

Methyl 3-[4-(azetidine-1-carbonyl)-2-chloro-phenoxy]-5-[(3S)-1-methyl-2-oxo-pyrrolidin-3-yl]oxy-benzoate

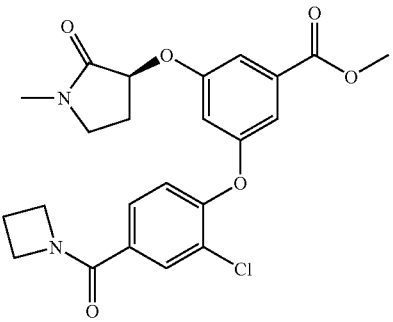

A mixture of methyl 3-hydroxy-5-[(3S)-1-methyl-2-oxo-pyrrolidin-3-yl]oxy-benzoate (Intermediate 8) (265 mg, 1 mmol), azetidin-1-yl-(3-chloro-4-fluoro-phenyl)methanone (CAS no. 863454-79-9) (320 mg, 1.5 mmol) and potassium carbonate (276 mg, 2.0 mmol) in DMA (10 mL) was stirred at 120° C. for 16 hours. The solution was evaporated under reduced pressure. The residue was dissolved in ethyl acetate (50 mL), washed with water (3×20 mL), dried (MgSO$_4$), filtered and the solvent removed under reduced pressure. The combined aqueous extracts were acidified with 2N hydrochloric acid, extracted with a mixture of ethyl acetate and DCM (1:1, 3×20 mL), washed with brine, dried (MgSO$_4$), filtered and the solvent removed under reduced pressure. The residue from this was dissolved in THF (2 mL) and methanol (1 mL) and treated with 2M (trimethylsilyl)diazomethane (0.240 mL, 0.48 mmol) and stirred for 30 minutes. The solution was treated with acetic acid (1 drop), evaporated under reduced pressure. This residue was combined with that from the initial ethyl acetate extraction and purified by flash chromatography on silica eluting with 20-100% ethyl acetate in isohexane to afford the product (380 mg, 83%). m/z 459 (M+H)+

Intermediate 18

3-Hydroxy-5-[(3S)-1-methyl-2-oxo-pyrrolidin-3-yl]oxy-N-(5-methylpyrazin-2-yl)benzamide

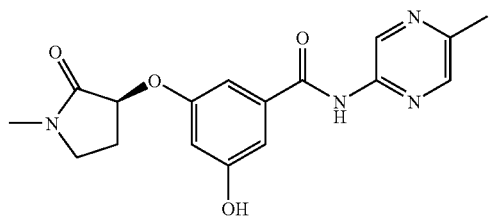

A solution of 3-[(3S)-1-methyl-2-oxo-pyrrolidin-3-yl]oxy-N-(5-methylpyrazin-2-yl)-5-phenylmethoxy-benzamide (Intermediate 19) (449 mg, 1.04 mmol) in THF (10 mL) and methanol (10 mL) containing 10% palladium on carbon (catalytic) was stirred under an atmosphere of hydrogen for 16 hours. The palladium on carbon was removed by filtration and the filtrate evaporated under reduced pressure to afford product (390 mg, 100%). $^1$HNMR δ (300 MHz, CDCl$_3$) 2.07-2.22 (m, 1H), 2.54 (s, 3H), 2.57-2.70 (m, 1H), 2.97 (s, 3H), 3.38-3.58 (m, 3H), 4.99 (t, 1H), 6.71 (s, 1H), 6.87 (s, 1H), 6.97 (s, 1H), 8.15 (s, 1H), 8.66 (s, 1H), 9.49 (s, 1H); m/z 343 (M+H)+.

Intermediate 19

3-[(3S)-1-Methyl-2-oxo-pyrrolidin-3-yl]oxy-N-(5-methylpyrazin-2-yl)-5-phenylmethoxy-benzamide

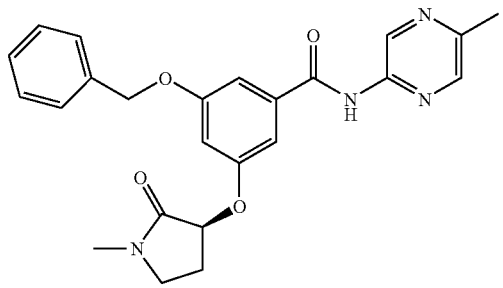

1-Chloro-N,N,2-trimethyl-prop-1-en-1-amine (0.979 mL, 7.4 mmol) was added to a solution of 3-[(3S)-1-methyl-2-oxo-pyrrolidin-3-yl]oxy-5-phenylmethoxy-benzoic acid (Intermediate 20) (2.1 g, 6.2 mmol) in DCM (50 mL) and stirred at ambient temperature for 50 minutes. 5-Methylpyrazin-2-amine (CAS no. 5521-58-4) (1.35 g, 12.4 mmol) and pyridine (1.0 mL, 12 mmol) were added and the reaction stirred for a further 3 hours. The solvent was evaporated under reduced pressure and the residue taken up in ethyl acetate (50 mL), washed with water (2×10 mL), brine (10 mL), dried (MgSO$_4$) and filtered. Evaporation under reduced pressure gave crude product which was purified by flash chromatography on silica, eluting with a gradient of 0-100% ethyl acetate in isohexane. This crystallised to afford the product (449 mg, 17%). To the filtrate was added saturated sodium bicarbonate (20 mL) and the mixture extracted with 2:1 ethyl acetate: DCM (3×45 mL), the organics were washed with brine (10 mL), dried (MgSO$_4$), filtered and evaporated under reduced pressure to give further product (937 mg, 35%). $^1$H NMR δ (300 MHz, CDCl$_3$) 2.09-2.24 (m, 1H), 2.53-2.66 (m, 4H), 2.94 (s, 3H), 3.33-3.57 (m, 2H), 4.89 (t, 1H), 5.10 (s, 2H), 6.91 (s, 1H), 7.15-7.20 (m, 2H), 7.30-7.48 (m, 5H), 8.13 (s, 1H), 8.40 (s, 1H), 9.54 (s, 1H); m/z 433 (M+H)+.

Intermediate 20

3-[(3S)-1-Methyl-2-oxo-pyrrolidin-3-yl]oxy-5-phenylmethoxy-benzoic acid

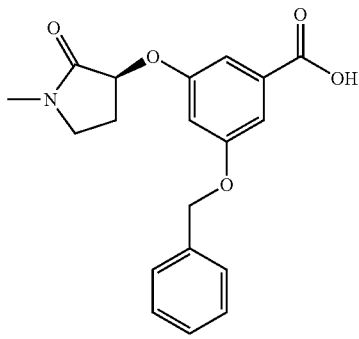

Methyl 3-[(3S)-1-methyl-2-oxo-pyrrolidin-3-yl]oxy-5-phenylmethoxy-benzoate (Intermediate 9) (2.4 g, 6.8 mmol) was dissolved in THF (45 mL), methanol (15 mL) and 1 N lithiumhydroxide (8.1 mL). Water (60 mL) was added dropwise until the solution went cloudy and the resultant solution was stirred for 3 hours at room temperature. The organics were removed by evaporation under reduced pressure, the aqueous solution was filtered, acidified with 2N hydrochloric acid, extracted with ethyl acetate (3×20 mL), washed with water (10 mL), brine (10 mL) and evaporated to dryness under reduced pressure to give product (2.106 g, 92%). $^1$H NMR δ (300 MHz, CDCl$_3$) 2.07-2.21 (m, 1H), 2.51-2.65 (m, 1H), 2.96 (s, 3H), 3.32-3.55 (m, 2H), 4.92 (t, 1H), 5.06 (s, 2H), 6.88 (s, 1H), 7.28-7.46 (m, 7H); m/z 340 (M–H)−.

Intermediate 21

Azetidin-1-yl-(5,6-dichloropyridin-3-yl)methanone

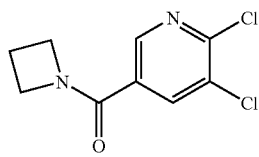

5,6-Dichloropyridine-3-carboxylic acid (CAS no. 41667-95-2) (32 g, 0.17 mol) was suspended in DCM (500 mL) and 1M HCl in ether (0.17 L, 0.17 mol) added. Oxalyl chloride (17 mL, 0.20 mol) and then DMF (2 drops) were added and stirred at room temperature for 16 hours. The reaction mixture was concentrated under reduced pressure, azeotroped with toluene and re-dissolved into DCM (250 mL). Azetidine hydrochloride (17.5 g, 0.18 mol) was added, followed by triethylamine (51 mL, 0.37 mol) and the reaction stirred at room temperature for 2 hours. The reaction mixture was concentrated under reduced pressure then water (500 mL) and ethyl acetate (500 mL) were added. The organic layer was separated and the aqueous phase was re-extracted with ethyl acetate (5×150 mL). The combined organics were washed with citric acid (250 mL), saturated sodium bicarbonate solution (250 mL), brine (250 mL), dried (MgSO₄), filtered and evaporated under reduced pressure to give a solid which was recrystallised in ethyl acetate and dried under reduced pressure to give the product (18.2 g, 47%). ¹H NMR δ (400 MHz, CDCl₃) 2.34 (quintet, 2H), 4.20 (s, 2H), 4.27 (s, 2H), 8.02 (d, 1H), 8.44 (d, 1H); m/z 231 (M+H)⁺.

Intermediate 22

3-[4-(Azetidine-1-carbonyl)-2-chloro-phenoxy]-5-[(3S)-1-methyl-2-oxo-pyrrolidin-3-yl]oxy-N-(5-methylpyrazin-2-yl)benzamide

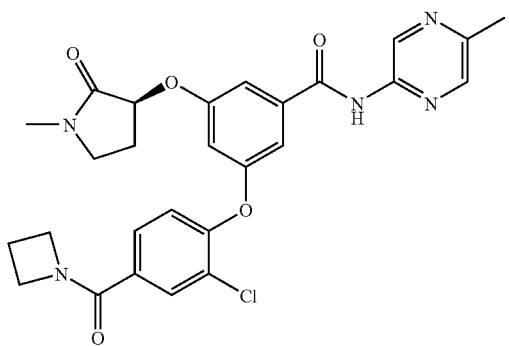

A mixture of 3-hydroxy-5-[(3S)-1-methyl-2-oxo-pyrrolidin-3-yl]oxy-N-(5-methylpyrazin-2-yl)benzamide (Intermediate 18) (136 mg, 0.4 mmol), azetidin-1-yl-(3-chloro-4-fluoro-phenyl)methanone (CAS no. 863454-79-9) (128 mg, 0.6 mmol) and potassium carbonate (111 mg, 0.8 mmol) in DMA (5 mL) was stirred at 120° C. for 16 hours. The solution was evaporated under reduced pressure, then the residue was dissolved in ethyl acetate (40 mL), washed with water (2×20 mL) and brine (10 mL), then dried (MgSO₄), filtered and the solvent removed under reduced pressure. The residue was purified by chromatography on silica eluting with 0-4% methanol/DCM to afford the product (120 mg, 56%). m/z 536 (M+H)⁺.

Intermediate 23

9-Fluoro-6-oxa-2λ⁶-thiabicyclo[5.4.0]undeca-8,10,12-triene 2,2-dioxide

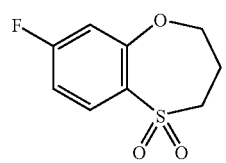

m-Chloroperbenzoic acid (77%, 17.0 g, 69 mmol) was added to a mixture of 9-fluoro-6-oxa-2-thiabicyclo[5.4.0]un-deca-8,10,12-triene (Intermediate 24) (5.1 g, 28 mmol)) and MgSO₄ (excess) in DCM and stirred at ambient temperature for 24 hours. Water (300 mL) was added and the mixture was extracted with dichloromethane (2×300 mL). The combined organic extracts were washed with 2N sodium hydroxide solution (200 mL) and brine (200 mL), dried (MgSO₄) and evaporated under reduced pressure. The residue was purified by flash chromatography, eluting with 0-80% ethyl acetate in isohexane to afford the product (5.3 g, 88%). ¹H NMR δ (400 MHz, CDCl₃): 2.41-2.46 (m, 2H), 3.34-3.37 (m, 2H), 4.26-4.29 (m, 2H), 6.88-6.91 (m, 1H), 6.95-7.00 (m, 1H), 7.96-8.00 (m, 1H).

Intermediate 24

9-Fluoro-6-oxa-2-thiabicyclo[5.4.0]undeca-8,10,12-triene

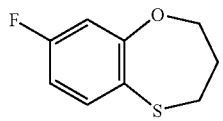

Sodium hydride (60%, 3.4, 85 mmol) was added to a solution of 3-(2,4-difluorophenyl)sulfanylpropan-1-ol (Intermediate 25) (7.9 g, 37 mmol) in THF (400 mL) and the mixture stirred at ambient temperature for 24 hours and the solvent removed under reduced pressure. Ice/water (200 mL) was added and extracted into ethyl acetate (2×500 mL), the combined organics were washed with brine (40 mL), dried (MgSO₄), filtered and the solvent removed under reduced pressure. The residue was purified by flash chromatography on silica, eluting with 0-10% ethyl acetate in isohexane to afford the product (5.1 g, 75%). ¹H NMR δ (400 MHZ, CDCl₃): 2.22-2.29 (m, 2H), 2.86-2.91 (m, 2H), 4.20-4.23 (m, 2H), 6.64-6.77 (m, 2H), 7.30-7.36 (m, 1H); m/z 185 (M+H)⁺.

Intermediate 25

3-(2,4-difluorophenyl)sulfanylpropan-1-ol

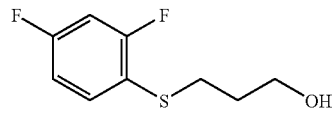

1M Hydrochloric acid (170 mL) was added to a solution of 2-[3-(2,4-difluorophenyl)sulfanylpropoxy]oxane (Intermediate 26) (10.8 g, 37 mmol) in methanol (170 mL) and stirred at ambient temperature for 40 minutes. The methanol was removed under reduced pressure and the remaining aqueous phase taken to pH 6. The solution was extracted with ethyl acetate (3×50 mL) and the combined organics washed with brine (50 mL), dried (MgSO₄) and the solvent removed under reduced pressure to afford the product (7.5 g, 99%). ¹H NMR δ (400 MHz, CDCl₃): 1.38 (t, 1H), 1.83 (quintet, 2H), 2.97 (t, 2H), 3.77 (q, 2H), 6.81-6.87 (m, 2H), 7.38-7.45 (m, 1H).

Intermediate 26

2-[3-(2,4-difluorophenyl)sulfanylpropoxy]oxane

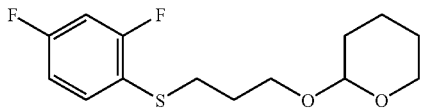

Sodium hydride (60%) (1.72 g, 44.8 mmol) was added to a solution of 2,4-difluorobenzenethiol (CAS no. 1996-44-7) (4.6 mL, 40 mmol) in THF (150 mL) at 0° C., under argon. The mixture was allowed to warm to room temperature and 2-(3-bromopropoxy)oxane (CAS no. 33821-94-2) (7.6 mL, 45 mmol) was added. The reaction was stirred at ambient temperature for 16 hours. The mixture was poured into ice/water (250 mL) and extracted with ethyl acetate (250 mL). The organic extract was washed with brine, dried (MgSO$_4$) and the solvent removed under reduced pressure. The residue was purified by flash chromatography, eluting with 0-10% ethyl acetate in isohexane afford the product (10.8 g, 84%). $^1$H NMR δ(400 MHZ, CDCl$_3$): 1.49-1.61 (m, 4H), 1.65-1.73 (m, 1H), 1.75-1.90 (m, 3H), 2.96 (t, 2H), 3.46-3.52 (m, 2H), 3.79-3.87 (m, 2H), 4.55-4.56 (m, 1H), 6.80-6.86 (m, 2H), 7.38-7.44 (m, 1H).

Intermediate 27

Ethyl 2-[3-[6-(azetidine-1-carbonyl)pyridin-3-yl]oxy-5-[(5-methylpyrazin-2-yl)carbamoyl]phenoxy]-4-methylsulfonyloxy-butanoate

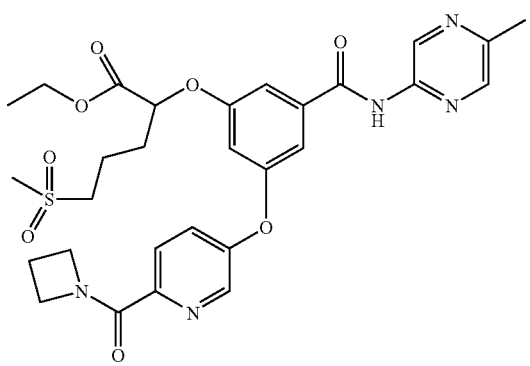

Methanesulfonyl chloride (13 L, 0.16 mmol) and triethylamine (34 μL, 0.24 mmol) were added to a solution of ethyl 2-[3-[6-(azetidine-1-carbonyl)pyridin-3-yl]oxy-5-[(5-methylpyrazin-2-yl)carbamoyl]phenoxy]-4-hydroxy-butanoate (Intermediate 28) (65 mg, 0.12 mmol) in DCM (5 mL) at 0° C. under nitrogen. The reaction was allowed to warm to RT and stirred for 2 hours. The solvent was evaporated under reduced pressure and the residue partitioned between ethyl acetate (10 mL) and brine (10 mL). The organic layer was separated and the aqueous layer re-extracted with ethyl acetate (10 mL). The combined organics were dried (MgSO$_4$), concentrated under reduced pressure and the residue purified by column chromatography on silica eluting with 0-10% methanol/DCM to give product (29 mg, 42%). $^1$H NMR δ (300 MHz, CDCl$_3$) 1.23-1.30 (3H, m), 2.33-2.46 (4H, m), 2.56 (3H, s), 3.03 (3H, s), 4.22-4.29 (4H, m), 4.44-4.49 (2H, m), 4.71 (2H t), 4.87-4.91 (1H, m), 6.81 (1H t), 7.21 (1H t), 7.29 (1H t), 7.38-7.41 (1H, m), 8.13 (2H d), 8.34 (1H d), 8.42 (1H, s), 9.51 (1H, s); m/z 615 (M+H)$^+$.

Intermediate 28

Ethyl 2-[3-[6-(azetidine-1-carbonyl)pyridin-3-yl]oxy-5-[(5-methylpyrazin-2-yl)carbamoyl]phenoxy]-4-hydroxy-butanoate

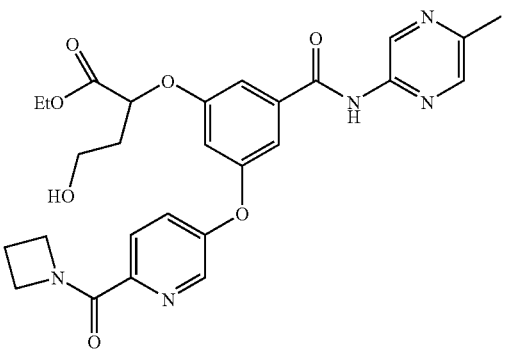

Potassium carbonate (113 mg, 0.82 mmol) was added to a solution of 3-[6-(azetidine-1-carbonyl)pyridin-3-yl]oxy-N-(5-methylpyrazin-2-yl)-5-(2-oxooxolan-3-yl)oxy-benzamide (Intermediate 29) (800 mg, 1.6 mmol) in ethanol (80 mL) at 0° C. under nitrogen. The reaction was allowed to warm to RT and stirred for 4 hours. The reaction mixture was filtered through silica, washing well with ethyl acetate, and concentrated to afford crude product which was used directly in the next stage without further purification.

Intermediate 29

3-[6-(Azetidine-1-carbonyl)pyridin-3-yl]oxy-N-(5-methylpyrazin-2-yl)-5-(2-oxooxolan-3-yl)oxy-benzamide

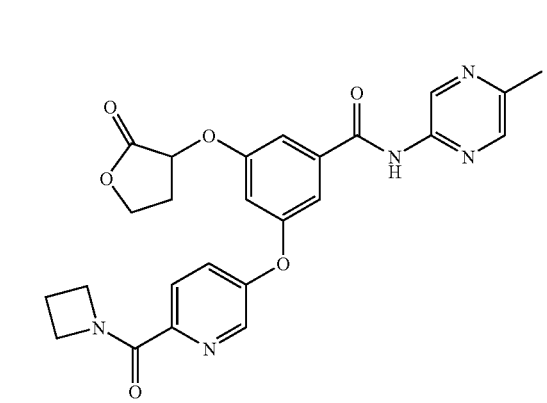

3-[6-(Azetidine-1-carbonyl)pyridin-3-yl]oxy-5-hydroxy-N-(5-methylpyrazin-2-yl)benzamide (Intermediate 1) (203 mg, 0.5 mmol), 3-hydroxyoxolan-2-one (CAS no. 19444-84-9) (0.078 mL, 1 mmol) and triphenyl phosphine (262 mg, 1 mmol) in anhydrous THF (10 mL) under argon at 0° C. was treated dropwise with DIAD (0.20 mL, 1 mmol). The mixture allowed to warm to room temperature and stirred for 16 hours.

The solvent was removed by evaporation under reduced pressure and the residue was purified by chromatography on silica eluting with 0-4% methanol:DCM to give product (212 mg 86%). ¹H NMR δ (400 MHz, CDCl₃) 2.29 (quintet, 2H), 2.40-2.48 (m, 1H), 2.50 (s, 3H), 2.69-2.78 (m, 1H), 4.18 (t, 2H), 4.33 (q, 1H), 4.49 (t, 1H), 4.64 (t, 2H), 4.99 (t, 1H), 6.89 (s, 1H), 7.18 (s, 1H), 7.33 (d, 1H), 7.36 (s, 1H), 8.06 (d, 1H), 8.08 (s, 1H), 8.28 (s, 1H), 8.41 (s, 1H), 9.46 (s, 1H); m/z 490 (M+H)⁺.

Intermediate 30

3-[6-(Azetidine-1-carbonyl)pyridin-3-yl]oxy-5-[(3S)-1-methyl-2-oxo-pyrrolidin-3-yl]oxy-benzoic acid

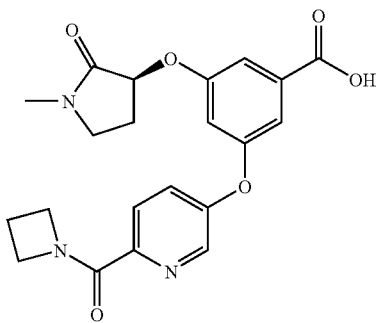

Methyl 3-[6-(azetidine-1-carbonyl)pyridin-3-yl]oxy-5-[(3S)-1-methyl-2-oxo-pyrrolidin-3-yl]oxy-benzoate (Intermediate 31) (439 mg, 1.0 mmol) was dissolved in THF (6 mL) and methanol, (2 mL) and 1 N lithium hydroxide (1.24 mL) was added. Water (8 mL) was then added dropwise and the resultant solution stirred for 1 hour at room temperature. The majority of the organic solvents were removed by distillation under reduced pressure. The aqueous residue was acidified with 2N hydrochloric acid and extracted with ethyl acetate (2×40 mL). The combined organic extracts were washed with water (10 mL) and brine (20 mL), dried (MgSO₄) and evaporated under reduced pressure to afford the product (406 mg, 96%). ¹H NMR δ (300 MHz, CDCl₃) 2.10-2.26 (m, 2H), 2.29-2.43 (m, 2H), 2.55-2.69 (m, 1H), 2.96 (s, 3H), 3.36-3.59 (m, 4H), 4.26 (t, 2H), 4.71 (t, 2H), 4.98 (t, 1H), 6.95 (s, 1H), 7.29 (s, 3H), 7.34 (d, 2H), 7.55 (s, 1H), 8.09 (d, 1H), 8.30 (s, 1H); m/z 411 (M+H)⁺.

Intermediate 31

Methyl 3-[6-(azetidine-1-carbonyl)pyridin-3-yl]oxy-5-[(3S)-1-methyl-2-oxo-pyrrolidin-3-yl]oxy-benzoate

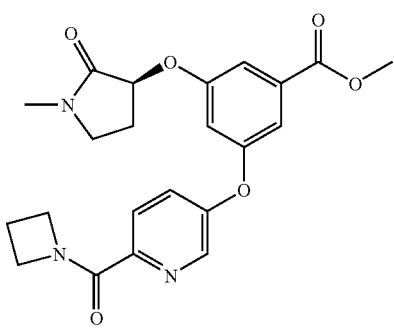

A mixture of methyl 3-hydroxy-5-[(3S)-1-methyl-2-oxo-pyrrolidin-3-yl]oxy-benzoate (Intermediate 8) (530 mg, 2 mmol), azetidin-1-yl-(5-bromopyridin-2-yl)methanone (CAS no. 845306-16-3) (531 mg, 2.2 mmol), caesium carbonate (1.956 g, 6 mmol) and tris(triphenylphosphine)copper bromide (CAS no. 15709-74-7) (373 mg, 0.4 mmol) in DMA (5 mL) was stirred at 160° C. for 6 hours. The DMA was evaporated under reduced pressure and the residue was dissolved in water (520 mL) washed with ethyl acetate (3×20 mL). The aqueous fraction was acidified with 2N hydrochloric acid and extracted with ethyl acetate (3×100 mL), the combined organic layers were washed with water (2×20 mL) and brine (20 mL), dried (MgSO₄) and the solvent removed under reduced pressure. The residue was dissolved in THF (6 mL) and methanol (3 mL) and was treated dropwise with 2M (trimethylsilyl)diazomethane in hexane (1.1 mL). The reaction was stirred for 30 min then treated with 1 drop of acetic acid, stirred for another 15 minutes and evaporated to dryness under reduced pressure. The residue was purified by chromatography eluting with 0-100% ethyl acetate/hexane to give afford the product (439 mg, 52%). ¹H NMR δ (300 MHz, CDCl₃) 2.10-2.24 (m, 1H), 2.35 (quintet, 2H), 2.52-2.67 (m, 1H), 2.93 (s, 3H), 3.34-3.56 (m, 2H), 3.89 (s, 3H), 4.25 (t, 2H), 4.70 (t, 2H), 4.91 (t, 1H), 6.99 (s, 1H), 7.32 (s, 1H), 7.35 (d, 1H), 7.53 (s, 1H), 8.10 (d, 1H), 8.31 (s, 1H); m/z 426 (M+H)⁺.

Intermediate 32

Azetidin-1-yl-(5-chloropyrazin-2-yl)methanone

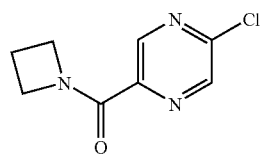

Oxalyl chloride (1.55 mL, 17.5 mmol), followed by DMF (2 drops), was added to a mixture of 5-chloropyrazine-2-carboxylic acid (CAS no. 36070-80-1, Intermediate 33) (2.31 g, 14.6 mmol) in DCM (40 mL). The reaction was stirred at RT for 2 hours after which time the volatiles were removed under reduced pressure. The residue was taken up DCM (40 mL) and azetidine (1.08 mL, 16.03 mmol) and triethylamine (4.46 mL, 32.06 mmol) added. The mixture was stirred at RT for 72 hours. The volatiles were removed under reduced pressure and ethyl acetate (100 mL) added to the residue. The organics were washed with water (100 mL), citric acid (50 mL), saturated sodium bicarbonate solution (50 mL) and brine (50 mL), dried (MgSO₄), filtered and the solvent removed under reduced pressure. The residue was purified by flash chromatography, eluting with a gradient of 50-100% ethyl acetate in isohexane, to afford the product (2.38 g, 82%). ¹HNMR δ (400 MHZ, CDCl₃): 2.35-2.42 (2H, m), 4.26 (2H, t), 4.67 (2H, t), 8.52 (1H, d), 9.09 (1H, d); m/z 198 (M+H)⁺.

Intermediate 33

5-Chloropyrazine-2-carboxylic acid

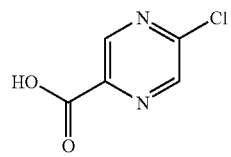

To a solution of methyl-5-chloropyrazine-2-carboxylate (120 mg, 0.70 mmol) in a mixture of acetonitrile (2 mL) and DMF (1 mL) was added lithium chloride (295 mg, 6.95 mmol). The suspension was heated to 160° C. for 5 minutes in a microwave after which time the reaction was diluted with water (10 mL). Saturated sodium bicarbonate solution (20 mL) was added and the aqueous layered extracted with ethyl acetate (2×30 mL). The organic extracts were discarded and the aqueous layer adjusted to pH 4 with 1N hydrochloric acid. The aqueous phase was extracted twice with ethyl acetate (20 mL) and the combined organics washed with water (2×20 mL) and brine (10 mL) and dried (MgSO₄). The volatiles were removed under reduced pressure to afford the product (68 mg). ¹H NMR δ (400 MHZ, CDCl₃): 7.20 (1H, br s), 8.72 (1H, s), 9.21-9.21 (1H, m); m/z 157 (M−H)⁺.

Intermediate 34

Azetidin-1-yl-(5-bromopyridin-2-yl)methanone

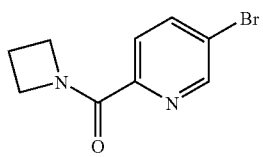

Oxalyl chloride (11.5 mL, 130 mmol) then DMF (2 drops) were added to a mixture of 5-bromopyridine-2-carboxylic acid (CAS no. 30766-11-1) (12.6 g, 62.4 mmol) in 4M HCl in dioxane (15.6 mL, 74.9 mmol) and DCM (300 mL). The mixture was stirred at ambient temperature for 18 hours. The volatiles were removed under reduced pressure and azeotroped with toluene. The residue was dissolved in DCM (300 mL). Azetidine hydrochloride (6.14 g, 65.5 mmol) then triethylamine (24 mL, 187 mmol) were added and the mixture stirred at ambient temperature for 20 hours. The mixture was concentrated under reduced pressure and ethyl acetate (400 mL) added to the residue. The resulting mixture was washed with water (100 mL), filtered, washed with 1M citric acid solution (50 mL), saturated sodium bicarbonate solution (50 mL) and brine (50 mL), dried (MgSO₄), filtered and the solvent removed under reduced pressure. The residue was purified by flash chromatography, eluting with a gradient of 0-40% ethyl acetate in isohexane to afford the product (8.8 g, 65%). m/z 242 (M+H)⁺.

Intermediate 35

10-Fluoro-5-methyl-2-oxa-6λ⁶-thia-5-azabicyclo[5.4.0]undeca-8,10,12-triene 6,6-dioxide

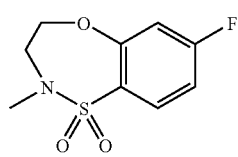

Sodium hydride (60% dispersion in mineral oil) (700 mg, 17.5 mmol) was added to a solution of 2,4-difluoro-N-(2-hydroxyethyl)-N-methyl-benzenesulfonamide (Intermediate 36) (2.0 g, 8.0 mmol) in DMF (200 mL) and the mixture stirred for 48 hours. The solvent was removed under reduced pressure, iced water (200 mL) was added and the mixture extracted into ethyl acetate (2×300 mL). The combined organic extract was washed with brine (40 mL), dried (MgSO₄), filtered and evaporated under reduced pressure. The residue was purified by flash chromatography, eluting with 20-50% ethyl acetate in isohexane, to afford the product (1.08 g, 58%). ¹H NMR δ (400 MHZ, CDCl₃): 2.79 (s, 3H), 3.75 (t, 2H), 4.23 (t, 2H), 6.88-6.97 (m, 2H), 7.82-7.86 (m, 1H); m/z 230 (M−H)⁻

Intermediate 36

2,4-Difluoro-N-(2-hydroxyethyl)-N-methyl-benzenesulfonamide

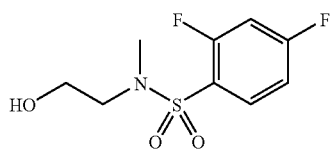

2,4-Difluorobenzenesulfonyl chloride (CAS no. 13918-92-8) (4.0 g, 19 mmol) in DCM (10 mL) was added slowly to a solution of 2-(methylamino)ethanol (1.66 mL, 20.7 mmol) in DCM (200 mL) and 10% sodium hydroxide solution (200 mL) at 0° C. The reaction was allowed to warm to room temperature and stirred for 20 hours. The DCM layer was separated and the aqueous re-extracted into DCM (2×50 mL). The combined organic extracts were washed with brine (200 mL), dried (MgSO₄), filtered and evaporated under reduced pressure to afford the product (4.7 g, 98%). ¹H NMR δ (400

MHz, CDCl₃): 1.98 (t, 1H), 2.94 (s, 3H), 3.32 (t, 2H), 3.79 (q, 2H), 6.94-7.03 (m, 2H), 7.89-7.95 (m, 1H).

Intermediate 37

3-Chloro-2,4-difluoro-N-(2-hydroxyethyl)-N-methyl-benzamide

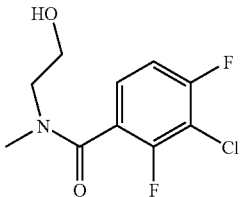

3-Chloro-2,4-difluorobenzoylchloride (CAS no. 157373-00-7) (211 mg, 1 mmol) in DCM (1 mL) was added to a stirred solution of 2-(methylamino)ethanol (83 mg, 1.1 mmol) in a mixture of DCM (1 mL) and 10% sodium hydroxide solution (1 mL) at 0° C. The mixture was warmed to room temperature and stirred for approximately 4 hours. The two layers were separated and the aqueous layer was extracted with DCM (3×30 mL). The organic layers were combined, dried (MgSO₄), filtered and evaporated to afford the product (180 mg, 61%). ¹H NMR δ (400 MHz, CDCl₃): 3.01 (s, 3H), 3.37 (t, 1H), 3.74 (t, 2H), 3.92 (t, 2H), 7.06 (td, 1H), 7.28-7.37 (m, 1H).

Intermediate 38

9-Fluoro-4-methyl-2-oxa-4-azabicyclo[4.4.0]deca-7,9,11-trien-5-one

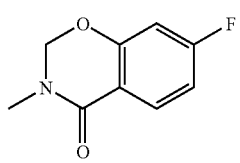

A mixture of 4-fluoro-2-hydroxy-N-methyl-benzamide (Intermediate 39) (0.30 g, 1.8 mmol) in formaldehyde (37% aqueous solution, 2 mL) and formic acid (2 mL) was refluxed for 1 hour then poured onto ice. The mixture was neutralised with sodium carbonate and extracted into chloroform (3×30 mL). The combined organics were dried (MgSO₄), and evaporated under reduced pressure. The residue was purified by flash chromatography, eluting with 10-50% ethyl acetate in isohexane to afford the product (0.24 g, 74%). ¹H NMR δ (400 MHZ, CDCl₃): 3.12 (s, 3H), 5.21 (s, 2H), 6.69 (dd, 1H), 6.84 (td, 1H), 7.98 (dd, 1H)

Intermediate 39

4-Fluoro-2-hydroxy-N-methyl-benzamide

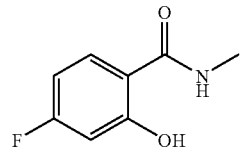

DMF (2 drops) was added to a mixture of 4-fluoro-2-hydroxy-benzoic acid (2.0 g, 13 mmol) and oxalyl chloride (2.85 mL, 32.0 mmol) in THF (15 mL). The reaction was stirred for 2 hours then evaporated under reduced pressure. The residue was dissolved in THF (10 mL) and added dropwise to 2M methylamine in THF (32 mL) at 0° C. The reaction was stirred at RT for 72 hours and the THF removed under reduced pressure. The residue was partitioned between ethyl acetate (80 mL) and water (80 mL). The aqueous layer was further extracted into ethyl acetate (80 mL) and the combined organic extracts were washed with brine (50 mL), dried (MgSO₄) and evaporated under reduced pressure. The residue was purified by flash chromatography, eluting with 5-40% ethyl acetate in isohexane, to afford the product (1.43 g, 65%). ¹H NMR δ (CDCl₃): 3.04 (d, 3H), 6.25 (s, 1H), 6.58 (td, 1H), 6.70 (dd, 1H), 7.34 (dd, 1H), 12.72 (s, 1H); m/z 170 (M+H)⁺.

Intermediate 40 tert-Butyl 3-[[3-[(2,2-dioxo-6-oxa-2-λ⁶-thiabicyclo[5.4.0]undeca-7,9,11-trien-9-yl)oxy]-5-[(3S)-1-methyl-2-oxo-pyrrolidin-3-yl]oxy-benzoyl]amino]pyrazole-1-carboxylate

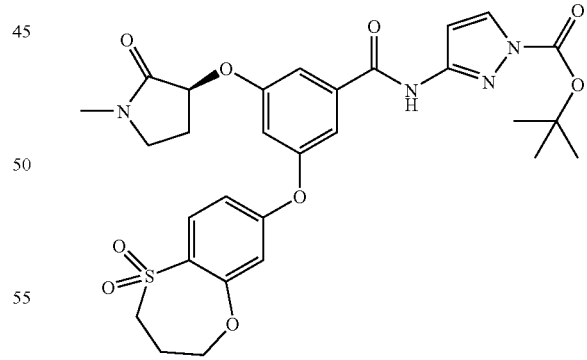

1-Chloro-N,N,2-trimethyl-prop-1-en-1-amine (0.142 mL, 1.07 mmol) was added to a solution of the 3-[(2,2-dioxo-6-oxa-2-λ⁶-thiabicyclo[5.4.0]undeca-7,9,11-trien-9-yl)oxy]-5-[(3S)-1-methyl-2-oxo-pyrrolidin-3-yl]oxy-benzoic acid (Intermediate 41) (355 mg, 0.8 mmol) in dichloromethane (10 mL) and stirred at ambient temperature for 30 minutes. tert-Butyl 3-aminopyrazole-1-carboxylate (CAS no. 863504-94-1) (293 mg, 1.6 mmol) and pyridine (0.13 mL, 1.6 mmol)

were added and the reaction stirred for 20 hours. The solvent was removed under reduced pressure. The residue was taken up in ethyl acetate (30 mL), washed with water (2×10 mL), citric acid (1N, 10 mL), saturated sodium bicarbonate solution (10 mL) and brine (10 mL), dried (MgSO$_4$) and evaporated under reduced pressure. The residue was purified by flash chromatography on silica eluting with a gradient of 0-100% ethyl acetate in isohexane to afford the product (412 mg, 84%). m/z 613 (M+H$^+$)

Intermediate 41

3-[(2,2-Dioxo-6-oxa-2-λ$^6$-thiabicyclo[5.4.0]undeca-7,9,11-trien-9-yl)oxy]-5-[(3S)-1-methyl-2-oxo-pyrrolidin-3-yl]oxy-benzoic acid

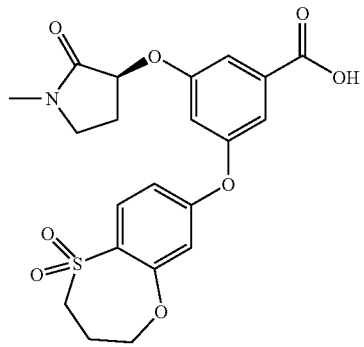

Methyl 3-[(2,2-dioxo-6-oxa-2-λ$^6$-thiabicyclo[5.4.0]undeca-7,9,11-trien-9-yl)oxy]-5-[(3S)-1-methyl-2-oxo-pyrrolidin-3-yl]oxy-benzoate (Intermediate 42) (876 mg, 1.9 mmol) was dissolved in THF (18 mL) and methanol (6 mL) and LiOH (1N, 2.3 mL) was added followed by water (20 mL). The resulting mixture was stirred for 16 hours at room temperature. The majority of the organic solvent was removed by distillation, the remaining aqueous solution was filtered then acidified with 2N HCl and extracted with ethyl acetate (2×30 mL). The combined organic extracts were washed with water (2×20 mL) and brine (20 mL), dried (MgSO$_4$) and the solvent removed under reduced pressure to afford the product (823 mg, 95%). $^1$H NMR δ (300.072 MHz, CDCl$_3$) 2.13-2.26 (m, 1H), 2.34-2.45 (m, 2H), 2.55-2.69 (m, 1H), 2.97 (s, 3H), 3.29-3.62 (m, 4H), 4.22 (t, 2H), 5.00 (t, 1H), 6.72 (s, 1H), 6.79 (d, 1H), 6.87 (s, 1H), 7.28 (s, 1H), 7.58 (s, 1H), 7.86 (d, 1H); m/z 448 (M+H$^+$).

Intermediate 42

Methyl 3-[(2,2-dioxo-6-oxa-2-λ$^6$-thiabicyclo[5.4.0]undeca-7,9,11-trien-9-yl)oxy]-5-[(3S)-1-methyl-2-oxo-pyrrolidin-3-yl]oxy-benzoate

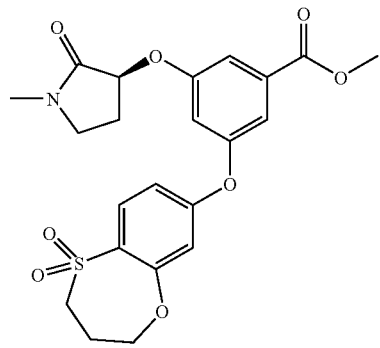

A mixture of methyl 3-hydroxy-5-[(3S)-1-methyl-2-oxo-pyrrolidin-3-yl]oxy-benzoate (Intermediate 8) (795 mg, 3 mmol), 9-fluoro-6-oxa-2-λ$^6$-thiabicyclo[5.4.0]undeca-8,10,12-triene 2,2-dioxide (Intermediate 23) (779 mg, 3.6 mmol) and potassium carbonate (828 mg, 6 mmol) in acetonitrile (30 mL) was stirred in the microwave at 160° C. for 5 hours. The solution was evaporated under reduced pressure, the residue dissolved in ethyl acetate (40 mL), washed with water (2×20 mL) and brine (20 mL), dried (MgSO$_4$) and the solvent removed under reduced pressure. The aqueous phase was acidified with 2N HCl extracted with ethyl acetate (2×30 mL), washed with water (2×20 mL) and brine (20 mL), dried (MgSO$_4$), and evaporated under reduced pressure. The residue from the second extraction was dissolved in THF (2 mL) and methanol (1 mL) and treated with 2M TMS diazomethane (0.22 mL), stirred for 30 minutes then evaporated. The resulting residue was combined with that from the initial extraction and purified by flash chromatography on silica eluting with 0-4% methanol in DCM and further purified by flash chromatography on silica eluting with 50-100% ethyl acetate in isohexane to afford the product (876 mg, 63%). $^1$H NMR δ (300 MHz, CDCl$_3$) 2.11-2.27 (m, 1H), 2.38-2.48 (m, 2H), 2.52-2.67 (m, 1H), 2.94 (s, 3H), 3.30-3.56 (m, 4H), 3.90 (s, 3H), 4.24 (t, 2H), 4.91 (t, 1H), 6.73 (s, 1H), 6.85 (d, 1H), 7.00 (s, 1H), 7.35 (s, 1H), 7.56 (s, 1H), 7.91 (d, 1H); m/z 462 (M+H$^+$).

Intermediate 43

3-[(9-methyl-10-oxo-7-oxa-9-azabicyclo[4.4.0]deca-2,4,11-trien-4-yl)oxy]-5-[(3S)-1-methyl-2-oxo-pyrrolidin-3-yl]oxy-benzoic acid

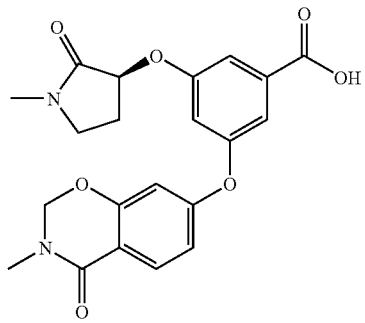

Methyl 3-[(4-methyl-5-oxo-2-oxa-4-azabicyclo[4.4.0]deca-6,8,10-trien-9-yl)oxy]-5-[(3S)-1-methyl-2-oxo-pyrrolidin-3-yl]oxy-benzoate (Intermediate 44) (232 mg, 0.54 mmol) was dissolved in THF (6 mL) and methanol (2 mL) and lithium hydroxide (1N, 0.65 mL) was added followed by water (10 mL), the resulting mixture was stirred for 16 hours at room temperature. The majority of the organic solvent was removed by evaporation under reduced pressure. The remainder was filtered, acidified to pH 1 with 2N hydrochloric acid. The mixture was extracted with ethyl acetate (2×30 mL). The combined organic extracts were washed with water (2×20 mL), brine (20 mL), dried (MgSO$_4$) and evaporated to afford the product (209 mg, 95%). $^1$H NMR δ (300 MHz, CDCl$_3$) 2.12-2.24 (m, 1H), 2.54-2.68 (m, 1H), 2.96 (s, 3H), 3.08 (s, 3H), 3.35-3.58 (m, 2H), 4.98 (t, 1H), 5.13 (s, 2H), 6.47 (s, 1H), 6.69 (d, 1H), 6.89 (s, 1H), 7.30 (s, 1H), 7.54 (s, 1H), 7.88 (d, 1H); m/z 413 (M+H$^+$).

Intermediate 44

Methyl 3-[(4-methyl-5-oxo-2-oxa-4-azabicyclo[4.4.0]deca-6,8,10-trien-9-yl)oxy]-5-[(3S)-1-methyl-2-oxo-pyrrolidin-3-yl]oxy-benzoate

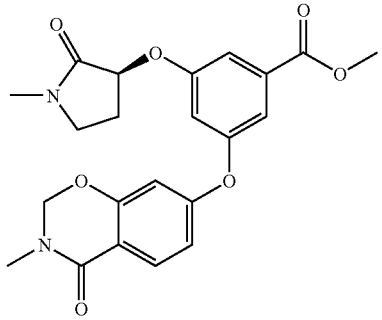

A mixture of methyl 3-hydroxy-5-[(3S)-1-methyl-2-oxo-pyrrolidin-3-yl]oxy-benzoate (Intermediate 8) (0.27 g, 1 mmol), 9-fluoro-4-methyl-2-oxa-4-azabicyclo[4.4.0]deca-6,8,10-trien-5-one (CAS no. 915771-24-3) (200 mg, 11 mol) and potassium carbonate (276 g, 2 mmol) in acetonitrile (20 mL) was heated in a microwave at 160° C. for 12 hours. The mixture was evaporated and the residue partitioned between ethyl acetate (40 mL) and water (40 mL). The organic phase was separated, washed with water (10 mL) and brine (20 mL), dried (MgSO$_4$) and evaporated. The aqueous phase was acidified to pH 1 with 2N hydrochloric acid extracted with ethyl acetate (2×30 mL). The combined organic extracts were washed with water (2×20 mL), brine (20 mL), dried (MgSO$_4$) and evaporated. The residue was dissolved in THF (2 mL) and methanol (1 mL) and treated with 2M TMS-diazomethane (0.14 mL) stirred for 30 minutes. The mixture was evaporated and the residue combined with that from the initial extraction and purified by flash chromatography on silica eluting with 0 to 100% ethyl acetate in isohexane to afford the product (232 mg, 54%). $^1$H NMR δ (300 MHz, CDCl$_3$) 2.10-2.25 (m, 1H), 2.53-2.66 (m, 1H), 2.93 (s, 3H), 3.09 (s, 3H), 3.32-3.58 (m, 2H), 3.89 (s, 3H), 4.91 (t, 1H), 5.17 (s, 2H), 6.51 (s, 1H), 6.72 (d, 1H), 6.97 (s, 1H), 7.34 (s, 1H), 7.52 (s, 1H), 7.93 (d, 1H); m/z 427 (M+H$^+$).

Intermediate 45

3-[5-(Dimethylcarbamoyl)pyrazin-2-yl]oxy-5-[(3S)-1-methyl-2-oxo-pyrrolidin-3-yl]oxy-benzoic acid

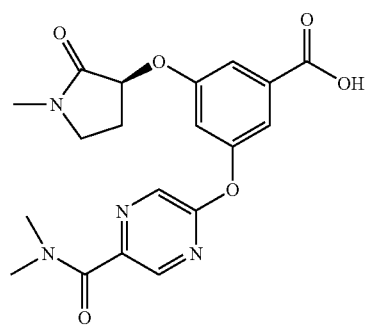

The methyl 3-[5-(dimethylcarbamoyl)pyrazin-2-yl]oxy-5-[(3S)-1-methyl-2-oxo-pyrrolidin-3-yl]oxy-benzoate (Intermediate 46) (772 mg, 1.86 mmol) was dissolved in THF (9 mL) and methanol (3 mL) and lithium hydroxide solution (1N, 2.2 mL) was added followed by water (25 mL). The resulting mixture was stirred for 1 hour at room temperature. The majority of the organic solvent was removed by distillation under reduced pressure. The remaining aqueous solution was extracted with ethyl acetate (10 mL) then acidified with 2N citric acid and re-extracted with ethyl acetate (5×25 mL), the combined organic extracts were washed with water (10 mL) and brine (20 mL), dried (MgSO$_4$) and evaporated to afford the product (716 mg, 96%). $^1$H NMR δ (300 MHz, CDCl$_3$) 2.13-2.27 (m, 1H), 2.55-2.69 (m, 1H), 2.96 (s, 3H), 3.17 (d, 6H), 3.35-3.58 (m, 2H), 4.98 (t, 1H), 7.10 (s, 1H), 7.45 (s, 1H), 7.63 (s, 1H), 8.36 (s, 1H), 8.53 (s, 1H); m/z 401 (M+H$^+$).

Intermediate 46: Methyl 3-[5-(dimethylcarbamoyl)pyrazin-2-yl]oxy-5-[(3S)-1-methyl-2-oxo-pyrrolidin-3-yl]oxy-benzoate

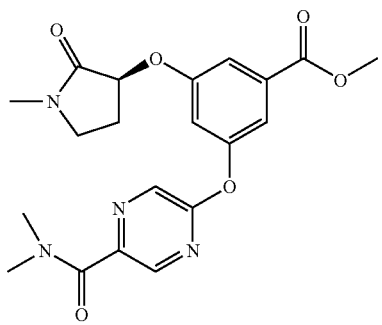

A mixture of methyl 3-hydroxy-5-[(3S)-1-methyl-2-oxo-pyrrolidin-3-yl]oxy-benzoate (Intermediate 8) (530 mg, 2 mmol), 5-chloro-N,N-dimethyl-pyrazine-2-carboxamide (CAS no. 915949-00-7) (446 mg, 2.4 mmol) and potassium carbonate (552 mg, 4 mmol) in acetonitrile (15 mL) was stirred at 120° C. for 2 hours. The mixture was evaporated and the residue dissolved in ethyl acetate (30 mL), washed with water (2×10 mL) and brine (20 mL), dried (MgSO$_4$) and evaporated. The residue was purified by flash chromatography on silica eluting with 50 to 100% ethyl acetate in isohexane to afford the product (772 mg, 93%). m/z 415 (M+H$^+$).

Biological Tests:

The biological effects of the compounds of formula (I) may be tested in the following way:

(1) Enzymatic Activity

Enzymatic activity of recombinant human pancreatic GLK may be measured by incubating GLK, ATP and glucose. The rate of product formation may be determined by coupling the assay to a G-6-P dehydrogenase, NADP/NADPH system and measuring the linear increase with time of optical density at 340 nm (Brocklehurst et al (Diabetes 2004, 53, 535-541). Activation of GLK by compounds can be assessed using this assay in the presence or absence of GLKRP as described in Brocklehurst et al (Diabetes 2004, 53, 535-541).

One or both of two variants of this assay, GKH1 and GKH4, were used to test the compounds of the invention. The GKH1 assay is a manual, bench-top rate assay using 60 nmol/l of recombinant human pancreatic GLK. The GLK activity rate is measured over a 5 minute window using a Multiskan Ascent spectrophotometer. The GKH4 assay is an automated end-point assay using 10 nmol/l of recombinant human pancreatic GLK. The GLK activity is measured at 10 minutes after the initiation of the assay on a Perkin Elmer Envision spectrophotometer. GKH1 and GKH4 do not contain GLKRP.

Compounds of the invention generally have an activating activity for glucokinase with an $EC_{50}$ of less than about 20 μM, such as less than about 5 μM, such as less than about 1 μM, such as less than 500 nM, such as less than about 100 nM. Examples 1 to 32 activated glucokinase in the GKH1 and/or GHK4 variants of the assay with $EC_{50}$ values as shown below.

TABLE A

| Example Number | GKH1 $EC_{50}$ Value (μM) | GKH4 $EC_{50}$ Value (μM) |
|---|---|---|
| 1 | 0.09 | 0.30 |
| 2 | 3.93 | |
| 3 | | 0.29 |
| 4 | | 18.31 |
| 5 | | 0.15 |
| 6 | | 0.19 |
| 7 | | 0.57 |
| 8 | | 0.19 |
| 9 | | 0.12 |
| 10 | | 0.26 |
| 11 | 0.14 | 0.31 |
| 12 | 0.30 | 0.43 |
| 13 | 0.43 | 0.17 |
| 14 | | 0.08 |
| 15 | 0.10 | 0.35 |
| 16 | | 0.31 |
| 17 | | 0.60 |
| 18 | 3.34 | 7.23 |
| 19 | | 0.59 |
| 20 | 0.42 | 0.90 |
| 21 | 0.21 | 1.11 |
| 22 | 2.37 | 6.61 |
| 23 | 0.05 | 0.22 |
| 24 | 0.15 | 0.57 |
| 25 | 0.03 | 0.04 |
| 26 | | 0.39 |
| 27 | | 0.66 |
| 28 | | 0.57 |
| 29 | | 0.10 |
| 30 | | 0.06 |
| 31 | | 1.08 |
| 32 | | 0.06 |

Production of Recombinant GLK and GLKRP:

Human GLK and GLKRP cDNA was obtained by PCR from human pancreatic and hepatic mRNA respectively, using established techniques described in Sambrook J, Fritsch EF & Maniatis T, 1989. PCR primers were designed according to the GLK and GLKRP cDNA sequences shown in Tanizawa et al., Proc Natl Acad Sci 1991 Aug. 15; 88(16): 7294-7 1991 and Bonthron, D. T. et al 1994 (later corrected in and Warner, J. P. et al., Mamm Genome. 1995 August; 6(8): 532-61995).

Cloning in Bluescript II Vectors

GLK and GLKRP cDNA was cloned in E. coli using pBluescript II.

Transformations

E. Coli transformations were generally carried out by electroporation. 400 mL cultures of strains DH5a or BL21(DE3) were grown in L-broth to an OD 600 of 0.5 and harvested by centrifugation at 2,000 g. The cells were washed twice in ice-cold deionised water, resuspended in 1 mL 10% glycerol and stored in aliquots at −70° C. Ligation mixes were desalted using Millipore V Series™ membranes (0.0025 mm) pore size). 40 mL of cells were incubated with 1 mL of ligation mix or plasmid DNA on ice for 10 minutes in 0.2 cm electroporation cuvettes, and then pulsed using a Gene Pulser™ apparatus (BioRad) at 0.5 kVcm$^{-1}$, 250 mF. Transformants were selected on L-agar supplemented with tetracyline at 10 mg/mL or ampicillin at 100 mg/mL.

Expression

GLK was expressed from the vector pTB375NBSE in E. coli BL21 cells, producing a recombinant protein containing a 6-His tag immediately adjacent to the N-terminal methionine. Alternatively, another suitable vector is pET21 (+)DNA, Novagen, Cat number 697703. The 6-His tag was used to allow purification of the recombinant protein on a column packed with nickel-nitrilotriacetic acid agarose purchased from Qiagen (cat no 30250).

GLKRP was expressed from the vector pFLAG CTC (IBI Kodak) in E. coli BL21 cells, producing a recombinant protein containing a C-terminal FLAG tag. The protein was purified initially by DEAE Sepharose ion exchange followed by utilisation of the FLAG tag for final purification on an M2 anti-FLAG immunoaffinity column purchased from Sigma-Aldrich (cat no. A1205).

(2) Oral Glucose Tolerance Test (OGTT)

Oral glucose tolerance tests (G. J Coope et al, British Journal of Pharmacology, (2006) 149, 328-335) may be performed on conscious Zucker obese fa/fa rats (age 12-13 weeks or older) fed a high fat diet (45% kcal fat) for at least two weeks prior to experimentation. The animals are fasted for 2 hours before use for experiments. A test compound or a vehicle is given orally 120 minutes before oral administration of a glucose solution at a dose of 2 g/kg body weight. Blood glucose levels are measured using a Accucheck glucometer from tail bled samples taken at different time points before and after administration of glucose (time course of 60 minutes). A time curve of the blood glucose levels is generated and the area-under-the-curve (AUC) for 120 minutes calculated (the time of glucose administration being time zero). Percent reduction in glucose excursion is determined using the AUC in the vehicle-control group as zero percent reduction.

3) Glucokinase Activator Efficacy in Free Feeding Obese Male Zucker Fatty Rats

The glucose lowering efficacy of a glucokinase was assessed by measuring free feeding blood glucose levels in obese male Zucker fatty rats as follows. Rats were received from the AstraZeneca breeding unit at 9 weeks of age and allowed to acclimatise to a reverse light cycle (0900-2100 dark phase) for 3 weeks. On the study day the animals were split into two groups: vehicle group contains 10 animals and a single test group contains 8 animals; for each additional test group the control group size was increased by 2 animals. Animals were orally dosed, at a volume of 5 ml/kg, at 0800 (ie 1h prior to entering the dark phase) with vehicle (1% w/v Pluronic F127) or the test compound (formulated in 1% Pluronic F127) at 3 mg/kg. Blood glucose was measured from a 10 μl needle prick sample from the tail vein and determined using a Roche Accu-chek monitor. Measurements were taken at time zero (ie immediately prior to dosing), 0.5 h, 1 h, 2 h, 3 h, 4 h, 6 h, 8 h, 12 h and 24 h thereafter. Samples at the 12 h and 24 h time points were only taken if sufficient efficacy had been observed at the 8 hour time point.

REFERENCES

1 Printz, R. L., Magnuson, M. A. and Granner, D. K. (1993) Annual Review of Nutrition 13, 463-96

2 DeFronzo, R. A. (1988) Diabetes 37, 667-87

3 Froguel, P., Zouali, H., Vionnet, N., Velho, G., Vaxillaire, M., Sun, F., Lesage, S., Stoffel, M., Takeda, J. and Passa, P. (1993) New England Journal of Medicine 328, 697-702
4 Bell, G. I., Pilkis, S. J., Weber, I. T. and Polonsky, K. S. (1996) Annual Review of Physiology 58, 171-86
5 Velho, G., Petersen, K. F., Perseghin, G., Hwang, J. H., Rothman, D. L., Pueyo, M. E., Cline, G. W., Froguel, P. and Shulman, G. I. (1996) Journal of Clinical Investigation 98, 1755-61
6 Christesen, H. B., Jacobsen, B. B., Odili, S., Buettger, C., Cuesta-Munoz, A., Hansen, T., Brusgaard, K., Massa, O., Magnuson, M. A., Shiota, C., Matschinsky, F. M. and Barbetti, F. (2002) Diabetes 51, 1240-6
6a Gloyn, A. L., Noordam, K., Willemsen, M. A. A. P., Ellard, S., Lam, W. W. K., Campbell, I. W., Midgley, P., Shiota, C., Buettger, C., Magnuson, M. A., Matschinsky, F. M., and Hattersley, A. T.; Diabetes 52: 2433-2440
7 Glaser, B., Kesavan, P., Heyman, M., Davis, E., Cuesta, A., Buchs, A., Stanley, C. A., Thornton, P. S., Permutt, M. A., Matschinsky, F. M. and Herold, K. C. (1998) New England Journal of Medicine 338, 226-30
8 Caro, J. F., Triester, S., Patel, V. K., Tapscott, E. B., Frazier, N. L. and Dohm, G. L. (1995) Hormone & Metabolic Research 27, 19-22
9 Desai, U. J., Slosberg, E. D., Boettcher, B. R., Caplan, S. L., Fanelli, B., Stephan, Z., Gunther, V. J., Kaleko, M. and Connelly, S. (2001) Diabetes 50, 2287-95
10 Shiota, M., Postic, C., Fujimoto, Y., Jetton, T. L., Dixon, K., Pan, D., Grimsby, J., Grippo, J. F., Magnuson, M. A. and Chemington, A. D. (2001) Diabetes 50, 622-9
11 Ferre, T., Pujol, A., Riu, E., Bosch, F. and Valera, A. (1996) Proceedings of the National Academy of Sciences of the United States of America 93, 7225-30
12 Seoane, J., Barbera, A., Telemaque-Potts, S., Newgard, C. B. and Guinovart, J. J. (1999) Journal of Biological Chemistry 274, 31833-8
13 Moore, M. C., Davis, S, N., Mann, S. L. and Chemington, A. D. (2001) Diabetes Care 24, 1882-7
14 Alvarez, E., Roncero, I., Chowen, J. A., Vazquez, P. and Blazquez, E. (2002) Journal of Neurochemistry 80, 45-53
15 Lynch, R. M., Tompkins, L. S., Brooks, H. L., Dunn-Meynell, A. A. and Levin, B. E. (2000) Diabetes 49, 693-700
16 Roncero, I., Alvarez, E., Vazquez, P. and Blazquez, E. (2000) Journal of Neurochemistry 74, 1848-57
17 Yang, X. J., Kow, L. M., Funabashi, T. and Mobbs, C. V. (1999) Diabetes 48, 1763-1772
18 Schuit, F. C., Huypens, P., Heimberg, H. and Pipeleers, D. G. (2001) Diabetes 50, 1-11
19 Levin, B. E. (2001) International Journal of Obesity 25, supplement 5, S68-S72.
20 Alvarez, E., Roncero, I., Chowen, J. A., Thorens, B. and Blazquez, E. (1996) Journal of Neurochemistry 66, 920-7
21 Mobbs, C. V., Kow, L. M. and Yang, X. J. (2001) American Journal of Physiology—Endocrinology & Metabolism 281, E649-54
22 Levin, B. E., Dunn-Meynell, A. A. and Routh, V. H. (1999) American Journal of Physiology 276, R1223-31
23 Spanswick, D., Smith, M. A., Groppi, V. E., Logan, S. D. and Ashford, M. L. (1997) Nature 390, 521-5
24 Spanswick, D., Smith, M. A., Mirshamsi, S., Routh, V. H. and Ashford, M. L. (2000) Nature Neuroscience 3, 757-8
25 Levin, B. E. and Dunn-Meynell, A. A. (1997) Brain Research 776, 146-53
26 Levin, B. E., Govek, E. K. and Dunn-Meynell, A. A. (1998) Brain Research 808, 317-9
27 Levin, B. E., Brown, K. L. and Dunn-Meynell, A. A. (1996) Brain Research 739, 293-300
28 Rowe, I. C., Boden, P. R. and Ashford, M. L. (1996) Journal of Physiology 497, 365-77
29 Fujimoto, K., Sakata, T., Arase, K., Kurata, K., Okabe, Y. and Shiraishi, T. (1985) Life Sciences 37, 2475-82
30 Kurata, K., Fujimoto, K. and Sakata, T. (1989) Metabolism: Clinical & Experimental 38, 46-51
31 Kurata, K., Fujimoto, K., Sakata, T., Etou, H. and Fukagawa, K. (1986) Physiology & Behavior 37, 615-20
32 Jetton T. L., Liang Y., Pettepher C. C., Zimmerman E. C., Cox F. G., Horvath K., Matschinsky F. M., and Magnuson M. A., J. Biol. Chem., (February 1994) 269: 3641-3654.
33 Reimann F. and Gribble F. M., Diabetes 2002 51: 2757-2763
34 Cheung A. T., Dayanandan B., Lewis J. T., Korbutt G. S., Rajotte R. V., Bryer-Ash M., Boylan M. O., Wolfe M. M., Kieffer T. J., Science, 290, Issue 5498, 1959-1962 (8 Dec. 2000)

The invention claimed is:

1. A compound of Formula (I), or a salt thereof:

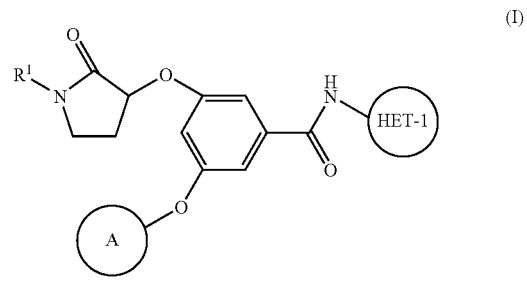

wherein:
$R^1$ is selected from (1-4C)alkyl and (3-6C)cycloalkyl;
HET-1 is a 5- or 6-membered, C-linked heteroaryl ring containing a nitrogen atom in the 2-position relative to the amide nitrogen to which the ring is attached and optionally 1 or 2 further ring heteroatoms independently selected from O, N, and S; which ring is optionally substituted on any nitrogen atom provided it is not thereby quaternised, by a substituent selected from $R^7$ and is optionally substituted on 1 or 2 available carbon atoms by a substituent independently selected from $R^6$;
Ring A is selected from phenyl, HET-2, and HET-3; wherein when Ring A is phenyl it is substituted with $R^2$ and optionally further substituted with a group selected from $R^3$;
$R^2$ is selected from —C(0)NR$^4$R$^5$, SO$_p$R$^4$, and —SO$_2$NR$^4$R$^5$;
$R^3$ is selected from halo, methyl, and trifluoromethyl;
$R^4$ is selected from hydrogen, (3-6C)cycloalkyl (optionally substituted with 1 group selected from $R^{15}$), HET-5 and (1-4C)alkyl optionally substituted by 1 or 2 substituents independently selected from HET-5, —OR$^5$, —SO$^2$R$^5$, (3-6C)cycloalkyl (optionally substituted with 1 group selected from $R^{15}$) and C(O)NR$^5$R$^5$;
HET-5 is a 4-, 5-, or 6-membered, C- or N-linked heterocyclyl ring containing 1, 2, 3, or 4 heteroatoms independently selected from O, N, and S, wherein a —CH$_2$— group can optionally be replaced by a —C(O)—, and wherein a sulphur atom in the heterocyclic ring may optionally be oxidised to a S(O) or S(O)$_2$ group; which ring is optionally substituted on an available carbon or nitrogen atom by 1 or 2 (1-4C)alkyl substituents;

R⁵ is hydrogen or (1-4C)alkyl; or

R⁴ and R⁵ together with the nitrogen atom to which they are attached form a 4- to 7-membered saturated or partially unsaturated heterocyclyl ring, optionally containing 1 or 2 further heteroatoms in addition to the linking N atom, independently selected from O, N, and S, wherein a —CH₂— group can optionally be replaced by a —C(O)— and wherein a sulphur atom in the ring may optionally be oxidised to a S(O) or S(O)₂ group; which ring is optionally substituted on an available carbon atom by 1 or 2 substituents independently selected from R⁸ and is optionally substituted on an available nitrogen atom by a substituent selected from R⁹; or R⁴ and R⁵ together with the nitrogen atom to which they are attached form a 6- to 10-membered bicyclic saturated or partially unsaturated heterocyclyl ring, optionally containing 1 further nitrogen atom in addition to the linking N atom, wherein a —CH₂— group can optionally be replaced by a —C(O)—; which ring is optionally substituted on an available carbon by 1 substituent selected from hydroxy, methyl, and halo, or on an available nitrogen atom by methyl;

R⁶ is independently selected from (1-4C)alkyl, halo, hydroxy(1-4C)alkyl, (1-4C)alkoxy(1-4C)alkyl, (1-4C)alkylS(O)ₚ(1-4C)alkyl, amino(1-4C)alkyl, (1-4C)alkylamino(1-4C)alkyl, and di(1-4C)alkylamino(1-4C)alkyl;

R⁷ is independently selected from (1-4C)alkyl, hydroxy(1-4C)alkyl, (1-4C)alkoxy(1-4C)alkyl, (1-4C)alkylS(O)ₚ(1-4C)alkyl, amino(1-4C)alkyl, (1-4C)alkylamino(1-4C)alkyl, and di(1-4C)alkylamino(1-4C)alkyl;

R⁸ is selected from hydroxy, (1-4C)alkoxy, (1-4C)alkyl, aminocarbonyl, (1-4C)alkylaminocarbonyl, di(1-4C)alkylaminocarbonyl, (1-4C)alkylamino, di(1-4C)alkylamino, (1-4C)alkoxy(1-4C)alkyl, hydroxy(1-4C)alkyl, and —S(O)ₚ(1-4C)alkyl;

R⁹ is selected from (1-4C)alkyl, —C(O)(1-4C)alkyl, aminocarbonyl, (1-4C)alkylaminocarbonyl, di(1-4C)alkylaminocarbonyl, (1-4C)alkoxy(1-4C)alkyl, hydroxy(1-4C)alkyl, and —S(O)ₚ(1-4C)alkyl;

HET-2 is a 5- or 6- membered heteroaryl ring, containing 1, 2, or 3 ring heteroatoms independently selected from O, S, and N; which ring is substituted on an available carbon atom by a substituent selected from R², and is optionally further substituted on 1 or 2 available carbon atoms by a substituent independently selected from R³ and is optionally substituted on an available nitrogen atom provided it is not thereby quaternised, by a substituent selected from R¹⁰;

R¹⁰ is selected from (1-4C)alkyl, (3-6C)cycloalkyl, hydroxy(1-4C)alkyl, (1-4C)alkoxy(1-4C)alkyl, —C(O)(1-4C)alkyl, benzyl, and (1-4C)alkylsulfonyl;

HET-3 is a fused bicyclic ring system of formula —B—C;

wherein B is a Ring is directly attached to the linking oxygen atom and Ring B is phenyl or is a 5- or 6-membered heteroaryl ring containing 1, 2, or 3 heteroatoms independently selected from O, N, and S provided there are no O—O, S—S or O—S bonds in the ring;

wherein Ring B is optionally substituted on any nitrogen atom by a substituent selected from R¹¹ and is optionally substituted on any available carbon atom by 1 or 2 substituents independently selected from R¹²;

R¹¹ is independently selected from (1-4C)alkyl, hydroxy(1-4C)alkyl, (1-4C)alkoxy(1-4C)alkyl, (1-4C)alkylS(O)ₚ(1-4C)alkyl, amino(1-4C)alkyl, (1-4C)alkylamino(1-4C)alkyl, di(1-4C)alkylamino(1-4C)alkyl, and HET-4;

R¹² is independently selected from (1-4C)alkyl, halo, hydroxy(1-4C)alkyl, (1-4C)alkoxy(1-4C)alkyl, (1-4C)alkylS(O)ₚ(1-4C)alkyl, amino(1-4C)alkyl, (1-4C)alkylamino(1-4C)alkyl, di(1-4C)alkylamino(1-4C)alkyl, and HET-4;

HET-4 is a 5- or 6-membered, C- or N- linked unsubstituted heteroaryl ring containing 1, 2, or 3 ring heteroatoms independently selected from O, N, and S;

Ring C is a 5- to 7-membered heterocyclic ring fused to Ring B, containing 1, 2, or 3 ring heteroatoms independently selected from O, S and N provided that there are no O—O, S—O or S—S bonds within the ring, wherein any ring carbon or sulfur atom may optionally be oxidised and wherein Ring C is optionally substituted on any nitrogen atom by a substituent selected from R¹³ and is optionally substituted on any available carbon atom by 1 or 2 substituents independently selected from R¹⁴;

R¹³ is selected from (1-4C)alkyl, (3-6C)cycloalkyl, benzyl, (1-4C)alkylcarbonyl, (1-4C)alkylsulphonyl, hydroxy(1-4C)alkyl, and (1-4C)alkoxy(1-4C)alkyl;

R¹⁴ is selected from (1-4C)alkyl, (3-6C)cycloalkyl, (1-4C)alkoxy, hydroxy, fluoro, and chloro;

R¹⁵ is independently selected from (1-4C)alkyl, hydroxy(1-4C)alkyl, and hydroxy; and p is independently at each occurrence 0, 1, or 2.

2. A compound of Formula (I) as claimed in claim 1, or a salt thereof, wherein Ring A is phenyl.

3. A compound of Formula (I) as claimed in claim 1, or a salt thereof, wherein Ring A is HET-2.

4. A compound of Formula (I) as claimed in claim 1, or a salt thereof, wherein Ring A is HET-3.

5. A compound of Formula (I) as claimed in any one of claims 1 to 4, or a salt thereof, wherein the compound of formula (I) has the (S)-configuration at the pyrrolidone ring and is thereby a compound of Formula (IA):

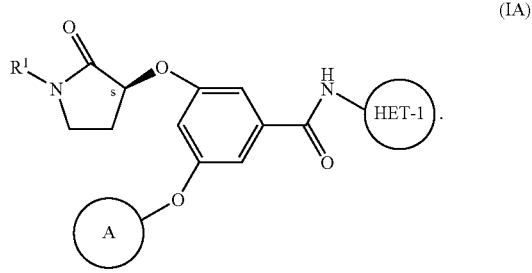

(IA)

6. A compound of the formula (I) as claimed in claim 1, which is any one of the following compounds, or a salt thereof:

3[6-(azetidine-1-carbonyl)pyridin-3-yl]oxy-5-[(3S)-1-methyl-2-oxo-pyrrolidin-3-yl]oxy-N-(5-methylpyrazin-2-yl)benzamide;

3-[6-(azetidine-1-carbonyl)pyridin-3-yl]oxy-5-[(3R)-1-methyl-2-oxo-pyrrolidin-3-yl]oxy-N-(5-methylpyrazin-2-yl)benzamide;

3-[5-(azetidine-1-carbonyl)pyrazin-2-yl]oxy-5-[(3S)-1-methyl-2-oxo-pyrrolidin-3-yl]oxy-N-(4-methyl1,3-thiazol-2-yl)benzamide;

3-[5-(azetidine- 1 -carbonyl)pyrazin-2-yl]oxy-5-[(3R)-1-methyl-2-oxo-pyrrolidin-3-yl]oxy-N-(4-methyl 1,3-thiazol-2-yl)benzamide;

3-[4-(azetidine-1-carbonyl)phenoxy]-5-[(3S)-1-methyl-2-oxo-pyrrolidin-3-yl]oxy-N-(1H -pyrazol-3-yl)benzamide;

3[5-(azetidine-1-carbonyl)-3-chloro-pyridin-2-yl]oxy-5-[(3S)-1-methyl-2-oxo-pyrrolidin-3-yl]oxy-N-(5-methylpyrazin-2-yl)benzamide;
3-[(3S)-1-methyl-2-oxo-pyrrolidin-3-yl]oxy-N-(5-methylpyrazin-2-yl)-5-(4-methylsulfonylphenoxy)benzamide;
3-[4-(azetidine-1-carbonyl)phenoxy]-5-[(3S)-1-methyl-2-oxo-pyrrolidin-3-yl]oxy-N-(5-methylpyrazin-2-yl)benzamide;
3-[(2,2-dioxo-6-oxa-2$\lambda^6$-thiabicyclo[5.4.0]undeca-7,9,11-trien-9-yl)oxy]-5-[(3S)-1-methyl-2-oxo-pyrrolidin-3-yl]oxy-N-(5-methylpyrazin-2-yl)benzamide;
3[6-(azetidine-1-carbonyl)pyridin-3-yl]oxy-5-(1-ethyl-2-oxo-pyrrolidin-3-yl)oxy-N-(5-methylpyrazin-2-yl)benzamide;
3-[(5-methyl-6,6-dioxo-2-oxa-6-$\lambda^6$-thia-5-azabicyclo[5.4.0]undeca-8,10,12-trien-10-yl)oxy]-5-(1-methyl-2-oxo-pyrrolidin-3-yl)oxy-N-(5-methylpyrazin-2-yl)benzamide;
3-[6-(azetidine-1-carbonyl)pyridin-3-yl]oxy-5-[(3 S)-1-methyl-2-oxo-pyrrolidin-3-yl]oxy-N -pyrazin-2-yl-benzamide;
3-[6-(azetidine-1-carbonyl)pyridin-3-yl]oxy-5-[(3S)-1-methyl-2-oxo-pyrrolidin-3-yl]oxy-N-pyridin-2-yl-benzamide;
3-[(11-chloro-5-methyl-6-oxo-2-oxa-5-azabicyclo[5.4.0]undeca-8,10,12-trien-10-yl)oxy]-5-[(3 S)- 1-methyl-2-oxo-pyrrolidin-3-yl]oxy-N-(5-methylpyrazin -2-yl)benzamide;
3-[(4-methyl-5-oxo-2-oxa-4-azabicyclo[4.4.0]deca-6,8,10-trien-9-yl)oxy]-5-(1-methyl-2-oxo -pyrrolidin-3-yl)oxy-N-(5-methylpyrazin-2-yl)benzamide;
3-[(5-methyl-6-oxo-2-oxa-5-azabicyclo[5.4.0]undeca-8,10,12-trien-10-yl)oxy]-5-[(3S)-1-methyl -2-oxo-pyrrolidin-3-yl]oxy-N-(5-methylpyrazin-2-yl)benzamide;
3-[6-(azetidine-1-carbonyl)pyridin-3-yl]oxy-5-(1-cyclobutyl-2-oxo-pyrrolidin-3-yl)oxy-N-(5-methylpyrazin-2-yl)benzamide;
3-[6-(Azetidine- 1-carbonyl)pyridin-3-yl]oxy-5-[(3R)-1-cyclopropyl-2-oxo-pyrrolidin-3-yl]oxy -N-(5-methylpyrazin-2-yl)benzamide;
3-[6-(Azetidine- 1-carbonyl)pyridin-3-yl]oxy-5-[(3 S)-1-cyclopropyl-2-oxo-pyrrolidin-3-yl]oxy -N-(5-methylpyrazin-2-yl)benzamide;
3-[6-(Azetidine-1-carbonyl)pyridin-3-yl]oxy-5-[(3S)-1-cyclobutyl-2-oxo-pyrrolidin-3-yl]oxy-N -(5-methylpyrazin-2-yl)benzamide;
3[6-(Azetidine-1-carbonyl)pyridin-3-yl]oxy-5-[(3S)-1-cyclobutyl-2-oxo-pyrrolidin-3-yl]oxy-N -(5-methylpyrazin-2-yl)benzamide;
3-[6-(Azetidine- 1-carbonyl)pyridin-3-yl]oxy-5-[(3R)-1-ethyl-2-oxo-pyrrolidin-3-yl]oxy-N-(5-methylpyrazin-2-yl)benzamide;
3-[6-(Azetidine-1-carbonyl)pyridin-3-yl]oxy-5-[(3S)-1-ethyl-2-oxo-pyrrolidin-3-yl]oxy-N-(5-methylpyrazin-2-yl)benzamide;
N,N-Dimethyl-5-[3-[(3 S)- 1-methyl-2-oxo-pyrrolidin-3-yl]oxy-5-[(5-methylpyrazin-2-yl)carbamoyl]phenoxy]pyrazine-2-carboxamide;
3-[(2,2-Dioxo-6-oxa-2-$\lambda^6$-thiabicyclo[5.4.0]undeca-7,9,11-trien-9-yl)oxy]-5-[(3S)-1-methyl-2-oxo-pyrrolidin-3-yl]oxy-N-(1H-pyrazol-3-yl)benzamide;
3-[2-Chloro-4-(dimethylcarbamoyl)phenoxy]-5-[(3S)-1-methyl-2-oxo-pyrrolidin-3-yl]oxy-N-(5-methylpyrazin-2-yl)benzamide;
3-[(6,6-dioxo-2-oxa-6-$\lambda^6$-thia-5-azabicyclo[5.4.0]undeca-8,10,12-trien-10-yl)oxy]-5-[(3S)-1-methyl-2-oxo-pyrrolidin-3-yl]oxy-N-(5-methylpyrazin-2-yl)benzamide;
3-[(3S)-1-methyl-2-oxo-pyrrolidin-3-yl]oxy-N-(5-methylpyrazin-2-yl)-5-(6-methylsulfonylpyridin -3-yl)oxybenzamide;
N,N-dimethyl-5-[3-[(3S)-1-methyl-2-oxo-pyrrolidin-3-yl]oxy-5-[(5-methylpyrazin-2-yl)carbamoyl]phenoxy]pyridine-2-carboxamide;
3-[(9-methyl-10-oxo-7-oxa-9-azabicyclo[4.4.0]deca -2,4,11-trien-4-yl)oxy]-5-[(3S)-1-methyl-2-oxo-pyrrolidin-3-yl]oxy-N-(1H-pyrazol-3-yl)benzamide;
N,N-dimethyl-5-[3-[(3S)-1-methyl-2-oxo-pyrrolidin-3-yl]oxy-5-[(3-methyl-1,2,4-thiadiazol-5-yl)carbamoyl]phenoxy]pyrazine-2-carboxamide; and
N,N-Dimethyl-5-[3-[(3S)-1-methyl-2-oxo-pyrrolidin-3-yl]oxy-5-[(4-methyl-1,3-thiazol-2-yl)carbamoyl]phenoxy]pyrazine-2-carboxamide.

7. A pharmaceutical composition comprising a compound according to claim 1, or a pharmaceutically-acceptable salt thereof, together with a pharmaceutically acceptable diluent or carrier.

8. A method of treating type 2 diabetes comprising administering an effective amount of a compound of Formula (I) as claimed in claim 1 or a pharmaceutically-acceptable salt thereof, to a mammal in need of such treatment.

9. A process for the preparation of a compound of Formula (I) as claimed in claim 1 which comprises a process (a) to (g):

(a) reacting an acid of Formula (V) with a compound of Formula (VI),

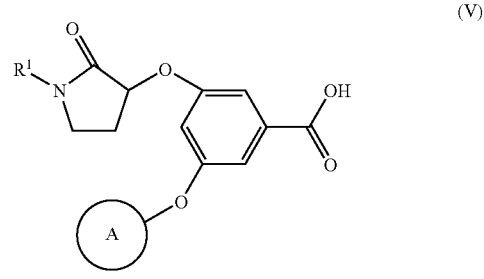

or (b) reacting a compound of Formula (VII) with a compound of Formula (VIII),

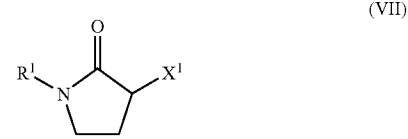

-continued (VIII)

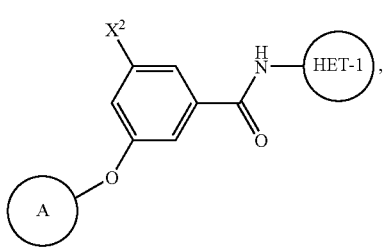

wherein $X^1$ is a leaving group and $X^2$ is a hydroxyl group; or $X^1$ is a hydroxyl group and $X^2$ is a leaving group;

or reacting a compound of Formula (VII) with the intermediate ester of Formula (IX), wherein $P^1$ is a protecting group, followed by ester hydrolysis and amide formation, (VII)

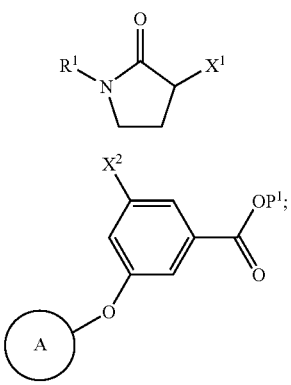

(XI)

or (c) reacting a compound of Formula (X) with a compound of Formula (XI), (X)

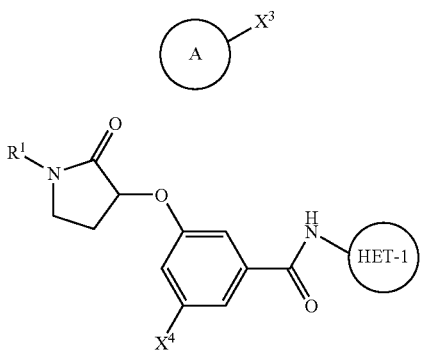

(XI)

wherein $X^3$ is a leaving group or an organometallic reagent and $X^4$ is a hydroxyl group or $X^3$ is a hydroxyl group and $X^4$ is a leaving group or an organometallic reagent;

or reacting a compound of Formula (X) with the intermediate ester of Formula (XII), followed by ester hydrolysis and amide formation, (X)

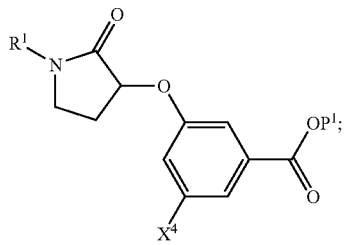

(XII)

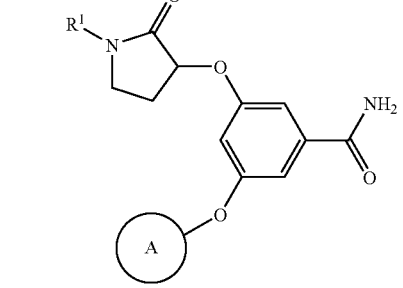

or (d) reacting a compound of Formula (XIII) with a compound of Formula (XIV), (XIII)

(XIV)

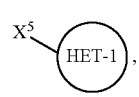

wherein $X^5$ is a leaving group; or e) when A is phenyl or HET-2, by reacting a compound of Formula (XV)

(XV)

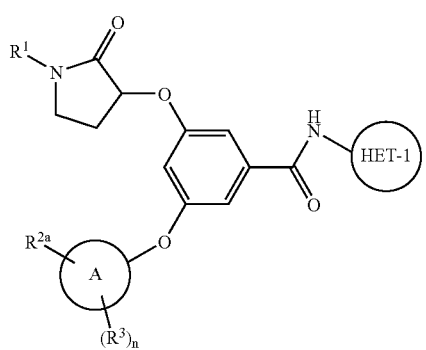

with an amine of Formula NR$^4$R$^5$, wherein R$^{2a}$ is a carboxylic acid, ester or anhydride (for R$^2$ = —CONR$^4$R$^5$) or the sulfonic acid equivalents (for R$^2$ is —SO$^2$NR$^4$R$^5$); or when A is HET-3, by cyclising a compound of Formula (XVI) to a compound of Formula (I)

(XVI)

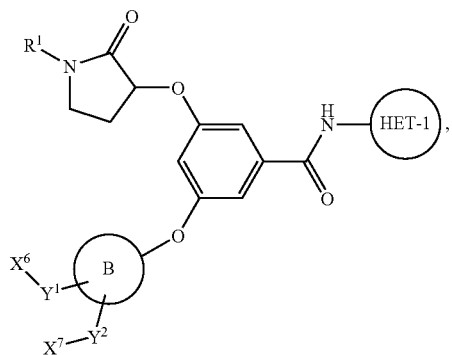

wherein Y$^1$ and Y$^2$ are 0-4 atom linkers; wherein each linker atom is independently selected from C, N, S, or O and wherein any C or S can be optionally oxidised and any atom can be optionally substituted provided it is not quaternised and there are no S—S or O—O bonds, X$^6$ can be any nucleophilic species and X$^7$ a leaving group or vice versa;

or cyclising the intermediate ester of Formula (XVII) to a compound of Formula (I), followed by ester hydrolysis and amide formation, (XVII)

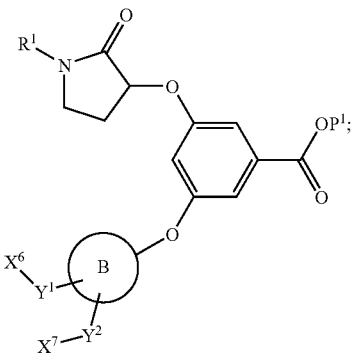

or (g) reacting a compound of Formula (XX) with a (1-4C) alkylamine or (3-6C)cycloalkylamine;

(XX)

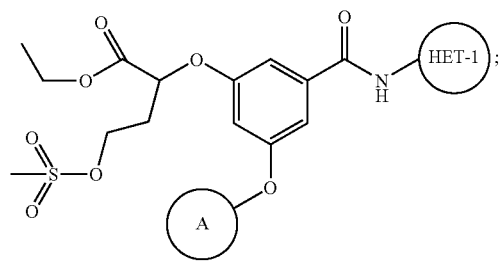

and thereafter, if necessary:
i) removing any protecting groups; or
ii) forming a salt thereof.

* * * * *